(12) United States Patent
Thackray et al.

(10) Patent No.: US 11,707,474 B2
(45) Date of Patent: Jul. 25, 2023

(54) METHODS FOR TREATING ACUTE MYELOID LEUKEMIA AND RELATED CONDITIONS

(71) Applicant: GlycoMimetics, Inc., Rockville, MD (US)

(72) Inventors: Helen M. Thackray, Bethesda, MD (US); Henry H. Flanner, Montgomery Village, MD (US); Curt D. Wolfgang, Durham, NC (US)

(73) Assignee: GlycoMimetics, Inc., Rockville, MD (US)

( * ) Notice: Subject to any disclaimer, the term of this patent is extended or adjusted under 35 U.S.C. 154(b) by 0 days.

(21) Appl. No.: 16/978,508

(22) PCT Filed: Mar. 4, 2019

(86) PCT No.: PCT/US2019/020574
§ 371 (c)(1),
(2) Date: Sep. 4, 2020

(87) PCT Pub. No.: WO2019/173229
PCT Pub. Date: Sep. 12, 2019

(65) Prior Publication Data
US 2021/0069220 A1    Mar. 11, 2021

Related U.S. Application Data

(60) Provisional application No. 62/638,569, filed on Mar. 5, 2018.

(51) Int. Cl.
*A61K 31/702* (2006.01)
*A61P 35/00* (2006.01)
*A61K 9/00* (2006.01)

(52) U.S. Cl.
CPC .......... *A61K 31/702* (2013.01); *A61K 9/0019* (2013.01); *A61P 35/00* (2018.01)

(58) Field of Classification Search
CPC ...... A61K 31/702; A61K 9/0019; A61P 35/00
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Amadori (Journal of Clinical Oncology; 9, No. 7, 1991, 1210-1214; abstract only).*
Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al., "A rapid microplate method for quantifying inhibition of bacterial adhesion to eukaryotic cells," Journal of Microbiological Methods 60: 55-62, 2005.

(Continued)

*Primary Examiner* — Pancham Bakshi
(74) *Attorney, Agent, or Firm* — Finnegan, Henderson, Farabow, Garrett & Dunner LLP

(57) ABSTRACT

Methods for treating or inhibiting cancer and/or one or more related conditions by administering to a subject in need thereof an effective amount of a compound of Formula (I), a prodrug thereof, or a pharmaceutically acceptable salt of any of the foregoing. For example, methods for treating AML, MDS, neutropenia, and/or mucositis comprising administering a pharmaceutical composition comprising a compound of Formula (I) are described.

57 Claims, 31 Drawing Sheets

(56) References Cited

U.S. PATENT DOCUMENTS

| | | |
|---|---|---|
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 * | 8/2015 | Magnani ............... C07H 15/207 |
| 9,254,322 B2 | 2/2016 | Levesque et al. |
| 9,486,497 B2 | 11/2016 | Levesque et al. |
| 9,534,009 B2 | 1/2017 | Magnani |
| 9,796,745 B2 | 10/2017 | Magnani et al. |
| 9,867,841 B2 | 1/2018 | Magnani |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0086356 A1 | 7/2002 | Tuschi et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0165178 A1 | 11/2002 | Schetter et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0073632 A1 | 4/2003 | Ciaccia et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |
| 2005/0187171 A1 | 8/2005 | Magnani et al. |
| 2005/0214283 A1 | 9/2005 | Sackstein et al. |
| 2006/0194745 A1 | 8/2006 | Magnani et al. |
| 2006/0217303 A1 | 9/2006 | Kriegler |
| 2006/0264451 A1 | 11/2006 | Shim et al. |

(56) References Cited

U.S. PATENT DOCUMENTS

| | | |
|---|---|---|
| 2006/0287253 A1 | 12/2006 | Kriegler et al. |
| 2007/0021378 A1 | 1/2007 | Varki et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0245265 A1 | 10/2011 | Zuk et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1 | 7/2013 | Magnani et al. |
| 2013/0261070 A1 | 10/2013 | Magnani et al. |
| 2013/0281646 A1 | 10/2013 | Korzekwa et al. |
| 2013/0331350 A1 | 12/2013 | Ernst et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2015/0110808 A1 | 4/2015 | Magnani et al. |
| 2015/0284420 A1 | 10/2015 | Magnani et al. |
| 2016/0145290 A1 | 5/2016 | Magnani et al. |
| 2016/0184339 A1 | 6/2016 | Magnani |
| 2016/0193294 A1 | 7/2016 | Magnani et al. |
| 2016/0243145 A1 | 8/2016 | Magnani et al. |
| 2016/0289257 A1 | 10/2016 | Magnani et al. |
| 2016/0333043 A1 | 11/2016 | Magnani et al. |
| 2018/0228871 A1* | 8/2018 | King .................. A61P 35/00 |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/25043 | 11/1994 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 95/31210 | 11/1995 |
| WO | WO 96/20204 | 7/1996 |
| WO | WO 96/25418 | 8/1996 |
| WO | WO 96/26950 | 9/1996 |
| WO | WO 96/40942 | 12/1996 |
| WO | WO 97/01355 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/046771 | 10/1998 |
| WO | WO 99/42130 | 8/1999 |
| WO | WO 99/43353 | 9/1999 |
| WO | WO 99/43356 | 9/1999 |
| WO | WO 99/065712 | 12/1999 |
| WO | WO 00/02870 | 1/2000 |
| WO | WO 00/050032 | 8/2000 |
| WO | WO 00/066112 | 11/2000 |
| WO | WO 01/89564 | 11/2001 |
| WO | WO 02/22820 | 3/2002 |
| WO | WO 02/062810 | 8/2002 |
| WO | WO 03/032925 | 4/2003 |
| WO | WO 03/055876 | 7/2003 |
| WO | WO 03/088980 | 10/2003 |
| WO | WO 03/097658 | 11/2003 |
| WO | WO 04/004636 | 1/2004 |
| WO | WO 04/033663 | 4/2004 |
| WO | WO 04/058304 | 7/2004 |
| WO | WO 04/094619 | 11/2004 |
| WO | WO 05/016349 | 2/2005 |
| WO | WO 05/046597 | 5/2005 |
| WO | WO 05/051920 | 6/2005 |
| WO | WO 05/054264 | 6/2005 |
| WO | WO 05/058934 | 6/2005 |
| WO | WO 05/085219 | 9/2005 |
| WO | WO 05/116088 | 12/2005 |
| WO | WO 06/017180 | 2/2006 |
| WO | WO 06/022454 | 3/2006 |
| WO | WO 06/062946 | 6/2006 |
| WO | WO 06/074426 | 7/2006 |
| WO | WO 06/074428 | 7/2006 |
| WO | WO 06/089106 | 8/2006 |
| WO | WO 06/127906 | 11/2006 |
| WO | WO 07/021721 | 2/2007 |
| WO | WO 07/022089 | 2/2007 |
| WO | WO 07/022385 | 2/2007 |
| WO | WO 07/028050 | 3/2007 |
| WO | WO 07/033329 | 3/2007 |
| WO | WO 08/008852 | 1/2008 |
| WO | WO 08/008854 | 1/2008 |
| WO | WO 08/011094 | 1/2008 |
| WO | WO 08/060378 | 5/2008 |
| WO | WO 08/100453 | 8/2008 |
| WO | WO 08/109154 | 9/2008 |
| WO | WO 09/011889 | 1/2009 |
| WO | WO 09/073911 | 6/2009 |
| WO | WO 09/073916 | 6/2009 |
| WO | WO 09/126556 | 10/2009 |
| WO | WO 09/152245 | 12/2009 |
| WO | WO 10/126888 | 11/2010 |
| WO | WO 12/037034 | 3/2012 |
| WO | WO 12/045913 | 4/2012 |
| WO | WO 12/061662 | 5/2012 |
| WO | WO 12/151576 | 11/2012 |
| WO | WO 13/096926 | 6/2013 |
| WO | WO 14/070991 | 5/2014 |
| WO | WO 14/089269 | 6/2014 |
| WO | WO 14/149837 | 9/2014 |
| WO | WO 15/019284 | 2/2015 |
| WO | WO 15/048616 | 4/2015 |
| WO | WO 15/109049 | 7/2015 |
| WO | WO 16/089872 | 6/2016 |
| WO | WO 16/164394 | 10/2016 |
| WO | WO 17/023918 | 2/2017 |
| WO | WO 17/095904 | 6/2017 |
| WO | WO 17/151708 | 9/2017 |

(56) References Cited

FOREIGN PATENT DOCUMENTS

| WO | WO 18/031445 | 2/2018 |
|---|---|---|
| WO | WO 18/068010 | 4/2018 |
| WO | WO 18/169853 | 9/2018 |

OTHER PUBLICATIONS

Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.
Aggoune et al., "The Vascular Niche Is Involved in Regulating Leukemic Stem Cells in Murine Chronic Myelogenous Leukemia" Blood, 124(21):516, Dec. 6, 2014.
Aggoune et al., "The vascular niche is involved in regulating leukemic stem cells in murine chronic myelogenous leukemia," Proceedings of the 56th Annual Meeting of the American Society of Hematology, Abstract #516 Oral Presentation, Dec. 8, 2014, San Francisco, CA.
Natoni et al., "Multiple Myeloma Cells Express Functional E-Selectin Ligands Which Can be Inhibited Both in vitro and in vivo Leading to Prolongation of Survival in a Murine Transplant Model," Blood, Dec. 6, 2014, XP055349837, 56th Annual Meeting of the American Society of Hematology, Dec. 6-9, 2014, San Francisco, CA.
Alessandro, et al., "Role of S128R polymorphism of E-selectin in colon metastasis formation," Int. J. Cancer, 121(3): 528-535 (2007).
Ali, M., et al., "Polymers bearing sLex-mimetics are superior inhibitors of E-selectin-dependent leukocyte rolling in vivo", The FASEB Journal 18(1), (2004), 152-154.
Alousi, A., et al., "Reduced-Intensity Conditioning Allogeneic Hematopoietic Stem Cell Transplantation", Clinical Advances in Hematoloav & Oncoloav. 5(7), (2007), 560-570.
Angelini et al., "E-Selectin Antagonist GMI-1271 Shows a Favorable Safety, PK and Bleeding Profile in Phase I Studies of Healthy Volunteers," Blood, 128(22), Abstract #3826, Dec. 2, 2016.
Angelini et al., "E-selectin Antagonist GMI-1271 Shows a Favorable Safety, PK and Bleeding Profile in Phase I Studies of Healthy Volunteers," Proceedings of the 58th Annual Meeting of the American Society of Hematology, Poster Presentation, Dec. 3-6, 2016, San Francisco, CA.
Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.
Aref et al., "L and E Selectins in Acute Myeloid Leukemia: Expression, Clinical Relevance and Relation to Patient Outcome," Hematology, 7(2), 83-87, 2002.
Arshad, S. et al., "Primary prevention of asthma and atopy during childhood by allergen avoidance in infacny: a randomised controlled study," Thorax., 58:489-493 (2003).
Arshad, S. et al., "Primary prevention of asthma and allergy," J. Allergy Clin. Immunol., 116: 3-14 (2005).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.
Azab et al., "P-selectin Glycoprotein Ligand Regulates the Interaction of Multiple Myeloma Cells with the Bone Marrow Microenvironment", Blood, 119(6),1468-1478, Nov. 16, 2011.
Azab et al., "Role of Selectins in the Pathogenesis of Multiple Myeloma", J Clin Oncol, 27(15s):Absrt 11103, 2009.
Azab et al, "Role of Selectins in the Pathogenesis of Multiple Myeloma", ASCO Annual Meeting 2009, Poster #11103, May 2009.
Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.
Banteli, R. et al., "Potent E-Selectin Antagonists," Helvetica Chimica Acta 83(11): 2893-2907, 2000.

Banteli et al., "Synthesis of sialyl lewisx mimics. Modifications of the 6-position of galactose," Bioorganic & Medicinal Chemistry Letters, 11(4): 459-462 (2001).
Barasch et al., "Palifermin for Management of Treatment-Induced Oral Mucositis in Cancer Patients", Biologics: Targets & Therapy, 3:111-116, 2009.
Barnes, P. et al., "How do corticosteroids work in asthma?" Ann. Intern. Med., 139: 359-370 (2003).
Barthel et al., "Targeting selectins and selectin ligands in inflammation and cancer," Expert Opinion Therapeutic Targets, 11(11), 1473-1491, 2007.
Bastin, R.. et al,"Salt Selection and Optimisation Procedures for Pharmaceutical New Chemical Entities" Organic Process Research & Development (2000), vol. 4, pp. 427-435.
Bedard et al., "Expert Opinion: Selectin Inhibitors: A Patent Review," Rights Link, 20(6):781-793, 2010.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Bennett, C. F., et al., "Inhibition of Endothelial Cell Adhesion Molecule Expression with Antisense Oligonucleotides", Journal of Immunoloav. 152(7), (1994), 3530-3540.
Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Berger et al., "Adoptive transfer of effector CD8+ T cells derived from central memory cells establishes persistent T cell memory in primates." J. Clin. Invest. 118(1):294-305 (2008).
Bevilacqua, et al., "Endothelial-leukocyte adhesion molecules in human disease," Ann. Rev. Med., 45: 361-378 (1994).
Bhaskar, V. et al. "E-selectin Up-regulation Allows for Targeted Drug Delivery in Prostrate Cancer," Cancer Research, 63: 6387-6394 (Oct. 2003).
Bird et al., "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academv of Sciences. 628, (1991), 126-139.
Borsig et al., "Synergistic effects of L- and P-selectin in facilitating tumor metastasis can involve non-mucin ligands and implicate leukocytes ad enhancers of metastasis," Proceedings of the National Academy of Sciences, 99(4), 2193-2198, 2002.
Bowen et al., "Characterization of a Human Homologue of the Murine Peripheral Lymph Node Homing Receptor," Journal of Cell Biology, 109:421-427, 1989.
Bradford, G. B., et al., "Quiescence, cycling, and turnover in the primitive hematopoietic stem cell compartment", Experimental Hematoloav. 25, (1997), 445-453.

(56) References Cited

OTHER PUBLICATIONS

Brandley et al., "Carbohydrate Ligands of LEC Cell Adhesion Molecules," Cell, 63:861-863, 1990.
Breems et al., "Prognostic Index for Adult Patients With Acute Myeloid Leukemia in First Relapse," Journal of Clinical Oncology, 23(9(), 1969-1978, 2005.
Bridger, GJ et al. "Synthesis and Structure—Activity Relationships of Phenylenebis(methylene)-Linked Bis-Tetraazamacrocycles That Inhibit HIV Replication. Effects of Macrocyclic Ring Size and Substituents on the Aromatic Linker," J. Med. Chem., 38: 366-378 (1995).
Brodt et al., "Liver endothelial E-selectin mediates carcinoma cell adhesion and promotes liver metastasis," Int. J. Cancer, 71(4): 612-619 (1997).
Broquet et al., "Effect of Desipramine on a Glycoprotein Sialyltransferase Activity in C6 Cultured Glioma Cells," J. Neurochem., 54:388-394, 1990.
Burkhardt, K., et al., "The Significance of Adhesion Molecules in Nephrology", Artificial Oraans 20(5), (1996), 433-436.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of 3-Cyclohexene-l-carboxylic Acid," Acta Chemica Scandivavica, 24(8):2693-2698, 1970.
Chang et al., "Effects of Pan-Selectin Antagonist GMI-1070 on the Treatment of Vaso-Occlusion in Sickle Cell Mice", Blood, 112(11), Abstract #535, Nov. 2008.
Chang, J. et al. "GMI-1070, a novel pan-selectin antagonist, reverses acute vascular occlusions in sickle cell mice," Blood, 116(10): 1779-1786 (Sep. 2010).
Chase et al., "E-Selectin Ligands as Mechanosensitive Receptors on Neutrophils in Health and Disease", Annals of Biomedical Engineering, 40(4), pp. 849-899, Apr. 2012.
Chemical Abstracts (STN), Accession No. 1997:584307, Jul. 8, 1997.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML," Proceedings of the 54th Annual Meeting of the American Society of Hematology, Abstract #4092, Poster Presentation, Dec. 10, 2012, San Diego, CA.
Chien et al., "Adhesion of Acute Myeloid Leukemia Blasts to E-Selectin in the Vascular Niche Enhances Their Survival by Mechanisms Such as Wnt Activation", Blood, 122(21):61, Nov. 15, 2013.
Chien et al., "579 Novel Dual E-Selectin-CXCR4 Inhibitors Mobilize Human Acute Myeloid Leukemia (AML) Cells in the NODscid IL2Rγc-/- Xenograft and Confer Susceptibility to Cytarabine," Blood, 118(21) Abstract #579, Oral, Nov. 18, 2011.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 10, 2012.
Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.
Childs et al., "High-molecular-weight glycoproteins are the major carriers of the carbohydrate differentiation antigens I, I and SSEA-1 of mouse teratocarcinoma cells," Biochem. J., 215:491-503 (1983).
Choi, S. et al., "Synthetic Multivalent Molecules: Concepts and Biomedical Applications," Wiley-Interscience, p. xxi-xxvi, 1-17, 2004.
Christianson, S.W. et al., "Enhanced Human CD4+ T Cell Engraftment in β2-Microglobulin-Deficient NOD-scid Mice," The Journal of Immunology, 158:3578-3586 (1997).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.
Cottler-Fox, M.H. et al., "Stem Cell Mobilization," Amer. Sci. Hematology, 419-437, (2003).
Crawford et al., "AMD070, a CXCR4 Chemokine Receptor Antagonist: Practical Large-Scale Laboratory Synthesis," Org. Process Res. Devel. 12:823-830, 2008.
Cumpstey, I. et al. "C2-Symmetrical Thiodigalactoside Bis-Benzamido Derivatives as High-Affinity Inhibitors of Galectin-3: Efficient Lectin Inhibition through Double Arginine-Arene Interactions," Angew Chem., 117:5240-5242 (2005).
Dagia, Nilesh et al., "G-CSF induces E-selecting ligand expression on human myeloid cells," Nature Medicine, 12(10): 1185-90, Oct. 1, 2006.
Daoudii, Jean-Michel et al., "New bicyclam-GalCer analogue conjugates: synthesis and in vitro anti-HIV activity," Bioorg. & Med. Chem. Letters 14:495-498, 2004.
Datta et al., "Isolation and purification of trehalose 6-mono- and 6,6'-di-corynomycolates from Cornyebacterium matruchotii. Structural characterization of .sup.1H NMR," Carbohydrate Research 245: 151-158, 1993.
De Castro et al., "Effects of GMI-1070, a Pan-Selectin Inhibitor, On Pain Intensity and Opioid Utilization in Sickle Cell Disease", Blood, 122(21):775, Nov. 15, 2013.
De Clercq, Erik, "The bicyclam AMD3100 story," Nat. Rev. Drug Disc. 2:581-587, Jul. 2003.
DeAngelo, "A Phase I/II Study of GMI-1271, a Novel ESelectin Antagonist, in Combination with Induction Chemotherapy in Relapsed/ Refractory and Elderly Previously Untreated Acute Myeloid Leukemia; Results to Date," Blood, 128(22), Abstract #4049, Dec. 2, 2016.
DeAngelo et al. "GMI-1271, a novel E-selectin antagonist, in combination with chemotherapy in relapsed/refractory AML", Journal of Clinical Oncology, vol. 35, No. 15, suppl, May 20, 2017, p. 2520.
Definition of allogenic. Medline Plus—Merriam-Webster Medical Dictionary (last accessed Jun. 3, 2013).
Definition of syngeneic. Medline Plus—Merriam-Webster Medical Dictionary (last accessed Jun. 3, 2013).
Definition of xenogeneic. Medline Plus—Merriam-Webster Medical Dictionary (last accessed Jun. 3, 2013).
Demain et al. "Natural products for cancer chemotherapy," Microbio. Biotechnol. 4(6): 687-699, 2011.
Devata et al., First in Human Phase 1 Single Dose Escalation Studies of the E-Selectin Antagonist GMI-1271 Show a Favorable Safety, Pharmacokinetic, and Biomarker Profile, Proceedings of the 57th Annual Meeting of the American Society of Hematology, Abstract #1004, Poster Presentation, Dec. 5, 2015, Orlando, FL.
Devata et al., "First in Human Phase 1 Single Dose Escalation Studies of the E-Selectin Antagonist GMI-1271 Show a Favorable Safety, Pharmacokinetic, and Biomarker Profile," Blood, 126(23), Abstract #1004, Dec. 3, 2015.

(56) References Cited

OTHER PUBLICATIONS

Devereux, J., et al., "A comprehensive set of sequence analysis programs for the VAX", Nucleic Acids Research 12(1), (1984), 387-395.
Devine, "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Deweerdt, "Animal models: Towards a myeloma mouse," Nature, 480 (7377): S38-39 (2011).
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.
Diaz-Ricart et al., "rPSGL-Ig" Drugs of the Future 27(4):346 (2002).
Dimasi et al., "Expression, crystallization and preliminary crystallographic analysis of the extracellular IgV-like domain of the human natural killer cell inhibitory receptor p75/AIRM1," Acta Crystallographica Section D, Biological Crystallography, 59(Pt 10), 1856-1858, 2003.
Dimasi et al., "Structure of the saccharide-binding domain of the human natural killer cell inhibitory receptor p75/AIR1. Erratum," Acta Crystallographica Section D, Biological Crystallography, 60(Pt 2), Erratta, 401-403, 2004.
Dittmar et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz et al., "Safe Use of the CSCR4 Inhibitor ALX40-4C in Humans," AIDS Research and Human Retroviruses 17(6):475-486, 2001.
Duijvestijn et al., "High Endothelial Differentiation in Human Lymphoid and Inflammatory Tissues Defined by Monoclonal Antibody HECA-452," Am. J. Path. 130:147-155, 1988.
Dupre et al., "Glycomimetic Selectin Inhibitors: (.alpha.-D-Mannopyranosyloxy)methylbiphenyls," Bioorganic & Medicinal Chemistry Letters 6(5): 569-572, 1996.
Dutta et al "E-selectin inhibition mitigates splenic HSC activation and myelopoiesis in hypercholesterolemic mice with myocardial infarction highlights" Arteriosclerosis, Thrombosis, and Vascular Biology 36(9):1802-08 (2016).
Dykewicz, "Summary of the Guidelines for Preventing Opportunistic Infections among Hematopoietic Stem Cell Transplant Recipients," Clin. Infectious Diseases, 33:139-144, Jul. 15, 2001.
Edgington, "How Sweet It Is: Selectin-Mediating Drugs," Biotechnology 10: 383-389, 1992.
Edwards, "Generally Applicable, Convenient Solid-Phase Synthesis and Receptor Affinities of Octreotide Analogs," J. Med. Chem. 37:3749-3757, 1994.
Egberink et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Egger et al. "Nanomolar E-Selectin Antagonists with Prolonged Half-Lives by a Fragment-Based Approach," JACS, 135(26): 9820-9828 (Jul. 2013).
Embury et al., "The contribution of endothelial cell P-selectin to the microvascular flow of mouse sickle erythrocytes in vivo," Blood 104(10):3378-3385, Nov. 15, 2004.
English Abstract for DE 2434953, Feb. 6, 1975.
English Abstract for JP 9-176047, published Jul. 8, 1997.
English Abstract for JP 2002-520323, published Jul. 9, 2002/.
English Abstract for WO 96/20204, published Jul. 4, 1996.
English Translation of JP 06-0306092, dated Nov. 1, 1994.
English Translation of JP 2004-518704, dated Jun. 24, 2004.
Ernst et al., "Design and Synthesis of E-Selectin Antagonists," Chimia 55:268-274, 2001.
Ernst et al., "From carbohydrate leads to glycomimetic drugs," Nature Reviews 8:661-677, Aug. 2009.
Ernst, "Substrate and donor specificity of glycosyl transferases," Glycoconjugate Journal 16: 161-170, 1999.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a Potent E-selectin Antagonist (GMI-1271) as a Potential Therapeutic for Treating Breast Cancer Metastasis to the Lung and Bone", Cancer Res, Abstract #4039, Oct. 1, 2014.
Faber et al., "The Many Facets of SDF-1a, CXCR4 Agonists and Antagonists on Hematopoietic Progenitor Cells," J. Biomed. & Biotech. Article ID 26065:1-10, 2007.
Faderl et al., "Clofarabine Plus Cytarabine Compared With Cytarabine Alone in Older Patients With Relapsed or Refractory Acute Myelogenous Leukemia: Results From the Classic I Trial," Journal of Clinical Oncology, 30(20), 2492-2499, 2012.
Feletou, M. et al., "Endothelial dysfunction: a multifaceted disorder," Am. J. Physiol. Heart Circ. Physiol., 291: H985-H1002 (2006).
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Frenette, Paul S. et al., "Sulfated Glycans Induce Rapid Hematopoietic Progenitor Cell Mobilization: Evidence for Selectin-Dependent and Independent Mechanisms," Blood, 96:2460-2468, (2000).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocyctes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).

(56) References Cited

OTHER PUBLICATIONS

Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate,"Arkivoc, (vi): 224-223 (2002).

Ghobrial, IM, "Myeloma as a model for the process of metastasis: implications for therapy," 120(1): 20-30 (2012).

Gilboa-Gardner, N. et al., "A new mitogenic D-galactosephilic lectin isolated from seeds of the coral-tree *Erythrina corallodendron*. Comparison with *Glycine max* (soybean) and Pseudomonas aeruginosa lectins," Canadian Journal of Biochemistry, 59(5):315-320 (1981).

Goodman and Gillman's, "Pharmacological Basis of Therapeutics," 10th edition, p. 54 (2001).

Gooi et al., "Stage-specific embryonic antigen involves alpha 1-3 fucosylated type 2 blood group chains," Nature 292:156-158, 1981.

Gout, et al., "Selectins and selectin ligands in extravasation of cancer cells and organ selectivity of metastasis," Clin. Exp. Metastasis, 25(4): 335-344 (2008).

Gravina et al., "Abstract 428: Dual E-selectin and CXCR4 inhibition reduces tumor growth and increases the sensitivity to docetaxel in experimental bone metastases of prostate cancer," Cancer Research, 75(15 Supplemental), 428-429, Aug. 2, 2015.

Gravina et al., "Abstract 428: Dual E-selectin and CXCR4 inhibition reduces tumor growth and increases the sensitivity to docetaxel in experimental bone metastases of prostate cancer," Proceedings of the 106$^{th}$ Annual Meeting of the American Association for Cancer Research, Abstract #428, Apr. 18-22, 2015, Philadelphia, PA.

Griciuc et al., "Alzheimer's Disease Risk Gene CD33 Inhibits Microglial Uptake of Amyloid Beta," Neuron, 78(4), 631-643, May 22, 2013.

Guha et al., "Cod glycopeptide with picomolar affinity to galectin-3 suppresses T-cell apoptosis and prostate cancer metastasis," Proceedings of the National Academy of Science, 110(13), 5052-5057, 2013.

Hakomori, "Aberrant Glycosylation in Cancer Cell Membranes as Focused on Glycolipids: Overview and Perspectives," Cancer Res. 45:2405-2414, 1985.

Hakomori et al., "Novel Fucolipids Accumulating in Human Adenocarcinoma. I. Glycolipids With Di- or Trifucosylated Type 2 Chain," J. Biol. Chem. 259(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.

Halloran et al., "Ley/H: An endothelial-selective cytokine-inducible angiogenic mediator," Journal of Immunology, 164(9): 4868-4877 (May 1, 2000).

Hamamoto et al., "Inhibition of Dextram Sulphat Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clinical ExperimentalImmunoloqv, 117, (1999), 462-468.

Handa et al., "Selectin GMP-140 (CD62; PADGEM) Binds to Sialosyl-Le$^a$ and Sialosyl-Le$^x$, and Sulfated Glycans Modulate this Binding," Biochemical and Biophysical Research Communication 181(3):1223-1230, 1991.

Handschel et al., "Irradiation induces increase of adhesion molecules and accumulation of beta2-integrin-expressing cells in humans" International Journal of Radiation Oncology, Biology, Physics 45(2): 475-481 (1999).

Hansson et al., "Biosynthesis of the Cancer-associated Sialyl-Le.sup.a Antigen," Journal of Biological Chemistry 260(16):9388-9392, 1985.

Harlan, "Introduction-anti-adhesion therapy in sickle cell disease," Blood 95:365-367, 2000.

Hasegawa et al., "Synthesis of deoxy-L-fucose-containing sialyl Lewis X ganglioside analogues," Carbohydrate Research 257: 67-80, 1994.

Hasegawa et al., "Synthesis of sialyl Lewis X ganglioside analogues containing modified L-fucose residues," Carbohydrate Research 274: 165-181, 1995.

Hayashi et al., "Increased Level of Soluble E-Selectin in the Serum from Patients with Idiopathic Pulmonary Fibrosis," Inflammation, 28(1), 1-5, 2004.

Hebbar et al., "E-selectin gene S128R polymorphism is associated with poor prognosis in patients with stage II or III colorectal cancer," European Journal of Cancer, 45, 1871-1876, 2009.

Hebbel, P.R., "Blockade of Adhesion of Sickle Cells to Endothelium by Monoclonal Antibodies," The New England Journal of Medicine 342:1910-1912, Jun. 22, 2000.

Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.

Hickey et al., "Leukocyte-Endothelial Cell Interactions Are enhanced in Dermal Postcapillary Venules of MRL/fas$^{lpr}$ (Luplus-Prone) Mice: Roles of P- and E-Selectin," The Journal of Immunology, 168, 4728-4736, 2002.

Hiddemann et al., "Management of Acute Myeloid Leukemia in Elderly Patients," Journal of Clinical Oncology, 17(11), 3569-3576, 1999.

Hilal et al., "Electronic structure of orotic acid I. Geometry, conformational preference and tautomerism:, Journal of Molecular Structure (Theochem)" 685 (2004) 35-42.

Hilgenbrink. et al., "Folate receptor-mediated drug targeting: from therapeutics to diagnostics," J. Pharm. Sci., 94(10): 2135-2146 (2005).

Holgate, ST et al., "Epithelium dysfunction in asthma," Current Reviews of Allergy and Clinical Immunology, 120: 1233-1234 (2007).

Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

Hong, P. W.-P. et al., "Identification of the Optimal DC-Sign Binding Site on Human Immunodeficiency Virus Type 1 gp120," Journal of Virology 18(15):8325-8336, Aug. 2007.

Horacek et al., "Multi-analytical evaluation of serum levels of cytokines and adhesion molecules in patients treated for acute myeloid leukemia using biochip array technology," Biomed Pap Med Fac Univ Palacky Olomouc, Czech Repub., 157(4), 277-279, Dec. 2013.

Horiya et al., "Recent strategies targeting HIV glycans in vaccine design," Nature Chemical Biology, 10,990-999, 2014.

Huang et al., "Postischemic Cerebrovascular E-Selectin Expression Mediates Tissue Injury in Murine Stroke," Stroke, 31, 3047-3053, 2000.

Huse et al., "Generation of a Large Combinatorial Library of the Immunoglobulin Repertoire in Phage Lambda," Science 246:1275-1281, 1989.

Huwe, C. M. et al., "Design, Synthesis and Biological Evaluation of Aryl-substituted Sialyl Lewis X Mimetics Prepared via Cross-metathesis of C-Fucopeptides," Biological & Medicinal Chemistry 7:773-788, 1999.

Hynes, R., "Integrins: A Family of Cell Surface Receptors," Cell 48:549-554, 1987.

Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.

International Search Report and Written Opinion for PCT/US2019/020574 dated Aug. 8, 2019.

Inwald, D. P. et al, "Platelet and leucocyte activation in childhood sickle cell disease: association with nocturnal hypoxaemia," British Journal of Haematologyl 11:474-481, Nov. 2000.

Ishikawa, F. et al., "Chemotherapy-resistant human AML stem cells home to and engraft within the bone-marrow endosteal region," Nature Biotechnology 25(11):1315-1321, Nov. 2007.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.

(56) References Cited

OTHER PUBLICATIONS

Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Jiang et al., "CD33 in Alzheimer's Disease," Molecular Neurobiology, 46, 529-535, 2014.
Jubeli et al., "E-selectin as a target for drug delivery and molecular imaging," Journal of controlled Release, 158, 194-206, 2012.
Juliusson et al., "Age and acute myeloid leukemia: real world data n decision to treat and outcomes from the Swedish Acute Leukemia Registry," Blood, 113, 4170-4187, 2009.
Kaila, N. et al., "β-C-Mannosides as Selectin Inhibitors," Journal of Medicinal Chemistry 45(8): 1563-1566, 2002.
Kaila, N. et al., "Design and synthesis of sialyl Lewis(x) mimics as E- and P-selectin inhibitors," Med Res Rev 22(6):566-601, Nov. 2002.
Kannagi, R. et al. "Carbohydrate-mediated cell adhesion in cancer metastasis and angiogenesis," Cancer Sci., 95(5): 377-384 (2004).
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Kansas, G., "Selectins and Their Ligands: Current Concepts and Controversies," Blood, 88(9):3259-3287 (1996).
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Katayama, Y., et al., "CD 44 is a physiological E-selectin ligand on neutrophils", J. Exp. Med. 201(8), (2005), 1183-1189.
Katayama, Y. et al., "PSGL-1 Participates in E-Selectin-Mediated Progenitor Homing to Bone Marrow: Evidence for Cooperation Between E-Selectin Ligands and a4 Integrin," Blood, 102:2060-2067, (2003).
Kaul, D.K. et al., "Hypoxia/reoxygenation causes inflammatory response in transgenic sickle mice but not in normal mice," The Journal of Clinical Investigation 106(3):411-420, Aug. 2000.
Kayser, S. et al., "Advances in targeted therapy for acute myeloid leukemia", British Journal of Haematology, 180(4):484-500 (2018).
Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Kiel, M. J., et al., "SLAM Family Receptors Distinguish Hematopoietic Stem and Progenitor Cells and Reveal Endothelial Niches for Stem Cells" Cell 121 (7) (2006}, 11 09-1121.
Kilgore et al., "Reducation of myocardial infarct size in vivo by carbohydrate-based glycomimetics" Journal of Pharmacology and Experimental Therapeutics, American Society for Pharmacology and Experimental Therapeutics, 284(1):427-435 (1998).
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.

Kitagawa et al., "Immunoaffinity Isolation of a Sialyl-Le$^a$ Oligosaccharide from Human Milk," J. Biochem. 104:591-594, 1988.
Klyosov et al., "Galectins in Disease and Potential Therapeutic Approaches," in Galectins and Disease Implications for Targeted Therapeutics, American Chemical Society, Washington, DC, Chapter 1, pp. 3-43, 2012.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Kobayashi et al., "Cimetidine Inhibits Cancer Cell Adhesion to Endothelial Cells and Prevents Metastasis by Blocking E-selectin Expression," Cancer Research, 60, 3978-3984, 2000.
Koch, Alisa E et al., "Angiogenesis mediated by soluble forms of E-selectin and vascular cell adhesion molecule-1," Nature, 376(6540): 517-519 (1995).
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Kogan, T.P. et al., "Novel Synthetic Inhibitors of Selectin-Mediated Cell Adhesion: Synthesis of 1,6-Bis[3-(3-carboxymethylphenyl)-r-(2-.alpha.-.sub.D-monnopyranosyloxy)p-henyl]hexane (TBC1269)," J Med. Chem 41:1099-1111, 1998.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38:4976-4984, Dec. 22, 1995.
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kohler et al., "Continuous cultures of fused cells secreting antibody of predefined specificity," Nature 256:495-497, 1975.
Kohler et al., "Derivation of specific antibody-producing tissue culture and tumor lines by cell fusion," Eur. J. Immunol. 6:511-519, 1976.
Kojima et al., "Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb et al., "Development of Tool for the Design of Selectin Antagonists," Chem. Eur. J. 3(10):1571-1578, 1997.
Kolb et al., "Recent progress in the glycodrug area," Pure & Applied Chemistry 69(9):1879-1884, 1997.
Komrokji et al., "The Colony-Stimulating Factors: Use to Prevent and Treat Neutropenia and Its Complications," Expert Opin.Biol. Ther., 4:1897-1910, (2004).
Koprowski et al., "Colorectal Carcinoma Antigens Detected by Hybridoma Antibodies," Somatic Cell Genetics 5(6):957-972, 1979.
Kulidjian et al., "Differential role of E-seletin and P-selectin in T lymphocyte migration to cutaneous inflammatory reactions induced by cytokines," International Immunology, 14(7), 751-760, 2002.
Kuuliala et al., "Circulating soluble E-selectin in early rheumatoid arthritis: a prospective five year study," Annals of Rheumatic Diseases, 61, 242-246, 2002.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.
Kyriakides et al., Surgery, 128(2):327-31, Aug. 2000.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.

(56) References Cited

OTHER PUBLICATIONS

Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.
Lee et al., "A new method of sequencing linear oligosaccharides on gels using charged, fluorescent coniugates" Carbohydrate Research, vol. 214, 1991, pp. 155-168, XP000226749.
Lemoli et al., "Hematopoietic stem cell mobilization," Haematologica, 93 (3): 321-324 (2008).
Leppla, S H et al., "Anthrax Toxin Fusion Proteins for Intracellular Delivery of Macromolecules," Journal of Applied Microbiology., 87(2): p. 284 (Aug. 1, 1999).
Ley, K. et al., "Selectins in T-cell Recruitment to Non-Lymphoid Tissues and Sites of Inflammation," Nature Reviews, 4: 1-11 (May 2004).
Ley, K., "The role of selectins in inflammation and disease," Trends in Molecular Medicine, 9(6): 263-268 (Jun. 2003).
Li et al., "Hematopoietic-Derived Galectin-3 Causes Cellular and Systemic Insulin Resistance," Cell, 167, 973-984, 2016.
Li et al., "Increased CSF E-Selectin in Clinical Alzheimer's Disease without Altered CSF $A\beta_{42}$ and Tau," Journal of Alzheimer's Disease, 47, 883-887, 2015.
Li, B., et al., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.
Liang et al., "Clinicopathological and prognostic significance of sialyl Lewis X overexpression in patients with cancer: a meta-analysis," Onco Targets and Therapy, 9, 3113-3125, 2016.
Lindenberg et al., "Carbohydrate binding properties of mouse embryos," J. Reprod. Fert. 89:431-439, 1990.
Lipartiti et al., "Monosialoganglioside GM1 Reduces NMDA Neurotoxicity in Neonatal Rat Brain," Experimental Neurology 113:301-305, 1991.
Liu et al., "Altering the Specificity of the Antibody Response to HIV gp120 with a Glycoconjugate Antigen," ACS Chemical Biology, 11, 1702-1709, 2016.
Liu et al., "Broadly Neutralizing Antibody-Guided Carbohydrate-Based HIV Vaccine Design: Challenges and Opportunities," ChemMedChem, 11, 357-362, 2016.
Llmer et al., "Cell surface galectin-3 defines a subset of chemoresistant gastrointestinal tumor-initiating cancer cells with heightened stem cell characteristics," Cell Death and Disease, 7, e2337, 1-9, 2016.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al., "ELAM-1-Dependent Cell Adhesion to Vascular Endothelium Determined by a Transfected Human Fucosyltransferase cDNA," Cell 63:475-484, 1990.
Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani et al., "Glycomimetic Drugs—A New Source of Therapeutic Opportunities," Discovery Medicine, 8(43), 247-252, 2009.
Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.
Magnani, "The Discovery, Biology, and Drug Development of Sialyl Le$^a$ and Sialyl Le$^x$", Archives of Biochemistry and Biophysics, 426:122-131, May 8, 2004.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.
Maly, P., et al., "The a(1,3)Fucosyltransferase Fuc-TVII Controls Leukocyte Trafficking through an Essential Role in L-, E-, and P-selection Ligand Biosynthesis", Cell. 86(4), It 1996), 643-653.
Mann, AP et al., "Identification of Thioaptamer Ligand against E-Selectin: Potential Application for Inflamed Vasculature Targeting," PLoS One, 5(9): 1-11 (Sep. 2010).
Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.
Matsui, N. M. et al., "Heparin inhibits the flow adhesion of sickle red blood cells to Pselectin," Blood 100(10):3790-3796, Nov. 15, 2002.
Matsui, N. M. et al., "The Novel Adhesion of Erythrocytes to P-Selectin in Sickle Cell Disease," Blood 96(11) Pt. 1:600a, Abstract #2575, Nov. 16, 2000.
Matsui, N. M.et al., "P-selectin mediates the adhesion of sickle erythrocytes to the endothelium," Blood 98(6):1955-1962, Sep. 15, 2001.
Mauch, P., et al., "Hematopoietic Stem Cell Compartment: Acute and Late Effects of Radiation Therapy and Chemotherapy", Int. J. Radiation Oncology Biol. Phys . . . 31(5), 1995), 1319-1339.
Mccavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.
Mccavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.
Mcever et al., "Leukocyte trafficking mediated by selectin-carbohydrate interactions," J. Biol. Chem., 270 (19): 11025-11028 (1995).
Mckenzie et al., "Low rhodamine 123 retention identifies long-term human hematopoietic stem cells with the Lin-CD34+CD38-population", Blood. 109, (2007), 543-545.
Mclean et al., "Effects of a small molecule inhibitor of ICAM-1 and E-selectin expression on colonic inflammatory hyperalgesia and colitis" Digestive Disease 2003, Orlando FL, May 2003, abstract.
Menendez et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.
Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).
Mitsiades, et al., "Preclinical studies in support of defibrotide for the treatment of multiple myeloma and other neoplasias," Clin. Cancer Res., 15 (4): 1210-1221 (2009).
Moore et al., "Evolution of an HIV Glycan-Dependent Broadly Neutralizing Antibody Epitope Through Immune Escape," Nature Medicine doi:10.1038/nm.2985 pp. 1-6, Oct. 2012.
Moore, "Waking Up HSCs: A new Role for E-Selectin," Nat. Med., 18:16131614, (2012).

(56) References Cited

OTHER PUBLICATIONS

Mosley et al., "Recent Patents Regarding the Discovery of Small Molecule CXCR4 Antagonists," Expert Opin. Ther. Patents 19(1):23-38, 2009.
Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.
Mulligan et al., "Selection for animal cells that express the *Escherichia coli* gene coding for xanthine-gunine phosphoribosyltransferase," Proc. Natl. Acad. Sci. USA 78:2072-2076, 1981.
Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.
Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.
Myers et al., "Pan-Selectin Antagonist, GMI-1070 Decreases Venous Thrombosis in a Mouse Model", Blood, 118, Abstract #3273, Nov. 2011.
Myers Jr. et al., "E-Selectin Inhibitor GMI-1271 Works in Combination with Low-Molecular Weight Heparin to Decrease Venous Thrombosis and Bleeding Risk in a Mouse Model," Proceedings of the 56$^{th}$ Annual Meeting of the American Society of Hematology, Abstract #593 Oral Presentation on Dec. 8, 2014, San Francisco, CA.
Myers JR. et al., "Novel E-Selectin Antagonist GMI-1271 Decreases Venous Thrombosis without Increased Bleeding Potential in a Mouse Model," Blood, 120(21), Abstract #3422, Nov. 16, 2012.
Myers JR. et al., "Novel E-Selectin Antagonist GMI-1271 Decreases Venous Thrombosis without Increased Bleeding Potential in a Mouse Model," Proceedings of the 54$^{th}$ Annual Meeting of the American Society of Hematology, Abstract #3422 Poster Presentation on Dec. 10, 2012, Atlanta, GA.
Nagel, R. L., "A Knockout of a Transgenic Mouse-Animal Models of Sickle Cell Anemia," The New England Journal of Medicine 339:194-195, Jul. 16, 1998.
Narita, T. et al., "Corticosteroids and medroxyprogesterone acetate inhibit the induction of breast cancer cells," Anticancer Research, 15(6B): 2523-2527 (1995)—Abstract.
Narumi, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).
Natarajan, M.M. et al., "Adhesion of sickle red blood cells and damage to interleukinlbeta stimulated endothelial cells under flow in vitro," Blood 87:4845-4852, 1996.
Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Blood, 126(23), Abstract #1805, Dec. 3, 2015.
Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Proceedings of the 57$^{th}$ Annual Meeting of the American Society of Hematology, Abstract #1805 Poster Presentation on Dec. 5, 2015 in Orlando, FL.
Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.
Natoni et al., Multiple Myeloma Cells Express Functional E-Selectin Ligands Which Can be Inhibited Both in vitro and in vivo Leading to Prolongation of Survival in a Murine Transplant Model, Proceedings of the 56$^{th}$ Annual Meeting of the American Society of Hematology, Abstract #4718 Poster Presentation on Dec. 8, 2014 in San Francisco, CA.
Newlaczyl et al., "Galectin-3—A jack-of-all-trades in cancer," Cancer Letters, 313, 123-128, 2011.

Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).
Nicolaou et al., "Total Synthesis of the Tumor-Associated Le$^x$ Family of Glycosphingolipids," J. Amer. Chem. Soc. 112:3693-3695, 1990.
Noguchi, M. et al. "A minor E-selectin ligand, CD65, is critical for extravascular infiltration of acute myeloid leukemia cells," Leukemia Research, 25: 847-853 (2001).
Norman et al., "Sialyl Lewisx(sLex) and an sLex Mimetic, CGP69669A, Disrupt E-Selectin-Dependent Leukocyte Rolling In Vivo," Blood , 91(2):475-483 (Jan. 15, 1998).
Nudelman et al., "Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495,1986.
Nutku, E. et al., "Ligation of Siglec-8: a selective mechanism for induction of human eosinophil apoptosis," Blood, 101(12): 5014-5020 (2003).
Oancea et al., "Alleviation of Acute Drug-Induced Liver Injury Following Acetaminophen Overdose by Therapeutic Blockade of E-Selectin in Preclinical Mouse Model," Gastroenterology, 150(4), Supplement 1, S1029, Abstract #358, (no oral presentation available) New Orleans, LA, Apr. 2016.
Obermajer, N. et al., "Design, synthesis and activity evaluation of mannose-based DC-SIGN antagonists," Molecular Diversity 15:347-360, May 2011.
Orhlein, R., "Carbohydrates and Derivatives as Potential Drug Candidates with Emphasis on the Selectin and Linear-B Area," Mini Reviews in Medicinal Chemistry 1: 349-361, 2001.
Oxford Textbook of Oncology, vol. 1, published 1995 by Oxford University Press, pp. 447-453.
Palcic et al., "A Bisubstrate Analog Inhibitor for .alpha.(1.fwdarw.2)-Fucosyltransferase," J. Biol. Chem. 264:17174-17181, 1989.
Palcic et al., "Enzymic Synthesis of Oligosaccharides Terminating in the Tumor-Associated Sialyl-Lewis-a Determinant," Carbohydr. Res. 190:1-11, 1989.
Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.
Palma-Vargas, J.M. et al., "Small-Molecule Selectin Inhibitor Protects Against Liver Inflammatory Response After Ischemia and Reperfusion," J. Am. Coll. Surg. 185: 365-372, 1997.
Pamphilon et al., "Stem Cell Donation—What advice can be given to the donor?," Br. J. Haematol. 147(1):71-76, Oct. 2009, Author manuscript available at NIH Public access Aug. 1, 2012.
Patton, J. T. et al., "GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).
Peacock et al., "Emergency Department Use of Galectin-3," Critical Pathways in Cardiology, 13(2), 73-77, 2014.
Pejchal R. et al., "A Potent and Broad Neutralizing Antibody Recognizes and Penetrates the HIV Glycan Shield," Science 334:1097-1103, Nov. 2011.
Pelus, "Peripheral blood stem cell mobilization: new regimens, new cells, where do we stand," Curr. Opin. Hematol., 15(4): 285-292 (2008).

(56) References Cited

OTHER PUBLICATIONS

Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).
Pentelute, Brad L. et al., "Chemica 11-16 dissection of protein translocation through the anthrax toxin pore," Angewandte Chemie, 50(10): 2294-2296 (Mar. 1, 2011).
Perret, S. et al., "Structural basis for the interaction between human milk oligosaccharides and the bacterial lectin PA-IIL of Pseudomonas aeruginosa," Biochem. J. 389: 325-332, 2005.
Pezeshkian et al., "Leukemia Mediated Endothelial Cell Activation Modulates Leukemia Cell Susceptibility to Chemotherapy through a Positive Feedback Loop Mechanism," PLOS One, 8(4), e60823, 2013.
Phillips et al., "ELAM-1 Mediates Cell Adhesion by Recognition of a Carbohydrate Ligand, Sialyl-Le.sup.x," Science 250:1130-1132, 1990.
Picker er al., "The Neutrophil Selectin LECAM-1 Presents Carbohydrate Ligands to the Vascular Selectins ELAM-1 and GMP-140," Cell 66:921-933, 1991.
Plasterk, R. H. A., et al., "The silence of the genes", Current Opinion in Genetics and Develooment 10 (2000), 562-567.
Price et al., "Breast Cancer Cells Metastasize to Bone through E-Selectin Positive Vascular Gateways", AACR Annual Meeting 2014, Poster #4831, Apr. 9, 2014.
Price et al., "Breast cancer cells metastasize to bone through E-selectin + vascular gateways," Cancer Research, 74(19 Supplement), 4831, Sep. 20, 2014.
Price et al., "Metastatic breast cancer cell communication within a pro-dormancy bone marrow niche," Cancer Research, 75(15 Supplement), Abstract #3212, Aug. 2015.
Price et al., "Metastatic Breast Cancer Cell Communication Within a Pro-Dormancy Bone Marrow Niche," Proceedings of the 106$^{th}$ Annual Meeting of the American Association for Cancer Research, Abstract #3212, Apr. 18-22, 2015, Philadelphia, PA.
Prokazova et al., "Sialylated lactosylceramides. Possible inducers of non-specific immunosuppression and atherosclerotic lesions," European Journal of Biochemistry 172:1-6, 1988.
Purton et al., "Limiting Factors in Murine Hematopoietic Stem Cell Assays," Cell Stem Cell 1: 263-270, Sep. 2007.
Rapoport et al., "Ganglioside Binding Pattern of CD33-Related Siglecs," Bioorganic and Medicinal Chemistry Letters, 13(4), 675-678, Feb. 2003.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Ravandi et al., "Characteristics and outcome of patients with acute myeloid leukemia refractory to 1 cycle of high-dose cytarabine-based induction chemotherapy," Blood 116(26), 5818-5823, 2010.
Reina et al., "1,2-Mannobioside Mimic: Synthesis, DC-SIGN Interaction by NMR and Docking, and Antiviral Activity," ChemMedChem 2:1030-1036, 2007.
Rice et al., "An Inducible Endothelial Cell Surface Glycoprotein Mediates Melanoma Adhesion," Science 246:1303-1306, 1989.
Richert et al., "Inhibition of CXCR4 by CTCE-9908 Inhibits Breast Cancer Metastasis to Lung and Bone," Oncology Reports 21:761-767, 2009.
Roberge, J. Y., et al., "A Strategy for a Convergent Synthesis of N-Linked Glycopeptides on a Solid Support", Science 269(5221), (1995), 202-204.
Röllig et al., "Long-Term Prognosis of Acute Myeloid Leukemia According to the New Genetic Risk Classification of the European LeukemiaNet Recommendations: Evaluation of the Proposed Reporting System," Journal of Clinical Oncology, 29(20), 2758-2765, 2011.
Rood et al., "E-Selectin and Very Late Activation Antigen-r Mediate Adhesion of Hematopoietic Progenitor Cells to Bone Marrow Endothelium," Ann Hematol, 79:477-484, (2000).
Ruoslahti et al., "New Perspectives in Cell Adhesion: RGD and Integrins," Science 238:491-497, 1987.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Salameh et al., "1H-1,2,3-Triazol-1-yl thiodigalactoside derivatives as high affinity galectin-3 inhibitors," Bioorganic & Medicinal Chemistry, 18, 5367-5378, 2010.
Sanz et al., "Roflumilast inhibits leukocyte-endothelial cell interactions, expression of adhesion molecules and microvascular permeability", British Journal of Pharmacology. 152(4), (2007), 481-492.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan et al., "Exploiting the Defensive Sugars of HIV-1 for Drug and Vaccine Design," Nature 446:1038-1045, Apr. 2007.
Scanlan et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.
Scharfman et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman et al., "Recognition of Lewis x Derivatives Present on Mucins by Flagellar Components of Pseudomonas aeruginosa," Infection and Immunity 69(9): 5243-5248, Sep. 2001.
Schief et al., "Challenges for Structure-Based HIV Vaccine Design," Current Opinion in HIV and AIDS 4:431-440, 2009.
Schwizer et al. "Pre-organization of the Core Structure of E-Selectin Antagonist," Chemistry—A European Journal, 18(5): 1342-1351 (Jan. 2012).
Shamay et al., "E-selectin binding peptide-polymer-drug conjugates and their selective cytotoxicity against vascular endothelial cells," Biomaterials, 30, 6460-6468, 2009.
Shan, M. et al., "HIV-1 gp120 Mannoses Induce Immunosuppressive Responses from Dendritic Cells," PLoS Pathogens 3(11):e169 1637-1650, Nov. 2007.
Sheen-Chen et al., "Serum levels of soluble E-selectin in women with breast cancer," British Journal of Surgery, 91, 1578-1581, 2004.
Shitara et al., "Application of Anti-Sialyl Le.sup.a Monoclonal antibody, KM231, for Immunotherapy of Cancer," Anticancer Res. 11:2003-2014, 1991.
Simanek et al. "Selectin-carbohydrate interactions: from natural ligands to designed mimics", Chemical Reviews vol. 98, No. 2, pp. 833-862, Jan. 1998.
Simon et al, "Effects of Selectin Antagonist GMI-1070 on the Activation State of Leukocytes in Sickle Cell Patients not in Crisis" ASH Annual Meeting 2010, Poster #32407, Dec. 6, 2010.
Simon et al., "Inhibition of E-Selectin Inflammatory Function by the Glycomimetic GMI-1070" Blood, 118, Abstract #851, Nov. 2011.
Simon et al., "Mightier than the sickle cell (editorial)", Blood, 116(10), 1633, Sep. 9, 2010.
Singh et al., "Evaluation of a CXCR4 Antagonist in a Xenograft Mouse Model of Inflammatory Breast Cancer," Clin. Exp. Metastasis 27:233-240, Mar. 2010.
Sipkins et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.

(56) References Cited

OTHER PUBLICATIONS

Solovey et al., "Circulating Activated Endothelial Cells in Sickle Cell Anemia," The New England Journal of Medicine 337:1584-1590, Nov. 27, 1997.
Solovey et al. "Modulation of endothelial cell activation in sickle cell disease: a pilot study," Blood, 97(7): 1937-1941 (Apr. 2001).
Sprengard et al., "Synthesis and Biological Activity of Novel Sialyl-Lewis.sup.X Conjugates," Bioorganic & Medicinal Chemistry Letters 6(5): 509-514, 1996.
Stahn et al., Multivalent sialyl Lewis x ligands of definite structures as inhibitors of E-selectin mediated cell adhesion, Glycobiology, vol. 8, No. 4, 1998, pp. 311-319.
Stanley et al., "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.
Steele et al., "#4503 A Small Molecule Glycomimetic Antagonist of E-selectin (GMI-1271) Prevents Pancreatic Tumor Metastasis and Offers Improved Efficacy of Chemotherapy," Proceedings of the 105th Annual Meeting of the American Association for Cancer Research, Abstract #4503, Apr. 5-9, 2014, San Diego, CA.
Steele et al., "425 A small molecule glycomimetic antagonist of E-selectin and CXCR4 (GMI-1359) prevents pancreatic tumor metastasis and offers improved chemotherapy" Cancer Research, Aug. 2015.
Steele et al., "425 A Small Molecule Glycomimetic Antagonist of E-selectin and CXCR4 (GMI-1359) Prevents Pancreatic Tumor Metastasis and Offers Improved Chemotherapy," Proceedings of the 106th Annual Meeting of the American Association for Cancer Research, Abstract #425, Apr. 18-22, 2015, Philadelphia, PA.
Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.
Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract 4503, Oct. 1, 2014.
Steele et al., "A small molecule glycomimetic antagonist of E-selectin and CXCR4 (GMI-1359) prevents pancreatic tumor metastasis and improves chemotherapy," Cancer Research, 75(15 Supplement), 425-426, Aug. 2, 2015.
Steele et al., "A small molecule glycomimetic antagonist of E-selectin and CXCR4 (GMI-1359) delays pancreatic tumor metastasis and significantly alters the pancreatic tumor microenvironment," Proceedings of the 107th Annual Meeting of the American Association for Cancer Research, Abstract #902, Apr. 16-20, 2016, New Orleans, LA.
Steele et al., "Abstract 4503: A small molecule glycomimetic antagonist of E-selectin (GMI-1271) prevents pancreatic tumor metastasis and offers a novel treatment for improved efficacy of chemotherapy," Cancer Research, 74(19 Supplement), Abstract #4503, Oct. 2014.
Stephens et al.,"The construction of highly efficient and versatile set of mammalian expression vectors," Nucleic Acids Research. 17:7110, 1989.
Stevenson et al., "Differential metastasis inhibition by clinically relevant levels of heparins," Clin. Cancer Res. 11(19): 7003-7011 (2005).
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al. ,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.

Sudhoff et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002).
Suzuma et al., "Contribution of E-Selectin to Cellular Infiltration during Endotoxin-Induced Uveitis," Invest. Ophthalmol. Vis. Sci., 39: 1620-1630 (1998).
Svenson et al., "Coupling of Acid Labile *Salmonella* Specific Oligosaccharides to Macromolecular Carriers," J. Immunol. Meth. 25:323-335, 1979.
Symon et al., "Selectins and their Counter receptors: a bitter sweet attraction," Thorax, 51: 1155-1157 (1996).
Tabarani et al., "Mannose Hyperbranched Dendritic Polymers Interact with Clustered Organization of DC-SGIN and Inhibit gp120 Binding," FEBS Letters 580:2402-2408, Mar. 2006.
Takada et al., "Adhesion of Human Cancer Cells to Vascular Endothelium Mediated by a Carbohydrate Antigen, Sialyl Lewis A$^1$," Biochem. Biophys. Res. Commun. 179(2):713-719, 1991.
Takahashi et al., "Design and Synthesis of a Water-Soluble Taxol Analogue : Taxol-Sialyl Conjugate," Bioorg. & Med. Chem. Letters 8:113-116, 1998.
Takeichi, "Cadherins: a molecular family essential for selective cell-cell adhesion and animal morphogenesis," Trends Genet. 3(8):213-217, 1987.
Tamamura. et al., "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka et al., "Azamacrocyclic Metal Complexes as CXCR4 Antagonists," ChemMedChem, 6: 834-839 (2011).
Taniguchi et al., "Serum Levels of Galectin-3: Possible Association with Fibrosis, Aberrant Angiogenesis, and Immune Activation in Patients with Systemic Sclerosis," The Journal of Rheumatology, 39(3), 539-544, Mar. 2012.
Tedder et al., "The selectins: vascular adhesion molecules," FASEB J, 9(10): 866-73 (1995).
Tejler et al., "Fragment-based development of triazole-substituted O-galactosyl aldoximes with fragment-induced affinity and selectivity for galectin-3," Organic & Biomolecular Chemistry, 19(7), 3982-3992, 2009.
Tejler et al., "Synthesis of galactose-mimicking 1H-(1,2,3-triazol-l-yl)-mannosides as selective galectin-3 and 9N inhibitors," Carbohydrate Research, 342(12-13), 1869-1875, 2007.
Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.
Telen et al., "Randomized phase 2 study of GMI-1070 in SCD: reduction in time to resolution of vaso-occlusive events and decreased opioid use", Blood, 125(17):2656-2664, Apr. 23, 2015.
The Merck Manual of Diagnosis and Therapy, Seventeenth Edition, published 1999 by Merck Research Laboratories, pp. 397, 398, 948,949, 1916, 1979-1981.
Thoma G. et al., "A readily Available, Highly Potent E-Selectin Antagonist," Angew. Chem. Int. Ed. 40(19): 3644-3647, 2001.
Thoma, G et al., "Nanomolar E-selectin inhibitors: 700-fold potentiation of affinity by multivalent ligand presentation," Journal of the American Chemical Society, 123(41): 10113-10114 (Oct. 17, 2001).
Thoma, G. et al., "Preorganization of the Bioactive Conformation of Sialyl Lewis$^X$ Analogues Correlates with Their Affinity to E-Selectin," Angew. Chem. Int. Ed. 40(10): 1941-1945, 2001.
Thoma, G. et al., "Synthesis and biological evaluation of a potent E-selectin antagonist," J. Med. Chem. 42 (23): 4909-4913, Nov. 18, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.

(56) References Cited

OTHER PUBLICATIONS

Titz et al., "Is adamantine a suitable substituent to pre-organize the acid orientation in E-selectin antagonists?", Bioorganic & Medicinal Chemistry, 16 (2008), 1046-1056.
Titz et al., "Mimetics of Sialyl Lewis$^x$: The Pre-Organization of the Carboxylic Acid is Essential for Binding to Selectins", Chimia, 61:194-197, 2007.
Titz, A. et al., "Probing the carbohydrate recognition domain of E-selectin: The importance of the acid orientation in sLex mimetics," Bioorg. Med. Chem., 18(1): 19-27 (2010).
Todderund et al., "BMS-190394, a Selectin Inhbitor, Prevents Rat Cutaneous Inflammatory Reactions," J Pharmacal Exp Ther., 282(3):1298-304, Sep. 1997.
Toepfer et al., "Synthesis of Novel Mimetics of the Sialyl Lewis X Determinant," Tetrahedron Letters, vol. 36, No. 50, pp. 9161-9164, 1995.
Togel et al., "Administered mesenchymal stem cells protect against ischemic acute renal failure through differentiation-independent mechanisms," Am. J. Physical Renal Physiol., 289:F31-42, Jul. 2005.
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Van Der Velde et al., "Galectin-3 and sST2 in prediction of left ventricular ejection fraction after myocardial infarction," Clinica Chimica Acta, 452, 50-57, Jan. 2016.
Venkataraman et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor4 for the Inhibition of Hepatocellular Carcinoma Metastasis," A Thesis, in partial fulfillment of requirements for Ph.D. Degree at the Univ. of Hong Kong, Jun. 2008.
Waldmann et al., "Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.
Walker et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.
Wang et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang et al., "Effect of ginsenoside rg1 and rh1 on the expression of hla-dr, cd25, cd44, cd11c and e-selectin on dendritic cell," Zhongguo Mianyixue Zazhi, 23(1): 46-48 (2007)—Abstract.
Wang et al., "Galectin-3 promotes HIV-1 budding via association with Alix and Gag p6," Glycobiology, 24(11), 1022-1035, 2014.
Wang et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Ward et al., "Blocking of adhesion molecules in vivo as anti-inflammatory therapy," Immunology 1: 165-171, 1994.
Wesche et al., "Characterization of membrane translocation by anthrax protective antigen," Biochemistry, 37(45): 15737-15746 (Nov. 10, 1998).
Whisler et al., "Regulation of Lymphocyte Responses by Human Gangliosides. I. Characteristics of Inhibitory Effects and the Induction of Impaired Activation," Journal of Immunology 125(5):2106-2111, 1980.
Wicklein et al., "E- and P-Selectins Are Essential for Repopulation of Chronic Myelogenous and Chronic Eosinophilic Leukemias in a Scid Mouse Xenograft Model," PLOS One, 8(7), e70139, 2013.
Winkler et al., "Absence of E-selectin at vascular niche delays hematopoietic stem cell turn-over," Blood, 110(11):188A, Nov. 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract#564, Dec. 7, 2009.
Winkler et al., "Adhesion of E-selectin promotes growth inhibition and apoptosis of human and murine hematopoietic progenitor cells independent of PSGL-1," Blood, 103(5):1685-92, Mar. 1, 2004.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster #63045, Dec. 8, 2013.
Winkler et al., "Administration of E-Selectin Antagonist GMI-1271 Improves Survival After High-Dose Chemotherapy by Alleviating Mucositis and Accelerating Neutrophil Recovery," Blood, 122(21), Abstract #2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery," Proceedings of the 55$^{th}$ Annual Meeting of the American Society of Hematology, Abstract #2266, Poster Presentation on Dec. 9, 2013, New Orleans, LA.
Winkler et al., "Mobilisation of Reconstituting HSC Is Boosted by Synergy Between G-CSF and E-Selectin Antagonist GMI-1271", Blood, 124(21):317, Dec. 6, 2014.
Winkler et al., "Mobilisation of Reconstituting HSC Is Boosted by Synergy Between G-CSF and E-Selectin Antagonist GMI-1271," Blood, 124(21), Abstract #317, Dec. 6, 2014.
Winkler et al., "Mobilization of CD8$^+$ Central Memory T-Cells with Enhanced Reconstitution Potential in Mice by a Combination of G-CSF and GMI-1271-Mediated E-Selectin Blockade," Blood, 126(23), Abstract #512, Dec. 3, 2015.
Winkler et al., "Mobilization ofCD8+ Central Memory T-Cells with Enhanced Reconstitution Potential in Mice by a Combination of G-CSF and GMI-1271-Mediated E-Selectin Blockade," Proceedings of the 57$^{th}$ Annual Meeting of the American Society of Hematology, Abstract #512, Oral Presentation, Dec. 7, 2015, Orlando, FL.
Winkler et al., "Vascular E-Selectin Protects Leukemia Cells from Chemotherapy by Directly Activating Pro-Survival NF-Kb Signalling—Therapeutic Blockade of E-Selectin Dampens NF-Kb Activation," Blood, 128(22), Abstract #2823, Dec. 2, 2016.

(56) References Cited

OTHER PUBLICATIONS

Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Protects Acute Myeloid Leukaemia Stem Cells from Chemotherapy," Blood, 124(21), Abstract #620, Dec. 6, 2014.
Winkler et al., "Vascular Niche E-selectin Regulates Hematopoietic Stem Cell Dormancy, Self Renewal and Chemoresistance", Nature Medicine, doi:10.1038/nm2969, Oct. 21, 2012.
Winkler et al., "Vascular niche E-selectin regulates hematopoietic stem cell dormancy, self renewal and chemoresistance," Nature Medicine, 18(11), 1651-1657, 2012.
Winkler et al., "Vascular niche E-selectin regulates hemopoietic stem cell dormancy, self-renewal and chemoresistance," Nature Medicine, 18(11), 1651-1657, Supplementary Figures and Table, 2012.
Winkler, "Mobilisation of reconstituting HSC is boosted by E-selectin antagonist GMI-1271," Proceedings of the 56th Annual Meeting of the American Society of Hematology, Abstract #317, Oral Presentation on Dec. 7, 2014, San Francisco, CA.
Winkler, "Vascular bone marrow niches protect AML Leukaemia stem cells from chemotherapy," Proceedings of the 56th Annual Meeting of the American Society of Hematology, Abstract #620, Oral Presentation on Dec. 8, 2014, San Francisco, CA.
Winnard, P. et al., "Real time non-invasive imaging of receptor-ligand interactions in vivo," J. Cell. Biochem., 90: 454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Witz, "The involvement of selectins and their ligands in tumor-progression," Immunol. Lett., 104 (1-2): 89-93 (2006).
Wu et al., "Salivary Agglutinin Inhibits HIV Type 1 Infectivity through Interaction with Viral Glycoprotein 120," AIDS Research and Human Retroviruses, 19(30), 201-209, 2003.
Wu, B. et al. "Structures of the CXCR4 Chemokine GPCR with Small-Molecule and Cyclic Peptide Antagonists," Science, 330(6007): 1066-1071 (Nov. 2010).
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al., "Molecular insights and therapeutic targets for diabetic endothelial dysfunction," Circulation, 120: 1266-1286 (2009).
Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang et al., "3790 The Dual E-Selectin/CXCR4 Inhibitor, GMI-1359, Enhances Efficacy of Anti-Leukemia Chemotherapy in FLT3-ITD Mutated Acute Myeloid Leukemia," Blood, 126(23), Abstract #3790, Dec. 3, 2015.
Zhang et al., "The Dual E-selectin/CXCR4 Inhibitor, GMI-1359, Enhances Efficacy of Chemotherapy in FLT3-ITD-Mutated Acute Myeloid Leukemia," Proceedings of the 57th Annual Meeting of the American Society of Hematology, Abstract #3790, Poster Presentation, Dec. 7, 2015, Orlando, FL.
Zhang et al., "The E-selectin/CXCR4 Inhibitor GMI-1359 Effectively Mobilizes Bone Marrow Leukemia Cells and Enhances FLT3 Inhibitor Efficacy in a Murine AML Model," Proceedings of the 107th Annual Meeting of AACR, 3284, Apr. 16-20, 2016, New Orleans, LA.

Zhang, Z. et al. "CXCR4 but not CXCR7 is mainly implicated in ocular leukocyte trafficking during ovalbumin-induced acute uveitis," Experimental Eye Research, 89: 522-531 (2009).
Zhao T. et al. "Targeting human CD34+ hematopoietic stem cells with anti-CD45 x antimyosin light-chain bispecific antibody preserves cardiac function in myocardial infarction" Journal of Applied Physiology, 10(6):1793-1800 (2008).
Zheng, CX et al. "The prognostic value of preoperative serum levels of CEA, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—Abstract.
Zopf et al., "Affinity Purification of Antibodies Using Oligosaccharide-Phenethylamine Derivatives Coupled to Sepharose," Meth. Enzymol. 50:171-175, 1978.
Zuber et al., "Mouse models of human AML accurately predict chemotherapy response," Genes. Dev., 23 (7): 877-889 (2009).
Alessandro et al., "Multiple Myeloma Cells Express Functional E-Selectin Ligands Which Can be Inhibited Both in vitro and in vivo Leading to Prolongation of Survival in a Murine Transplant Model," Blood, Dec. 6, 2014, XP055349837, 56th Annual Meeting of the American Society of Hematology, Dec. 6-9, 2014, San Francisco, CA.
Antoine et al., "Expression of E-selectin ligand-1 (CFR/ESL-1) on heptatic stellate cells: Implications for leukocyte extravasation and liver metastasis," Oncology Reports, 21:357-362, 2009.
Aoki et al., "Effects of Vascular Endothelial Growth Factor and E-Selectin on Angiogenesis in the Murine Metastatic RCT Sarcoma," Tumor Biol., 2001; 22:239-246.
Bleckmann et al., "O-glycosylation pattern of CD24 from mouse brain," Biol. Chem., vol. 390, pp. 627-645, Jul. 2009.
Borentain et al., "Inhibition of E-selectin expression on the surface of endothelial cells inhibits hepatocellular carcinoma growth by preventing tumor angiogenesis," Cancer Chemother Pharmacol (2016), 77:847-856.
Chantarasrivong et al., "Synthesis and Functional Characterization of Novel Sialyl LewisX Mimic-Decorated Liposomes for E-selectin-Mediated Targeting to Inflamed Endothelial Cells," Mol. Pharmaceutics, 2017, 14, 1528-1537.
Chien et al., "E-Selectin Ligand Expression by Leukemic Blasts Is Associated with Prognosis in Patients with AML," Blood 2018. 132:1513.
Chien et al., "E-Selectin Ligand Expression by Leukemic Blasts Is Associated with Prognosis in Patients with AML," Proceedings of the 60th American Society of Hematology Annual Meeting, Poster 1513, Dec. 3, 2018.
Cossu et al., "Serum levels of vascular dysfunction markers reflect disease severity and stage in systemic sclerosis patients," Rheumatology, 2016; 55:1112-116.
Feizi et al., "Neoglycolipids: Probes of Oligosaccharide Structure, Antigenicity, and Function," Methods in Enzymology, vol. 230, 1994, pp. 484-519.
Griffioen et al., "Angiostasis as a way to improve immunotherapy," Thromb Haemost, 2009; 101:1025-1031.
Hashida et al., "High-efficacy site-directed drug delivery system using sialyl-Lewis X conjugated liposome," Experimental Eye Research 86, 2008, 138-149.
Jubeli et al., "Preparation of E-selectin-targeting nanoparticles and preliminary in vitro evaluation," International Journal of Pharmaceutics, 426(2012), 291-301.
Kannagi, "Transcriptional regulation of Expression of Carbohydrate Ligands for Cell Adhesion Molecules in the Selectin Family[a,b]," The Molecular Immunology of Complex Carbohydrates-2, edited by Albert M. Wu, Kluwer Academic/Plenum Publishers, 2001, pp. 267-278.
Kim et al., "Altered Expression of Lewis Antigen on Tissue and Erythrocytes in Gastric Cancer Patients," Yonsei Medical Journal, vol. 43, No. 4, pp. 427-434, 2002.

(56) References Cited

OTHER PUBLICATIONS

Kuznetsova et al., "Targeting liposomes loaded with melphalan prodrug to tumour vasculature via the Sialyl Lewis X selectin ligand," J. Drug Target. 2014, 22(3):242-250.

Li et al., "α1,3 Fucosyltransferase VII plays a role in colorectal carcinoma metastases by promoting the carbohydration of glycoprotein CD24," Oncology Reports, 23:1609-1617, 2010.

Magro et al., "Cutaneous lymphocyte antigen expression in benign and neoplastic cutaneous B- and T-cell lymphoid infiltrates," J. Cutan. Phathol., 2008:35:1040-1049.

Metza et al., "Venous Thrombosis and Post-Thrombotic Syndrome: From Novel Biomarkers to Biology," Methodist Debakey Cardiovasc J, 14(3), 2018, pp. 173-181.

Morikis et al., "Selectin catch-bonds mechanostransduce integrin activation and neutrophil arrest on inflamed endothelium under shear flow," Blood, Nov. 9, 2017, vol. 130, No. 19. pp. 2101-2110.

Murohara et al., "Cardioprotection by liposome-conjugated sialyl Lewis$^x$-oligosaccharide in myocardial ischaemia and reperfusion injury," Cardiovascular Research, 30(1995), 965-974.

Nonomura et al., "CD43, but not P-Selectin Glycoprotein Ligrand-1, Functions as an E-Selectin Counter-Receptor in Human Pre-B-Cell Leukemia NALL-1," Cancer Res, 2018, 68: (3), Feb. 1, 2008, pp. 790-800.

Paneghetti et al., "A novel endothelial-derived anti-inflammatory activity significantly inhibits spontaneous choroidal neovascularization in a mouse model," Vascular Cell, (2016), 8:2, pp. 1-12.

Pattillo et al., "Radiation-Guided Targeting of Combretastatin Encapsulated Immunoliposomes to Mammary Tumors," Pharmaceutical Research, vol. 26, No. 5, May 2009, pp. 1093-1100.

Porquet et al., "Survival advantages conferred to colon cancer cells by E-selectin-induced activation of the PI3K-NF$_K$B survival axis downstream of Death receptor-3," BMC Cancer, 2011, 11:285, pp. 1-12.

Prescher et al., "New Human CD22/Siglec-2 Ligands with a Triazole Glycoside," ChemBioChem, 2017, 18, 126-1225.

Price et al., "Breast Cancer Cells Metastasize to Bone through E-Selectin Positive Vascular Gateways," Proceedings of the 105$^{th}$ Annual Meeting of the AACR, 4831, Apr. 5-9, 2014, San Diego, CA.

Spivak et al., "Low-Dose Molecular Ultrasound Imaging with E-Selectin-Targeted PBCA Microbubbles," Mol. Imaging Biol., (2016), 18:180-190.

Tchinda et al., "Severe malaria in Cameronian children: correlation between plasma levels of three soluble inducible adhesion molecules and TNF-α," Acta Tropica, 102(2007), 20-28.

Trøseid et al., "Changes in serum levels of E-selectin correlate to improved glycaemic control and reduced obesity in subjects with the metabolic syndrome," Scand J Clin Lab Invest, 2005, 65:283-290.

Tsuruta et al., "Application of liposomes incorporating doxorubicin with sialyl Lewis X to prevent stenosis after rat carotid artery injury," Biomaterials, 30(2009), 118-125.

Yadav et al., "Screening of Neu5Acα(2-6)gal isomer preferences of siglecs with a sialic acid microarray," Org. Biomol. Chem., 2016, 14, 10812-10815.

Fogler, William E. et al., "Glycomimetic Antagonist of E-Selectin, GMI-1271, Enhances Therapeutic Activity of the Hypomethylating Agent, 5-Azacitidine, in the KG1 Model of AML," Blood, vol. 130, Supplement 1, Dec. 7, 2017, p. 5065.

\* cited by examiner

Compound of Formula (I) Protects Against Chemotherapy Induced Gastrointestinal Mucositis

E-selectin Ligand Binding by AML Blasts in Newly Diagnosed and Relapsed Leukemia Patients sLe$^{a/x}$ Binding by AML Blasts in Newly Diagnosed and Relapsed Leukemia Patients

Induction Protocols

MEC Induction  Day → 1 2 3 4 5 6 7 8

FAI Induction  Day → 1 2 3 4 5 6 7 8

Consolidation Protocols

METHODS FOR TREATING ACUTE MYELOID LEUKEMIA AND RELATED CONDITIONS

CROSS-REFERENCE TO RELATED APPLICATIONS

This application is a U.S. national phase entry under 35 U.S.C. § 371 from PCT International Application No. PCT/US2019/020574, filed Mar. 4, 2019, which claims priority to U.S. Provisional Application No. 62/638,569, filed Mar. 5, 2018, the contents of each of which are hereby incorporated by reference.

BACKGROUND

The present disclosure relates to methods for treating or inhibiting cancer and/or one or more related conditions comprising administering to a subject in need thereof an effective amount of at least one compound of Formula (I), prodrug thereof, and/or pharmaceutically acceptable salt of any of the foregoing.

The present disclosure provides methods for treating patients with cancers, including drug-resistant cancers, cancers with a high likelihood of relapse, cancers with accelerated disease progression, and/or cancers with reduced survival.

A number of cancers are highly treatable when treated before the cancer has moved beyond the primary site. However, often once the cancer has spread beyond the primary site, the treatment options are limited, and the survival statistics decline dramatically. For example, when colorectal cancer is detected at a local stage (i.e., confined to the colon or rectum), over 90% of those diagnosed survive more than five years. Conversely, when colorectal cancer has spread to distant sites (i.e., metastasized from the primary site to distant sites), the five-year survival rate of those diagnosed drops dramatically to only 11%.

The four most common hematological cancers are acute lymphocytic leukemia (ALL), chronic lymphocytic leukemia (CLL), chronic myelogenous leukemia (CML), and acute myelogenous leukemia (AML). Leukemias and other cancers of the blood, bone marrow, and lymphatic system affect 10 times more adults than children. AML is the most common leukemia in adults.

AML results when bone marrow begins making blasts instead of mature white blood cells. The immature blasts are unable to fight infections. AML is the most common acute leukemia, and it progresses rapidly. Left untreated, AML may lead to death in weeks or months.

Current treatments for AML include chemotherapy, including targeted chemotherapies, radiation therapy, and autologous stem cell transplantation or allogeneic stem cell transplantation. The side effects of each of these treatments are well documented. Typically, a newly diagnosed AML patient will be treated with an induction chemotherapy regimen to attempt to put the cancer in remission. Remission does not cure the patient; it merely means the disease can no longer be detected. Remission, however, is most often a temporary measure as most AML patients in remission eventually relapse. Post-remission therapies include consolidation chemotherapy (typically three to five courses of intensive chemotherapy for leukemias with good prognoses), allogenic stem cell transplantation (for higher risk leukemias and with a matched donor), and autologous stem cell transplant (when possible based on the patients underlying condition, and when a matched donor is not available).

Very few medications are available to treat relapsing AML, such as the highly toxic arsenic trioxide, which only works in AML patients with the acute promyelocytic leukemia subtype of AML. In persons with relapsing AML, the only potential cure is stem cell transplant. When stem cell transplant is not possible, immunotherapy may be attempted to extend remission as long as possible. With such limited treatment options, palliative care is often the only treatment available for relapsing AML patients. Therefore, there is a need for additional therapeutics for treating (including preventing) AML.

Myelodysplastic syndrome ("MDS") refers to a diverse group of hematopoietic stem cell ("HSC") disorders. MDS is characterized by a cellular marrow with impaired morphology and maturation (dysmyelopoiesis), peripheral blood cytopenias, and a risk of progression to acute leukemia resulting from ineffective blood cell production. (See The Merck Manual. 1999. 17:953; List, et al. The Myelodysplastic Syndromes: Biology and Implications for Management. J. Clin. Oncol. 1990. 8:1424.)

The common trait shared by MDS HSC disorders is the presence of dysplastic changes in one or more of the hematopoietic lineages, for example, dysplastic changes in the myeloid, erythroid, or megakaryocytic series. These changes result in cytopenia in one or more of the lineages. Patients afflicted with MDS may develop complications related to anemia, neutropenia (infections), and/or thrombocytopenia (bleeding). From about 10% to about 70% of patients with MDS develop acute leukemia. In the early stages of MDS, the main cause of cytopenia is increased programmed cell death (apoptosis). As the disease progresses and converts into leukemia, a proliferation of leukemic cells overwhelms the healthy marrow. The disease course differs, with some cases behaving as an indolent disease and others behaving aggressively with very short clinical courses that convert into acute forms of leukemia. The majority of people with higher risk MDS eventually experience bone marrow failure. Up to 50% of MDS patients succumb to complications, such as infection or bleeding, before progressing to AML.

The initial HSC injury can be from causes such as, but not limited to, cytotoxic chemotherapy, radiation, viral infection, chemical exposure, and genetic predisposition. Alkylating chemotherapy or radiation therapy can cause MDS, which nearly always progresses to AML in these subjects.

MDS is primarily a disease of elderly people, with the median onset in the seventh decade of life. The median age of these patients is 65 years, with ages ranging from the early third decade of life to as old as 80 years or older. However, the syndrome may occur in any age group, including the pediatric population. Patients who survive malignancy treatment with alkylating agents, with or without radiotherapy, have a high incidence of developing MDS or secondary acute leukemia. About 60-70% of patients do not have an obvious exposure or cause for MDS and are classified as primary MDS patients.

Currently U.S. Food and Drug Administration-approved drugs for the treatment of MDS are not curative, and their effect on survival is limited. They include the hypomethylating agents ("HMA") (such as azacitidine and decitabine), and lenalidomide for treating MDS with isolated del(5q). To date, allogenic stem cell transplantation ("ASCT") remains the only treatment option for possible cure. However, ASCT is painful for both the donor and the recipient because of the involvement of invasive procedures. ASCT can cause severe and even fatal complications to the recipient, particularly when Graft Versus Host Disease ("GVHD") occurs. Therefore, the risk of GVHD restricts the use of bone marrow transplantation to patients with otherwise fatal diseases. Further, as most patients are elderly and often only a few young MDS patients will have a matched donor, the use of bone marrow transplantation is limited. Accordingly, there is a need for additional therapeutics for treating MDS.

Neutropenia is a frequent complication of chemotherapy and occurs when myelosuppressive chemotherapeutic treatment reduces absolute neutrophil counts. One of the side effects of chemotherapy is myeloablative bone marrow toxicity. Bone marrow fills the inside of some bones such as the sternum, hip, femur, and humerus. Cells in the bone marrow are susceptible to the effects of chemotherapy due to their rapid rate of division. Chemotherapeutic agents prevent bone marrow stem cells from forming new blood cells. With time, after exposure to a chemotherapeutic agent, counts of the blood cells will fall at various rates, depending upon the particular type of cell as their average life spans differ. Low white blood cell count (e.g. neutropenia), for example, makes an individual more susceptible to infection.

Neutropenia predisposes cancer patients to potentially life-threatening infection, particularly from Gram-negative bacilli, Gram-positive cocci, and fungi. Risk of infection and mortality increases with the degree and duration of the neutropenic episode and the presence of fever.

Neutropenia requiring hospitalization is particularly common in patients with hematologic tumors. It is estimated to affect 1 in 23 patients diagnosed with such malignancies and 1 in 10 patients treated with chemotherapy. (See Cagglano V., et al. Incidence, Cost, and Mortality of Neutropenia Hospitalization Associated with Chemotherapy. Cancer. 2005. 103(9):1916.)

Neutropenia can compromise optimal cancer management by causing chemotherapy dose reduction, delay, or even discontinuation. These dose modifications often are implemented during the first cycles of chemotherapy because neutropenic events often occur early during the course of chemotherapy. Treatment response frequently depends on the delivery of standard chemotherapy doses, and modifications in dosing may threaten complete response rates and reduce survival. Thus, caregivers may face a challenge in maintaining adequate chemotherapeutic doses while managing neutropenic complications. Accordingly, there is a need for additional therapeutics for treating (including preventing) neutropenia.

Mucositis is a common and debilitating adverse event that often arises as a complication of antineoplastic therapy, such as chemotherapy and/or radiation therapy. The goal of such cancer therapies is to kill rapidly-dividing cancer cells; unfortunately, other cells may be killed by the treatments as well, including epithelial cells of the mucous membranes, which can lead to mucositis.

Mucositis is a serious and often very painful disorder involving inflammation and ulceration of the mucous membranes, such as those of the gastrointestinal tract, the oral and oropharyngeal cavities including the esophagus, as well as the bladder, ear, nasal, optical, vaginal, and rectal mucosa.

Severe mucositis especially concurrent with the cytopenic period can increase the risk of infection and death, prolong hospitalization, and impact quality of life. (See Niscola P., et al. Mucositis in Patients with Hematologic Malignancies: An Overview. Haematologica. 2007. 92:222.)

While the overall frequency of mucositis, as well as its severity, depends on factors including, for example, the treatment regimen and on the treatment modality, it is believed that approximately half of all cancer patients undergoing therapy suffer some degree of mucositis. Mucositis is believed to occur, for example, in virtually all patients treated with radiation therapy for head and neck tumors, all patients receiving radiation along the GI tract, and approximately 40% of those subjected to radiation therapy and/or chemotherapy for tumors in other locations (e.g., leukemias or lymphomas). It is also is believed to be highly prevalent in patients treated with high dose chemotherapy and/or irradiation for the purpose of myeloablation, such as in preparation for stem cell or bone marrow transplantation.

Mucositis can adversely impact the quality of life of cancer patients. Patients may experience pain, erythema, and/or deep, diffuse ulcers than can cause difficulty speaking, eating, and swallowing. Patients may also experience nausea and/or gastro-enteritis. Severe mucositis can lead to the need for parenteral nutrition or hospitalization or to disruptions in cancer treatment, alterations in treatment dosages, and/or shifting to different modes of treatment.

Mucositis may also be accompanied by a severe risk of fever and infection, as it can lead to a breach in the otherwise protective linings of the oral mucosa and gastrointestinal tract. The alimentary canal and gastrointestinal tract are colonized by a vast array of microorganisms, and mucosal lesions can provide a portal of entry for bacteria.

Current therapy for mucositis is largely palliative, including administration of antibiotics, antifungals, or anti-inflammatory agents combined with topical treatments containing compounds that modulate wound-healing and prevent infection. There is only a single medication approved for the treatment of mucositis-palifermin. It is approved for use, however, only in a limited subset of patients. Therefore, there is a need for additional therapeutics for treating (including preventing) mucositis.

The present application discloses methods for treating AML, MDS, neutropenia, and/or mucositis comprising administering to a subject in need thereof an effective amount of a compound of Formula (I) and compositions comprising the same.

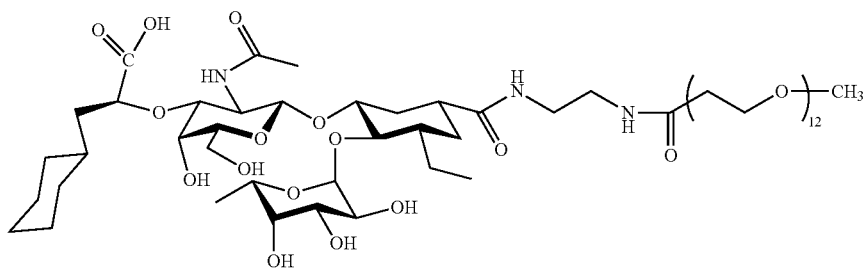

(I)

In some embodiments, a method is provided for treating AML, MDS, neutropenia, and/or mucositis comprising administering to a subject in need thereof an effective amount of a compound of Formula (I).

In some embodiments, a compound of Formula (I) is administered as a fixed daily dose. In some embodiments, a method is provided for treating AML, MDS, neutropenia, or mucositis comprising administering to a subject in need thereof a fixed dose of 200 mg to 4000 mg per day, 800 mg to 3200 mg per day, or 1000 mg to 2000 mg per day of a compound of Formula (I). In some embodiments, a method is provided for treating AML, MDS, neutropenia, or mucositis comprising administering to a subject in need thereof a fixed dose of 1600 mg per day of a compound of Formula (I).

In some embodiments, a compound of Formula (I) is administered as a weight-based daily dose. In some embodiments, a method is provided for treating AML, MDS, neutropenia, or mucositis comprising administering to a subject in need thereof 1 mg/kg to 100 mg/kg per day, 5 mg/kg to 80 mg/kg per day, or 10 mg/kg to 40 mg/kg per day of a compound of Formula (I). In some embodiments, a method is provided for treating AML, MDS, neutropenia, or mucositis comprising administering to a subject in need thereof 20 mg/kg per day of a compound of Formula (I).

In some embodiments, the daily dose (fixed or weight-based) of a compound of Formula (I) is administered as a single dose. In some embodiments, the daily dose of a compound of Formula (I) is administered in separate doses over the day. In some embodiments, the daily dose of a compound of Formula (I) is administered twice daily (i.e. BID). In some embodiments, the daily dose of a compound of Formula (I) is administered in two doses with about 12 hours between each dose. In some embodiments, the subject receives two doses of 800 mg each of a compound of Formula (I) per day. In some embodiments, the two doses per day of 800 mg each of a compound of Formula (I) are administered about 12 hours apart. For example, a fixed daily dose of 1600 mg may be administered over the day as two separate doses of 800 mg each, with the two 800 mg doses being administered about 12 hours apart. As another example, a weight-based daily dose of 20 mg/kg per day may be administered over the day as two separate doses of 10 mg/kg each, with the two 10 mg/kg doses being administered about 12 hours apart.

A compound of Formula (I) may be administered in a variety of methods, as described herein. For example, a compound of Formula (I) may be administered intravenously or subcutaneously.

In some embodiments, a compound of Formula (I) is administered to a subject that is receiving, has received, or will receive chemotherapy and/or radiotherapy, as described herein. For example, a compound of Formula (I) may be administered to a subject that is receiving, has received, or will receive two or more chemotherapeutic agents, such as mitoxantrone, etoposide, and cytarabine or fludarabine, cytarabine, and idarubicin. As another example, a compound of Formula (I) may be administered to a subject that is receiving, has received, or will receive velafermin, palifermin, thalidomide, and/or a thalidomide derivative.

In some embodiments, a compound of Formula (I) is administered to a subject that is receiving, has received, or will receive MMP inhibitors, inflammatory cytokine inhibitors, mast cell inhibitors, NSAIDs, NO inhibitors, MDM2 inhibitors, or antimicrobial compounds.

In some embodiments, where the subject has AML, the administration of the compound of Formula (I) extends the number of days the subject is in remission, reduces the number of days until remission, inhibits the metastasis of AML cells, and/or improves survival.

In some embodiments, where the subject has MDS, the administration of the compound of Formula (I) slows the progression of MDS, prevents the progression of MDS to leukemia, and/or improves survival.

In some embodiments, where the subject has neutropenia, the administration of the compound of Formula (I) reduces the number of days the subject is afflicted with neutropenia or reduces the severity of the neutropenia.

In some embodiments, where the subject has mucositis, the administration of the compound of Formula (I) reduces the number of days the subject is afflicted with mucositis or reduces the severity of the mucositis.

In some embodiments, a compound of Formula (I) is administered as a prodrug of Formula (I) or a pharmaceutically acceptable salt of any of the foregoing.

In some embodiments, the compound of Formula (I), prodrug of Formula (I), or pharmaceutically acceptable salt of any of the foregoing is administered in combination with a pharmaceutically acceptable carrier or diluent.

BRIEF DESCRIPTION OF THE DRAWINGS

FIG. 12A plots the fraction of dosing interval greater than the $IC_{50}$ of a compound of Formula (I) against four categories of efficacy response (CR=complete remission; CRi=complete remission with incomplete count recovery; MLFS=morphologic leukemia-free state; PD=persistent disease). FIG. 12B plots the fraction of dosing interval greater than the $IC_{90}$ of a compound of Formula (I) against the four categories of efficacy response. FIG. 12C plots Cmax (µg/ml) of a compound of Formula (I) against the four categories of efficacy response. FIG. 12D plots area under the curve ("AUC") of a compound of Formula (I) against the four categories of efficacy response. Box and whisker plots to illustrate the minimum, 25th percentile, median, 75th percentile, and maximum exposure metric in each category.

FIG. 16A illustrates the event-free survival rates, and FIG. 16B illustrates the overall survival rates.

Figure 1A:
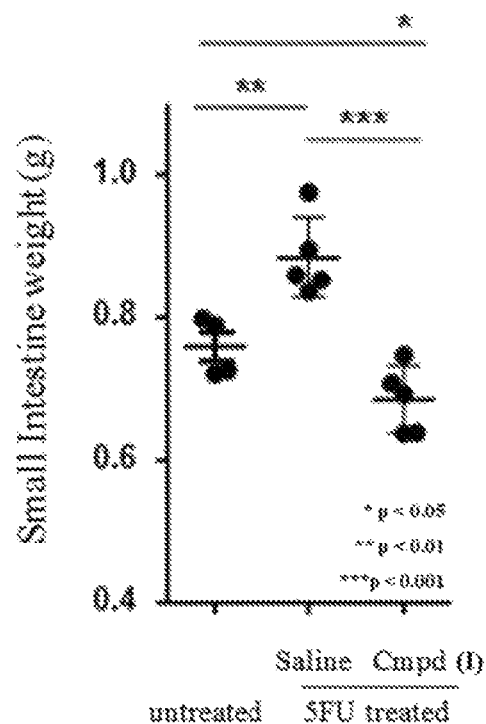
FIG. 1A illustrates the effect of a compound of Formula (I) on small intestine weight (a measure of inflammation) in mice, after 5-FU chemotherapy.

The terms "a," "an," and "the" refer to "one or more" when used in this application, including the claims. Thus, for example, reference to "a cell" includes one cell or a plurality of cells, and so forth.

The term "E-selectin antagonist" includes inhibitors of E-selectin only, as well as inhibitors of E-selectin and either P-selectin or L-selectin, and inhibitors of E-selectin, P-selectin, and L-selectin.

The terms "patient," "subject," "individual," and the like are used interchangeably herein, and refer to any animal, or cells thereof whether in vitro or in situ, amenable to the methods described herein. In some embodiments, the patient, subject or individual is a human. In some embodiments, the patient, subject or individual is in need of treatment includes those who already have the disease, condition, or disorder as well as those prone to have or at risk of developing the disease, condition, or disorder, and those in which the disease, condition, or disorder is to be prevented.

The term "prodrug" includes compounds that may be converted, for example, under physiological conditions or by solvolysis, to a biologically active compound described herein. Thus, the term "prodrug" includes metabolic precursors of compounds described herein that are pharmaceutically acceptable. A discussion of prodrugs can be found, for example, in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987. The term "prodrug" also includes covalently bonded carriers that release the active compound(s) as described herein in vivo when such prodrug is administered to a subject.

The term "pharmaceutically acceptable salt" includes both acid and base addition salts. Non-limiting examples of pharmaceutically acceptable acid addition salts include chlorides, bromides, sulfates, nitrates, phosphates, sulfonates, methane sulfonates, formates, tartrates, maleates, citrates, benzoates, salicylates, and ascorbates. Non-limiting examples of pharmaceutically acceptable base addition salts include sodium, potassium, lithium, ammonium (substituted and unsubstituted), calcium, magnesium, iron, zinc, copper, manganese, and aluminum salts. Pharmaceutically acceptable salts may, for example, be obtained using standard procedures well known in the field of pharmaceuticals.

The term "therapy" refers to "treating" or "treatment" of a disease or condition including preventing or inhibiting the disease (slowing or arresting its development), providing relief from the symptoms or side-effects of the disease (including palliative treatment), and relieving the disease (causing regression of the disease). "Therapy," "treating," or "treatment" may also refer to prophylactic treatment, which includes preventing or delaying the onset of the disease or condition from occurring in a subject that may be predisposed to the disease but does not yet experience or exhibit symptoms of the disease. "Therapy," "treating," or "treatment" can also refer to prolonging survival when compared to expected survival if a subject were not receiving treatment. It is not necessary for the "treatment" to show effectiveness in 100% of the patients treated, rather, the term "treatment" is intended to mean that a statistically significant proportion of patients can be treated effectively, in such a way that the symptoms and clinical signs show at least an improvement. The person skilled in the art can easily establish whether the proportion is statistically significant using various statistical methods (e.g. confidence intervals, determination of them P value, Student's t-test, Mann-Whitney test etc.). Confidence intervals have a confidence of at least 90%, at least 95%, at least 97%, at least 98%, or at least 99%. The P values are 0.1, 0.05, 0.01, 0.005, or 0.0001.

In some embodiments, the methods described herein provide at least one a compound of Formula (I) and, optionally, at least one additional pharmaceutically acceptable ingredient described herein in an amount sufficient to result in at least one desired therapeutic and/or prophylactic benefit. Therapeutic or prophylactic benefit includes, for example, an improved clinical outcome in either therapeutic treatment or prophylactic/preventative measures, wherein the object is to prevent or slow or retard (lessen) an undesired physiological change or disorder, or to prevent or slow or retard the expansion or severity of such disorder. As discussed herein, beneficial or desired clinical results from treating a subject include, but are not limited to, abatement, lessening, or alleviation of symptoms that result from or are associated with the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

An "effective amount" or "therapeutically effective" amount refers to an amount of a compound of the present disclosure or a composition comprising at least one such compound that, when administered to a subject, either as a single dose or as part of a series of doses, is effective to produce at least one therapeutic effect.

Compounds of Formula (I) may, for example, be synthesized according to methods disclosed in U.S. Pat. No. 9,109,002, which is hereby incorporated by reference.

The present disclosure includes within its scope all the possible geometric isomers, e.g. Z and E isomers (cis and trans isomers), of the compounds as well as all the possible optical isomers, e.g. diastereomers and enantiomers, of the compounds. Furthermore, the present disclosure includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof conventional resolution methods, e.g. fractional crystallization, may be used.

Compounds described herein may exist as polymorphs, which are also included by the present disclosure. In addition, some of the compounds may form hydrates with water or solvates with other solvents. Such hydrates and solvates are similarly included within the scope of compounds and compositions described herein.

Recently E-selectin-mediated interactions have been identified as targets for treating certain cancers. Not all cancer cells are alike. Even within a group of related cancer cells (e.g., a multiple myeloma cell line or prostate cancer tumor), gene expression and cell surface epitopes vary. Certain cancer cells, referred to as cancer stem cells, can establish new tumors, and the presence of higher numbers of these stem cells in a patient are associated with poorer prognoses. These cancer stem cells may also exhibit the more aggressive cancer traits such as drug resistance, accelerated disease progression, shorter survival, and higher incidence of relapse. Therefore, there is a need for treatments that will target cancer stem cells.

Cancer stem cells have been found to express cell surface carbohydrates that can bind to E-selectin. Cancer cells that can bind to E-selectin are capable of resisting certain standard treatments for cancer, such as chemotherapy, and are correlated with drug-resistance, accelerated disease progression, shorter survival, and higher incidence of relapse. It is thought that cancer cells expressing the carbohydrate epitope that binds E-selectin are able to survive chemotherapy treatment because they are also able to bind to E-selectin expressed on the vascular endothelium in protective niches in bone marrow. Thus, for example, when bound to the E-selectin in the protective niches of bone marrow, these cancer cells are able to survive cancer treatments such as chemotherapy. This is further evidence of the need for treatments that target cancer cells that bind to E-selectin.

E-selectin is an adhesion molecule expressed on the vascular endothelium that recognizes and binds to carbohydrate structures on the surfaces of cells in the bloodstream facilitating extravasation from the circulation. The carbohydrate ligands that bind E-selectin were first identified as tumor markers and the binding of E-selectin is thought to play a role in tumor metastasis and resistance to chemotherapy. E-selectin binds a trisaccharide domain common to both the carbohydrate structures sialyl $Le^a$ ($sLe^a$) and sialyl $Le^x$ ($sLe^x$) that is the epitope on tumor cells recognized by E-selectin.

A growing body of literature has reported that E-selectin-mediated interactions may play a role in AML, and the expression of E-selectin or its binding epitope (sialyl $Le^{a/x}$) may predict the clinical course and patient outcomes in AML (see Aref, S., et al. L and E Selectins in Acute Myeloid Leukemia: Expression, Clinical Relevance and Relation to Patient outcome. Hematology. 2002. 7(2):83-87). Soluble E-selectin (sE-selectin) may be shed from the cell membrane and detected by enzyme-linked immunosorbent assay (ELISA) in the peripheral blood. AML is associated with increased vessel density, and sE-selectin release by activated/proliferating endothelial cells in the bone marrow may contribute to increased E-selectin levels in patients with untreated AML (see Glenjen, N., et al., Serum Levels of Angiogenin, Basic Fibroblast Growth Factor and Endostatin in Patients Receiving Intensive Chemotherapy for Acute Myelogenous Leukemia. Intl. J. Cancer. 2002. 101(1):86). Soluble E-selectin levels are increased in the serum of patients with newly diagnosed AML compared with that in the serum of healthy subjects (see Horacek, J., et al., Biochip Array Technology and Evaluation of Serum Levels of Multiple Cytokines and Adhesion Molecules in Patients with Newly Diagnosed Acute Myeloid Leukemia. Experimental Oncology. 2014. 36(1):50). sE-selectin levels have also been correlated with the extramedullary infiltration of AML cells (P<0.001) and predict the occurrence of relapse of AML (P=0.01). Elevated sE-selectin levels at diagnosis of AML predicted low survival (P<0.001), and decreases in sE-selectin levels correlated with durable remission of AML (see Glenjen (2002) and Horacek (2014)). Therefore, there is a need for therapeutics for AML directed to the E-selectin mediated pathways.

E-selectin expression is transient in the normal vasculature during an inflammatory response but constitutive in the bone marrow ("BM"), generally resulting in sequestration of AML cells that express E-selectin or its binding epitope (sialyl Le$^{a/x}$) (i.e., AML blasts) in the bone marrow. Adhesion of AML-blasts to E-selectin initiates up-regulation of pathways critical to leukemia progression.

E-selectin is unique among vascular adhesion molecules in being able to directly activate the NF-κB pathway. Upstream blockade of E-selectin has been shown to inhibit NF-κB activation, suggesting that adhesion to E-selectin activates pro-survival NF-κB signaling in AML cells leading to enhanced chemoresistance (see Winkler, I. G., et al. Vascular E-selectin Protects Leukemia Cells from Chemotherapy by Directly Activating Pro-survival NF-kB Signaling—Therapeutic Blockade of E-selectin dampens NK-kB Activation. Blood. 2016. 128:2823). Collectively, these results suggest that E-selectin is a key vascular niche component in the bone marrow mediating resistance to chemotherapy. Therefore, there is a need for therapeutics for preventing the E-selectin mediated activation of the NF-κB pathway.

Chemotherapeutic agents can be ineffective at accessing and killing cancerous cells in the bone marrow, thereby reducing the treatment's overall effectiveness at eliminating the tumor. One explanation for the inability to completely eliminate the tumor may be attributed to the role of E-selectin interactions with AML blasts. AML blasts bound to E-selectin are resistant to the effects of chemotherapy (cell-adhesion mediated drug resistance, or CAMDR) in vitro, which is hypothesized to be a source of relapse in vivo (see Pezeshkian B., et al. Leukemia Mediated Endothelial Cell Activation Modulates Leukemia Cell Susceptibility to Chemotherapy Through a Positive Feedback Loop Mechanism. PLoS One. 2013. 8:e60823). E-selectin inhibition is hypothesized to disrupt the adhesion of AML cells in bone marrow and can mobilize AML blasts out of the bone marrow into the blood stream. These effects of E-selectin inhibition are proposed to result in greater susceptibility of AML cells to cytotoxic chemotherapy. In particular, it is thought that by blocking or otherwise inhibiting E-selectin, E-selectin is unable to bind to the cell surface carbohydrate. Without being able to bind to E-selectin, the cancer stem cells are unable to hide in protective niches in bone marrow and unable escape chemotherapy treatment. Therefore, there is a need for additional therapeutics for treating AML, particularly for treatments that target the AML blasts that bind to E-selectin.

As disclosed above, the present application is drawn to uses of a compound of Formula (I) or a pharmaceutical composition comprising the same for treating (including preventing) metastasis of cancer cells (also called tumor cells herein) in an individual (e.g., a subject, a patient) with AML, MDS, neutropenia, and/or mucositis by administering the compound or composition to the individual. In some embodiments, a compound of Formula (I) is used for treating (including preventing) metastasis of AML in a subject in need thereof. In some embodiments, AML is inhibited from infiltrating bone. Without wishing to be bound by theory, by inhibiting tumor cells from metastasizing to the bone marrow or to other protective niches in the body, the tumor cells may be inhibited from sequestration and protection from exposure to chemotherapy or radiotherapy. A subject in need of such treatment includes subjects who have been diagnosed with AML and/or subjects with an increased risk of developing AML.

In some embodiments of the methods described herein, the subject in need of treatment described herein is a human or non-human animal. A subject in need of treatment may exhibit symptoms of AML, MDS, neutropenia, and/or mucositis or may be at risk of developing AML, MDS, neutropenia, and/or mucositis. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

One or a combination of diagnostic methods, including physical examination, assessment and monitoring of clinical symptoms, and performance of analytical tests and methods described herein, may be used to monitor the health status of the subject and to assess likelihood of responding to treatment.

A suitable subject in need of treatment of AML, MDS, neutropenia, and/or mucositis may express a highly active E-selectin as determined by the genetic polymorphism for E-selectin of S128R (Alessandro R., et al., Role of S128R Polymorphism of E-selectin in Colon Metastasis Formation. Intl. J. Cancer. 2007. 121:528). In addition, subjects may be identified based on elevated expression of the E-selectin binding ligands (sialyl Le$^a$ and sialyl Le$^x$) as determined by antibodies directed against cancer-associated antigens CA-19-9 (Zheng C. X., et al. The Prognostic Value of Preoperative Serum Levels of CEA, CA19-9 and CA 72-4 in Patients with Colorectal Cancer. World J. Gastroenterol. 2001. 7:431), CD65, and FH-6. Antibody HECA-452 which recognizes similar carbohydrate ligands of E-selectin may also be used in a diagnostic assay to select the cancer patient population most likely to respond to this treatment. Subjects in need of the disclosed treatment also may be identified by elevated E-selectin ligand expression on AML blasts as determined by flow cytometry utilizing fluorescently labelled recombinant human E-selectin linked to the Fc domain of IgG.

In some embodiments, a compound of Formula (I) and, optionally, at least one additional pharmaceutically acceptable ingredient is administered in conjunction with (i.e., as an adjunct therapy, which is also called adjunctive therapy) chemotherapy or radiation or both.

Accordingly, a subject who has AML, MDS, neutropenia, and/or mucositis or who is at risk of developing AML, MDS, neutropenia, and/or mucositis may be administered a compound of Formula (I) and, optionally, at least one additional pharmaceutically acceptable ingredient in combination with at least one additional anti-cancer agent. In some embodiments, the at least one additional anti-cancer agent is chosen from chemotherapy agents, radiotherapeutic agents, inhibitors of phosphoinositide-3 kinase (PI3K), and inhibitors of VEGF. In some embodiments, the inhibitors of PI3K include a compound named by Exelixis as "XL499." In some embodiments, the VEGF inhibitors include a compound called "cabo" (previously known as XL184).

In some embodiments, the chemotherapy or radiation therapy is the primary therapy for treating AML or MDS. The chemotherapy and radiotherapy that may be administered depend upon several factors including the type of cancer or dysplasia, location of the tumor(s), stage of the cancer or dysplasia, age and gender and general health status of the subject. A compound of Formula (I) and, optionally, at least one additional pharmaceutically acceptable ingredient may be administered prior to, concurrently with, or subsequent to the primary chemotherapy or radiation treatment. In some embodiments, the compound of Formula (I) and, optionally, at least one additional pharmaceutically acceptable ingredient is/are administered with one or more cycles of chemotherapy or radiotherapy when multiple cycles of the chemotherapy or radiotherapy are administered to a subject for the treatment of a cancer. In the methods disclosed herein, the compound of Formula (I) may function independent of or in coordination with the anti-cancer agent, e.g., by enhancing effectiveness of the anti-cancer agent or vice versa. In some embodiments, the compound of Formula (I) enhances the efficacy of the chemotherapeutic agent(s) or radiotherapy.

In addition, serious and potentially life-threatening chemotherapy-induced neutropenia and mucositis are associated with E-selectin up-regulation, and inhibition or genetic ablation of E-selectin protects against these deleterious side effects (Winkler I G, Barbier V, Nutt H L, et al. Administration Of E-Selectin Antagonist GMI-1271 Improves Survival After High-Dose Chemotherapy By Alleviating Mucositis and Accelerating Neutrophil Recovery (Poster). 55th ASH Annual Meeting and Exposition; 2013; New Orleans, La.). For example, E-selectin plays an important role in chemotherapy-induced mucositis through the regulation of macrophage trafficking to the site of injury in the gut lining. Chemotherapy causes initial cell damage, and through a series of inflammatory and adhesion-molecule-mediated stages, the damage is propagated with resulting loss of mucosal integrity. E-selectin knockout mice are protected against chemotherapy-induced mucositis using 5-fluorouracil (5-FU). Similar results were demonstrated where mice administered a glycomimetic E-selectin inhibitor with 5-FU had enhanced neutrophil recovery (see Winkler, I. G., et al. Vascular Niche E-selectin Regulates Hematopoietic Stem Cell Dormancy, Self Renewal and Chemoresistance. Nature medicine. 2012. 18(11):1651), less mucositis and improved weight loss as compared with mice treated with 5-FU alone (see Winkler, I. G., et al. Administration of E-Selectin Antagonist GMI-1271 Improves Survival After High-Dose Chemotherapy by Alleviating Mucositis and Accelerating Neutrophil Recovery. Blood. 2013. 122(21):2266). Furthermore, E-selectin was up-regulated in the intestines following chemotherapy or radiation damage. Both genetic deletion of E-selectin and pharmacologic inhibition using glycomimetic E-selectin antagonist effectively blocked secondary migration of inflammatory F4/80+ Ly-6C+ macrophages to intestines of mice following chemotherapy or irradiation.

A compound of Formula (I) is useful in methods of the present invention as it relates to reducing a myeloablative bone marrow toxicity of chemotherapy, e.g., to treat neutropenia associated with chemotherapy treatments of AML or MDS patients. In some embodiments, an individual who is in need of reducing a myeloablative bone marrow toxicity of chemotherapy is administered a compound of Formula (I) and, optionally, at least one additional pharmaceutically acceptable ingredient in an amount effective for the reducing myeloablative bone marrow toxicity. As used herein, the term "reducing" (including variations such as "reduction") includes partial and total reduction of at least one (i.e., one or more) myeloablative bone marrow toxicity of chemotherapy; and also includes partial and total prevention of at least one such toxicity (e.g., by administration of a compound of Formula (I) and, optionally, at least one additional pharmaceutically acceptable ingredient prior to, simultaneous with, or shortly after, initiation of chemotherapy). For example, a compound of Formula (I) may not prevent neutropenia, but may promote a more rapid and sustained recovery of neutrophils after chemotherapy.

In some embodiments, methods are provided for treating or preventing neutropenia in a subject with AML or MDS who is treated with or will be treated with a chemotherapeutic drug(s) or radioactive therapy comprising administering a compound of Formula (I) and, optionally, at least one pharmaceutically acceptable ingredient. In some embodiments, the subject has received, is receiving, or will receive both chemotherapy and radiation therapy. Also, provided herein are methods for reducing chemosensitivity or radiosensitivity of HSCs to the chemotherapeutic drug(s) or radioactive therapy, respectively, in a subject. Because repeated cycles of chemotherapy and radiotherapy often diminish the ability of HSCs to recover and replenish bone marrow, a compound of Formula (I), a prodrug thereof, or a pharmaceutically acceptable salt of any of the foregoing may be used in subjects who will receive more than one cycle of chemotherapy or radiotherapy or a combination of both chemotherapy and radiotherapy. A compound of Formula (I) and, optionally, at least one pharmaceutically acceptable ingredient, may therefore be administered with any one or more of each of the cycles of chemotherapy or radiotherapy (or combination) administered to the subject. Also provided herein is a method for inhibiting adhesion of AML tumor cells or MDS cells that express a ligand of E-selectin to an endothelial cell expressing E-selectin on its cell surface, which method comprises contacting the endothelial cell with a compound of Formula (I) as described herein, thereby permitting the compound to interact with E-selectin on the endothelial cell surface and inhibiting binding of the AML tumor cell or MDS cell to the endothelial cell. Without wishing to be bound by theory, inhibiting adhesion of tumor or MDS cells to endothelial cells may reduce in a significant manner, the capability of the tumor or MDS cells to extravasate into other organs, blood vessels, lymph, or bone marrow and thereby reduce, decrease, or inhibit, or slow the progression of the cancer, including reducing, decreasing, inhibiting, or slowing metastasis.

In some embodiments, the amount of a compound of Formula (I) administered per day (i.e., the daily dosage) is a fixed amount. In some embodiments, the fixed daily dosage is 200 mg to 4000 mg per day. In some embodiments, the fixed daily dosage is 800 mg to 3200 mg per day. In some embodiments, the fixed daily dosage is 1000 mg to 2000 mg per day. In some embodiments, the fixed daily dosage is 1600 mg per day.

In some embodiments, the daily dosage is based on the weight of the subject to which the dosage is administered (i.e., weight-based). In some embodiments, the weight-based daily dosage is 1 mg/kg to 100 mg/kg per day, 5 mg/kg to 80 mg/kg per day, or 10 mg/kg to 40 mg/kg per day. In some embodiments, the weight-based daily dosage is 20 mg/kg per day.

The daily dosage (whether fixed or weight-based) may be administered as one dose per day or in multiple doses in a single day. In some embodiments, the daily dosage is equally divided between multiple doses. In some embodiments, the daily dosage is unequally divided between multiple doses. In some embodiments, the fixed daily dosage is 1600 mg, administered as 2 doses, with each dose comprising 800 mg of a compound of Formula (I). In some embodiments, the weight-based daily dosage is 20 mg/kg, administered as 2 doses, with each dose comprising 10 mg/kg of a compound of Formula (I). In some embodiments, the doses are administered about 12 hours apart.

The minimum dose that is sufficient to provide effective therapy may be used in some embodiments. Subjects may generally be monitored for therapeutic effectiveness using assays suitable for the disease or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g., serum), and/or in the urine, and/or other biological sample from the subject. Any method practiced in the art to detect the compound, or metabolite thereof, may be used to measure the level of the compound during the course of a therapeutic regimen.

The daily dosage amount and dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

In pharmaceutical dosage forms, any one or more of the compounds of the present disclosure may be administered in the form of a pharmaceutically acceptable derivative, such as a salt or prodrug, and/or it/they may also be used alone and/or in appropriate association, as well as in combination, with other pharmaceutically active compounds.

One of ordinary skill in the art would understand the amount of pharmaceutically acceptable derivative, such as a prodrug or pharmaceutically acceptable salt, that is equivalent to the daily dosages and individual doses of a compound of Formula (I) described herein. That is, for example, given the disclosure above of a fixed daily dose of 1600 mg of a compound of Formula (I), one of ordinary skill in the art would understand how to determine an equivalent fixed daily dose of a prodrug of Formula (I) or a pharmaceutically acceptable salt of any of the foregoing.

Pharmaceutical compositions may be administered in any manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the pharmaceutical composition in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail herein).

The pharmaceutical compositions described herein may be administered to a subject in need thereof by any of several routes that can effectively deliver an effective amount of the compound. In some embodiments, the pharmaceutical composition is administered parenterally. Non-limiting suitable routes of parenteral administration include subcutaneous, intravenous, intramuscular, intrasternal, intracavernous, intrameatal, and intraurethral injection and/or infusion. In some embodiments, the pharmaceutical composition is administered intravenously (IV). Non-limiting suitable routes of IV administration include via a peripheral line, a central catheter, and a peripherally inserted central line catheter (PICC). In some embodiments, the pharmaceutical composition is administered subcutaneously.

In some embodiments, the composition comprising a compound of Formula (I) and, optionally, at least one additional pharmaceutically acceptable ingredient is formulated as a liquid and is administered parenterally. In some embodiments a compound of Formula (I) and, optionally, at least one additional pharmaceutically acceptable ingredient is formulated as a liquid and is administered intravenously (IV). In some embodiments a compound of Formula (I) and, optionally, at least one additional pharmaceutically acceptable ingredient is formulated as a liquid and is administered subcutaneously (subQ). In some embodiments a compound of Formula (I) and, optionally, at least one additional pharmaceutically acceptable ingredient is formulated as a liquid and is administered intramuscularly (IM). In some embodiments a compound of Formula (I) and, optionally, at least one additional pharmaceutically acceptable ingredient is formulated as a liquid and is administered by intraosseous infusion.

The pharmaceutical compositions described herein may be sterile aqueous or sterile non-aqueous solutions, suspensions or emulsions, and may additionally comprise at least one pharmaceutically acceptable excipient or diluent (i.e., a non-toxic material that does not interfere with the activity of the active ingredient). Such compositions may be in the form of a solid, liquid, or gas (aerosol). Alternatively, the compositions described herein may be formulated as a lyophilizate, or compounds described herein may be encapsulated within liposomes using technology known in the art. The pharmaceutical compositions may further comprise at least one additional component, which may be biologically active or inactive. Non-limiting examples of such components include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient, diluent, or carrier known to those of ordinary skill in the art for use in pharmaceutical compositions may be employed in the compositions described herein. Excipients for therapeutic use are well known, and are described, for example, in Remington: The Science and Practice of Pharmacy (Gennaro, 21st Ed. 2005). In general, the type of excipient or diluent is selected based on the mode of administration, as well as the chemical composition of the active ingredient(s). Pharmaceutical compositions may be formulated for the particular mode of administration. For parenteral administration, pharmaceutical compositions may further comprise water, saline, alcohols, fats, waxes, and buffers.

As previously disclosed, the pharmaceutical compositions (e.g., for delivery by injection) may be in the form of a liquid. A liquid pharmaceutical composition may include, for example, at least one the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition is an injectable pharmaceutical composition, and in some embodiments, the injectable pharmaceutical composition is sterile.

In some embodiments, the effective amount a compound of Formula (I) is administered in conjunction with another treatment.

In some embodiments, the subject is administered one or more hypomethylating agents such as decitabine, 5-azacitidine, or guadecitabine. In some embodiments, a compound of Formula (I) and, optionally, at least one additional pharmaceutically acceptable ingredient is administered before, during, and/or after a hypomethylating agent.

In some embodiments, the subject is administered one or more alkylating agents, such as carboplatin, cisplatin, oxaliplatin, carmustine, lomustine, streptozocin, altretamine, procarbazine, dacarbazine, temozolomide, busulfan, thiotepa, hexamethylmelamine, mechlorethamine, cyclophosphamide, chlorambucil, melphalan, or ifosfamide. In some embodiments, a compound of Formula (I), a prodrug thereof, or a pharmaceutically acceptable salt of any of the foregoing, and, optionally, at least one additional pharmaceutically acceptable ingredient is administered before, during, and/or after an alkylating agent.

In some embodiments, the subject is administered one or more plant alkaloids such as vincristine, vinblastine, vinorelbine, paclitaxel, docetaxel, etoposide, tenisopide, irinotecan, or topotecan. In some embodiments, a compound of Formula (I) and, optionally, at least one additional pharmaceutically acceptable ingredient is administered before, during, and/or after a plant alkaloid.

In some embodiments, the subject is administered one or more antitumor antibiotics, such as doxorubicin, daunorubicin, epirubicin, mitoxantrone, idarubicin, dactinomycin, plicamycin, mitomycin, or bleomycin. In some embodiments, a compound of Formula (I) and, optionally, at least one additional pharmaceutically acceptable ingredient is administered before, during, and/or after an antitumor antibiotic.

In some embodiments, the subject is administered one or more antimetabolites, such as methotrexate, 5-fluorouracil, foxuridine, cytarabine, capecitibine, gemcitabine, 6-mercaptopurine, 6-thioguanine, cladribine, fludarabine, nelarabine, or pentostatin. In some embodiments, a compound of Formula (I) and, optionally, at least one additional pharmaceutically acceptable ingredient is administered before, during, and/or after an antimetabolite.

In some embodiments, the subject is administered one or more topoisomerase inhibitors, such as ironotecan, topotecan, amsacrine, etoposide, etoposide phosphate, or teniposide. In some embodiments, a compound of Formula (I) and, optionally, at least one additional pharmaceutically acceptable ingredient is administered before, during, and/or after a topoisomerase inhibitor.

In some embodiments, the subject is administered one or more ribonucleotide reductase inhibitors, such as hydroxyurea. In some embodiments, a compound of Formula (I) and, optionally, at least one additional pharmaceutically acceptable ingredient is administered before, during, and/or after a ribonucleotide reductase inhibitor.

In some embodiments, the subject is administered one or more adrenocortical steroid inhibitors, such as mitotane. In some embodiments, a compound of Formula (I) and, optionally, at least one additional pharmaceutically acceptable ingredient is administered before, during, and/or after an adrenocortical steroid inhibitor.

In some embodiments, the subject is administered one or more enzymes, such as asparaginase or pegaspargase. In some embodiments, a compound of Formula (I) and, optionally, at least one additional pharmaceutically acceptable ingredient is administered before, during, and/or after an enzyme.

In some embodiments, the subject is administered one or more antimicrotubule agents, such as estramustine. In some embodiments, a compound of Formula (I) optionally, at least one additional pharmaceutically acceptable ingredient is administered before, during, and/or after an antimicrotubule agent.

In some embodiments, the subject is administered one or more targeted therapeutic agents, such as midostaurin, gilteritinib, enasidenib, imatininib mesylate, gefitinib, erlotinib, sorafenib, sunitinib, dasatinib, lapatinib, nilotinib, bortezomib, tofacitinib, crizotinib, obatoclax, naviclax, gossypol, apatinib, vemurafenib, dabrafenib, MEK162, temsirolimus, everolimus, rituximab, trastuzumab, alemtuzamab, panitumumab, bevacizumab, idasanutlin, or ipilimumab. In some embodiments, a compound of Formula (I) and, optionally, at least one additional pharmaceutically acceptable ingredient is administered before, during, and/or after a targeted therapeutic agent.

In some embodiments, the subject is administered one or more retinoids, such as bexarotene, isotretinoin, or tretinoin. In some embodiments, a compound of Formula (I) and, optionally, at least one additional pharmaceutically acceptable ingredient is administered before, during, and/or after a retinoid.

In some embodiments, the subject is administered one or more chemotherapeutic agents, such as Vyxeos (daunorubicin and cytarabine), Mylotarg (gemtuzamab and ozogamicin), idasanutlin and cytarabine, IA (idarubicin and cytarabine), MEC (mitoxantrone, etoposide, cytarabine), FAI (fludarabine, cytarabine, idarubicin), 7+3 ida (cytarabine, idarubicin), 5+2 ida (cytarabine, idarubicin), 7+3 dauno (cytarabine, daunorubicin), 5+2 dauno (cytarabine, daunorubicin), FLAG (fludarabine, cytarabine, G-CSF), FLAG-Ida (fludarabine, cytarabine, idarubicin, G-CSF), FLAG-Mito (mitoxantrone, fludarabine, cytarabine, G-CSF), FLAMSA (fludarabine, cytarabine, amsacrine), FLAMSA-Bu (fludarabine, cytarabine, amsacrine, busulfan), FLAMSA-Mel (fludarabine, cytarabine, amsacrine, melphalan), or TAD (tioguanine, cytarabine, daunorubicin). In some embodiments, the subject is administered two or more chemotherapeutic agents. In some embodiments, when more than one chemotherapeutic agent is used, the chemotherapeutic agents are administered simultaneously with each other or they may be administered sequentially to each other. In some embodiments, the chemotherapeutic agents are given in an alternating fashion (e.g., a first chemotherapeutic agent is administered, then a second chemotherapeutic agent is administered, then the first chemotherapeutic agent is administered). In some embodiments, a compound of Formula (I) and, optionally, at least one additional pharmaceutically acceptable ingredient is administered before, during, and/or after the administration of one or more chemotherapeutic agents. That is, a compound of Formula (I), when administered with one or more chemotherapeutic agents, may be administered at any time in relation to the administration of one or more of the chemotherapeutic agents.

In some embodiments, the subject is administered thalidomide or one or more thalidomide derivatives, such as lenalidomide. In some embodiments, the subject receives thalidomide or a thalidomide derivative and one or more chemotherapeutic agents. In some embodiments, a compound of Formula (I) and, optionally, at least one additional pharmaceutically acceptable ingredient is administered before, during, and/or after receiving thalidomide or a thalidomide derivative.

In some embodiments, the subject is administered MEC induction chemotherapy. In some embodiments, a compound of Formula (I) and, optionally, at least one additional pharmaceutically acceptable ingredient is administered before, during, and/or after the MEC induction chemotherapy. In some embodiments, the cycle of MEC induction chemotherapy lasts for five consecutive days. In some embodiments, a compound of Formula (I) and, optionally, at least one additional pharmaceutically acceptable ingredient is given one day prior to initiating chemotherapy, each day during chemotherapy, and for two days following the last dose of chemotherapy (see, e.g., FIG. 14A). In some embodiments, the MEC induction chemotherapy comprises treatment with IV mitoxantrone, IV etoposide, and IV cytarabine. In some embodiments, the MEC induction chemotherapy comprises treatment with 10 mg/m$^2$/d IV mitoxantrone, 100 mg/m$^2$/d IV etoposide, and 1000 mg/m$^2$/d IV cytarabine.

In some embodiments, the subject is administered FAI induction chemotherapy. In some embodiments, a compound of Formula (I) and, optionally, at least one additional pharmaceutically acceptable ingredient is administered before, during, and/or after the FAI induction chemotherapy. In some embodiments, the cycle of FAI induction therapy lasts for five consecutive days. In some embodiments, a compound of Formula (I), a prodrug thereof, or a pharmaceutically acceptable salt of any of the foregoing, and, optionally, at least one additional pharmaceutically acceptable ingredient is given one day prior to initiating chemotherapy, each day during chemotherapy, and for two days following the last dose of chemotherapy (see, e.g., FIG. 14A). In some embodiments, the FAI induction chemotherapy comprises treatment with IV fludarabine, IV cytarabine, and IV idarubicin. In some embodiments, the FAI induction chemotherapy comprises 30 mg/m$^2$ IV fludarabine and 2 g/m$^2$ IV cytarabine for the five consecutive days, and 10 mg/m$^2$ IV idarubicin for the first three consecutive days.

In some embodiments, chemotherapy treatment continues after the induction cycle.

In some embodiments, after induction chemotherapy, a subject may receive one or more cycles of reduced-dose MEC consolidation chemotherapy. In some embodiments, the reduced-dose MEC chemotherapy cycle lasts four consecutive days. In some embodiments, a compound of Formula (I) and, optionally, at least one additional pharmaceutically acceptable ingredient is administered before, during, and/or after the cycle of the reduced-dose chemotherapy. In some embodiments, a compound of Formula (I) and, optionally, at least one additional pharmaceutically acceptable ingredient is administered one day prior to initiating the reduced-dose cycle of chemotherapy, each day during chemotherapy, and for two days following the last dose of chemotherapy (see, e.g., FIG. 14B). In some embodiments, the reduced-dose MEC therapy comprises treatment with IV mitoxantrone and IV etoposide for five consecutive days, and IV cytarabine on days 2-5 of the cycle. In some embodiments, the reduced-dose MEC therapy comprises administration of 10 mg/m$^2$/d IV mitoxantrone, 100 mg/m$^2$/d IV etoposide, and 1000 mg/m$^2$/d IV cytarabine for four consecutive days.

In some embodiments, after induction chemotherapy, a subject may receive one or more cycles of HiDAC consolidation chemotherapy. In some embodiments, three or four cycles of HiDAC chemotherapy may be administered. In some embodiments, a HiDAC therapy cycle lasts five consecutive days. In some embodiments, a compound of Formula (I) and, optionally, at least one additional pharmaceutically acceptable ingredient is administered before, during, and/or after the cycle of the HiDAC chemotherapy. In some embodiments, a compound of Formula (I) and, optionally, at least one additional pharmaceutically acceptable ingredient is administered one day prior to initiating chemotherapy, each day during chemotherapy, and for two days following the last dose of chemotherapy (see, e.g., FIG. 14B). In some embodiments, the HiDAC chemotherapy cycle comprises treatment with IV cytarabine about every 3 hours on Days 2, 4, and 6. In some embodiments, the HiDAC chemotherapy cycle comprises treatment with IV cytarabine about every 12 hours on Days 2, 4, and 6. In some embodiments, the HiDAC chemotherapy cycle comprises administration of 3 g/m$^2$ IV cytarabine about every 3 hours on Days 2, 4, and 6. In some embodiments, the HiDAC chemotherapy cycle comprises administration of 2-3 g/m$^2$ IV cytarabine about every 12 hours on Days 2, 4, and 6.

In some embodiments, after induction chemotherapy, a subject may receive one or more cycles of reduced-dose IDAC consolidation chemotherapy. In some embodiments, three cycles of reduced-dose IDAC consolidation chemotherapy may be administered. In some embodiments, the reduced-dose IDAC consolidation therapy cycle lasts five consecutive days. In some embodiments, a compound of Formula (I) and, optionally, at least one additional pharmaceutically acceptable ingredient is administered before, during, and/or after the cycle of the reduced-dose IDAC consolidation chemotherapy. In some embodiments, a compound of Formula (I) and, optionally, at least one additional pharmaceutically acceptable ingredient is administered one day prior to initiating the reduced-dose IDAC consolidation chemotherapy cycle, each day during chemotherapy, and for two days following the last dose of chemotherapy (see, e.g., FIG. 14B). In some embodiments, the reduced-dose IDAC consolidation chemotherapy cycle comprises treatment with IV cytarabine for five consecutive days. In some embodiments, the IDAC chemotherapy cycle comprises administration of 1.5 g/m$^2$/day IV cytarabine for five consecutive days. In some embodiments, the dose of cytarabine may be reduced to 1 g/m$^2$/day. In some embodiments, the reduced-dose IDAC consolidation chemotherapy cycle comprises treatment with IV cytarabine about every 12 hours on Days 2, 4, and 6 (for a total of 6 doses). In some embodiments, the IDAC chemotherapy cycle comprises administration of 1.5 g/m$^2$ IV cytarabine about every 12 hours on Days 2, 4, and 6 (for a total of 6 doses). In some embodiments, the dose of cytarabine may be reduced to 1 g/m$^2$/day for part or all of the cycle.

In some embodiments, the subject is administered decitabine chemotherapy. In some embodiments, a compound of Formula (I) and, optionally, at least one additional pharmaceutically acceptable ingredient is administered before, during, and/or after the decitabine chemotherapy cycle. In some embodiments, a cycle of decitabine chemotherapy lasts five consecutive days. In some embodiments, a cycle of decitabine chemotherapy lasts ten consecutive days. In some embodiments, the decitabine chemotherapy treatment comprises treatment with IV decitabine once daily for 5 consecutive days. In some embodiments, the decitabine chemotherapy treatment comprises administering 20 mg/m$^2$ IV decitabine once daily for 5 consecutive days. In some embodiments, the decitabine chemotherapy treatment comprises treatment with IV decitabine once daily for 10 consecutive days. In some embodiments, the decitabine chemotherapy treatment comprises administering 20 mg/m² IV decitabine once daily for 10 consecutive days. In some embodiments, subjects receiving a five-day cycle of decitabine are administered a compound of Formula (I) and, optionally, at least one additional pharmaceutically acceptable ingredient once the day before the first infusion of decitabine and once each day of chemotherapy. In some embodiments, subjects receiving a ten-day cycle of decitabine are administered a compound of Formula (I) and, optionally, at least one additional pharmaceutically acceptable ingredient twice the day before the first infusion of decitabine and twice each day of chemotherapy.

In some embodiments, the subject is administered 7+3 dauno chemotherapy. In some embodiments, a compound of Formula (I) and, optionally, at least one additional pharmaceutically acceptable ingredient is administered before, during, and/or after the 7+3 dauno chemotherapy cycle. In some embodiments a compound of Formula (I) and, optionally, at least one additional pharmaceutically acceptable ingredient is given one day prior to initiating chemotherapy, each day during chemotherapy, and for two days following the last dose of chemotherapy. In some embodiments, a cycle of 7+3 dauno chemotherapy lasts seven consecutive days. In some embodiments, the 7+3 dauno chemotherapy comprises administering a continuous IV infusion of cytarabine over seven days (168 hours), with IV daunorubicin administered for the first three consecutive days. In some embodiments, the 7+3 dauno chemotherapy comprises administering a continuous IV infusion of 100 mg/m²/d cytarabine over seven days (168 hours), with 60 mg/m²/d IV daunorubicin administered for the first three consecutive days. In some embodiments, follow-up cycles of cytarabine and daunorubicin chemotherapy may be administered. In some embodiments, the follow-up cycle comprises administering a continuous IV infusion of cytarabine over five days (120 hours), with IV daunorubicin administered for the first two consecutive days. In some embodiments, the follow-up cycle comprises administering a continuous IV infusion of 100 mg/m²/d cytarabine over five days (120 hours), with 60 mg/m²/d IV daunorubicin administered for the first two consecutive days.

In some embodiments, the subject is administered 7+3 ida chemotherapy. In some embodiments, a compound of Formula (I), a prodrug thereof, or a pharmaceutically acceptable salt of any of the foregoing, and, optionally, at least one additional pharmaceutically acceptable ingredient is administered before, during, and/or after the 7+3 ida chemotherapy cycle. In some embodiments a compound of Formula (I) and, optionally, at least one additional pharmaceutically acceptable ingredient is given one day prior to initiating chemotherapy, each day during chemotherapy, and for two days following the last dose of chemotherapy. In some embodiments, a cycle of 7+3 ida chemotherapy lasts seven consecutive days. In some embodiments, the 7+3 ida chemotherapy comprises administering a continuous IV infusion of 200 mg/m²/d cytarabine over seven days (168 hours), with 12 mg/m²/d IV idarubicin administered for the first three consecutive days. In some embodiments, the 7+3 ida chemotherapy comprises administering a continuous IV infusion of cytarabine over seven days (168 hours), with IV idarubicin administered for the first three consecutive days. In some embodiments, follow-up cycles of cytarabine and idarubicin chemotherapy may be administered. In some embodiments, the follow-up cycle comprises administering a continuous IV infusion of 200 mg/m²/d cytarabine over five days (120 hours), with 12 mg/m²/d IV idarubicin administered for the first two consecutive days. In some embodiments, the follow-up cycle comprises administering a continuous IV infusion of cytarabine over five days (120 hours), with IV idarubicin administered for the first two consecutive days.

Kits comprising unit doses of at least one compound of the present disclosure, for example in injectable doses, are provided. Such kits may include a container comprising the unit dose, an informational package insert describing the use and attendant benefits of the therapeutic in treating the pathological condition of interest, and/or optionally an appliance or device for delivery of the at least one compound or composition comprising the same.

EXAMPLES

Example 1

E-Selectin Activity—Binding Assay

The inhibition assay to screen for and characterize glycomimetic antagonists of E-selectin is a competitive binding assay, which allows the determination of $IC_{50}$ and $IC_{90}$ values. An E-selectin/Ig chimera was immobilized in 96 well microtiter plates by incubation at 37° C. for 2 hours. To reduce nonspecific binding, bovine serum albumin was added to each well and incubated at room temperature for 2 hours. The plate was washed and serial dilutions of the test compounds were added to the wells in the presence of conjugates of biotinylated, $sLe^a$ polyacrylamide with streptavidin/horseradish peroxidase and incubated for 2 hours at room temperature.

To determine the amount of $sLe^a$ bound to immobilized E-selectin after washing, the peroxidase substrate, 3, 3', 5, 5' tetramethylbenzidine (TMB) was added. After 3 minutes, the enzyme reaction was stopped by the addition of $H_3PO_4$, and the absorbance of light at a wavelength of 450 nm was determined. The concentration of a compound of Formula (I), required to inhibit binding by 50% was determined and reported as the $IC_{50}$. The concentration required to inhibit binding by 90% was determined and reported as the $IC_{90}$. $IC_{50}$ and $IC_{90}$ values: disclosed herein are provided in the following table.

E-Selectin Antagonist Activity

| | $IC_{50}$ | | $IC_{90}$ | |
|---|---|---|---|---|
| Species | µM | ng/mL | µM | ng/mL |
| Mouse | 2.45 | 3250 | 3.70 | 4908 |
| Human | 2.4 | 3184 | 5.68 | 7535 |

Example 2

5-FU Induced Mucositis Assay

Mice (C57bl/6) were treated with 150 mg/kg of 5-fluorouracil (5-FU) intraperitoneal (IP) on days 0 and 10. After the second injection of 5-FU, the mice were treated with a compound of Formula (I) (20 mg/kg in saline, IP, BID (i.e. 40 mg/kg per day)) or saline alone (0.15 M NaCl) for 4 days.

Figure 1B:
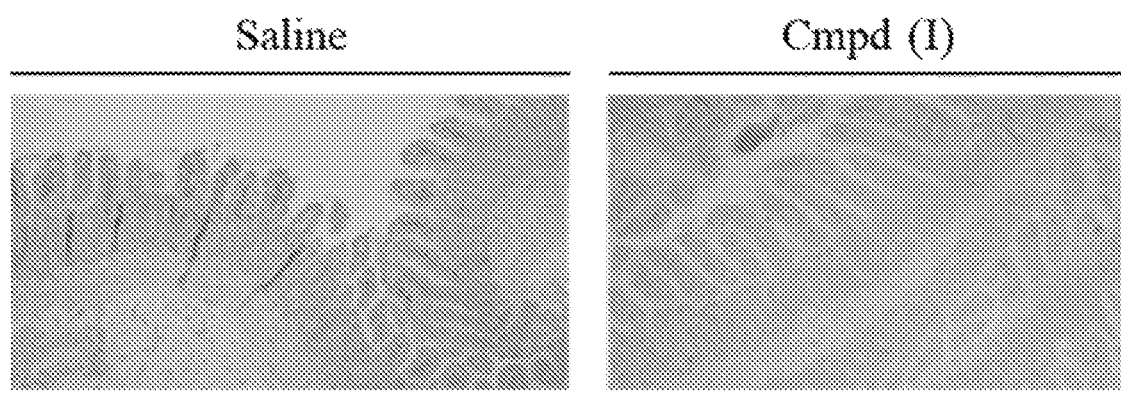
FIG. 1B illustrates that 5-FU induced intestinal erosion, villous loss, and macrophage infiltration was attenuated treatment with a compound of Formula (I).

Mice were then sacrificed and the small intestines were removed and weighed to determine the degree of inflammation. FIG. 1A illustrates that treatment with a compound of Formula (I) protects against chemotherapy induced gastrointestinal mucositis as measured by intestinal weight. FIG. 1B illustrates that intestinal erosion, villous loss, and macrophage infiltration after administration of chemotherapy were ameliorated by concurrent administration of a compound of Formula (I).

The results show an amelioration of chemotherapy-induced intestinal mucositis in mice treated with a compound of Formula (I).

Example 3

Radiation Induced Mucositis Assay

Figure 2:
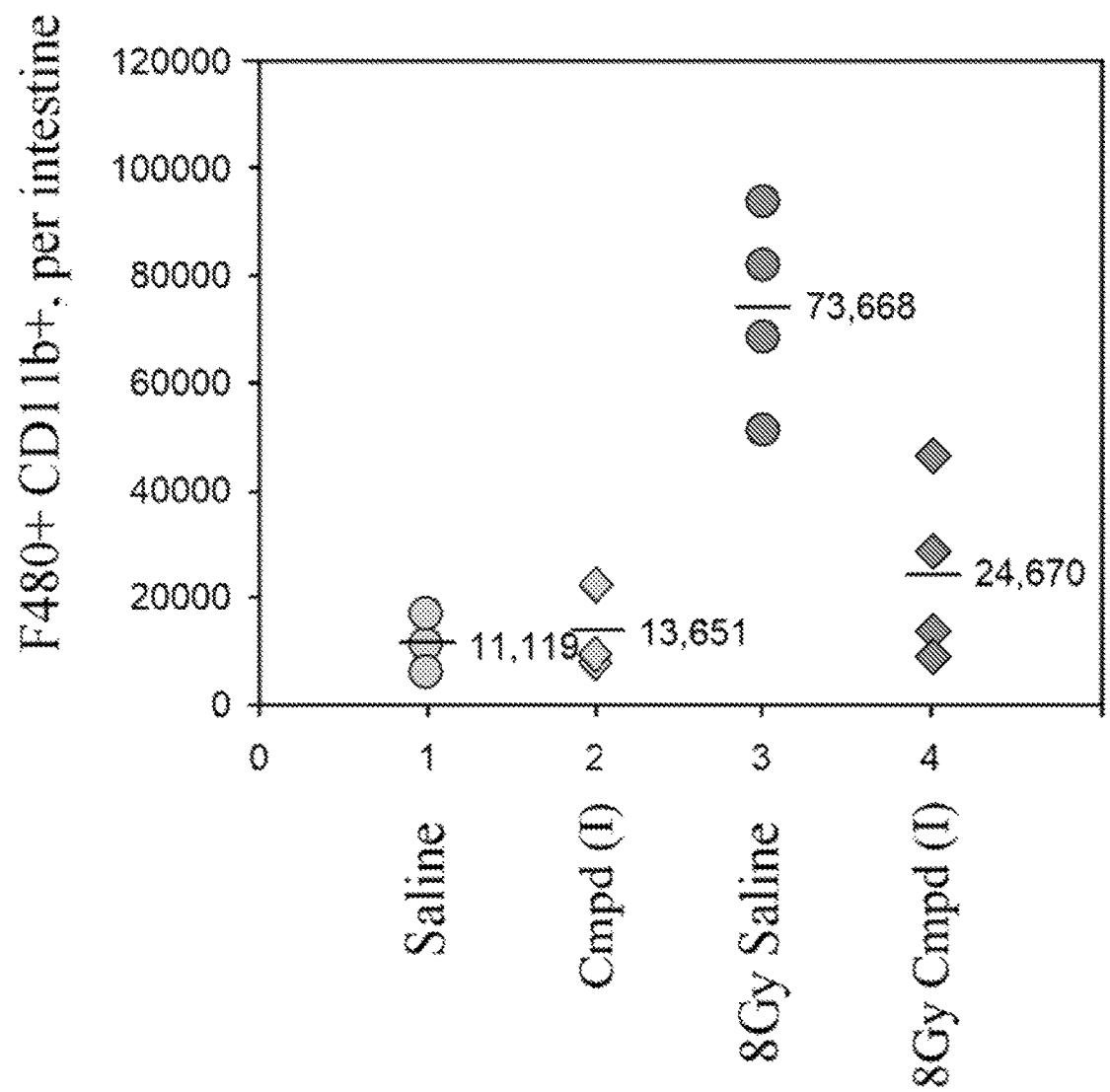
FIG. 2 illustrates the effect of a compound of Formula (I), on macrophage infiltration of the intestine in mice, after radiation therapy.

Mice (C57bl/6) were subjected to whole body irradiation (8.0 Gy) and immediately afterwards treated with a compound of Formula (I) (20 mg/kg in saline, IP, BID (i.e. 40 mg/kg per day)) or saline alone (0.15 M NaCl) for 6 days. The small intestine was removed at day 6 and digested to release cells. The number of CD11b$^+$F4/80$^+$ macrophages from the small intestine was determined by flow cytometry (FIG. 2).

The results show treatment with a compound of Formula (I), decreased migration of inflammatory macrophages to the intestines of mice subjected to whole body radiation.

Example 4

Figures 3A, 3B:
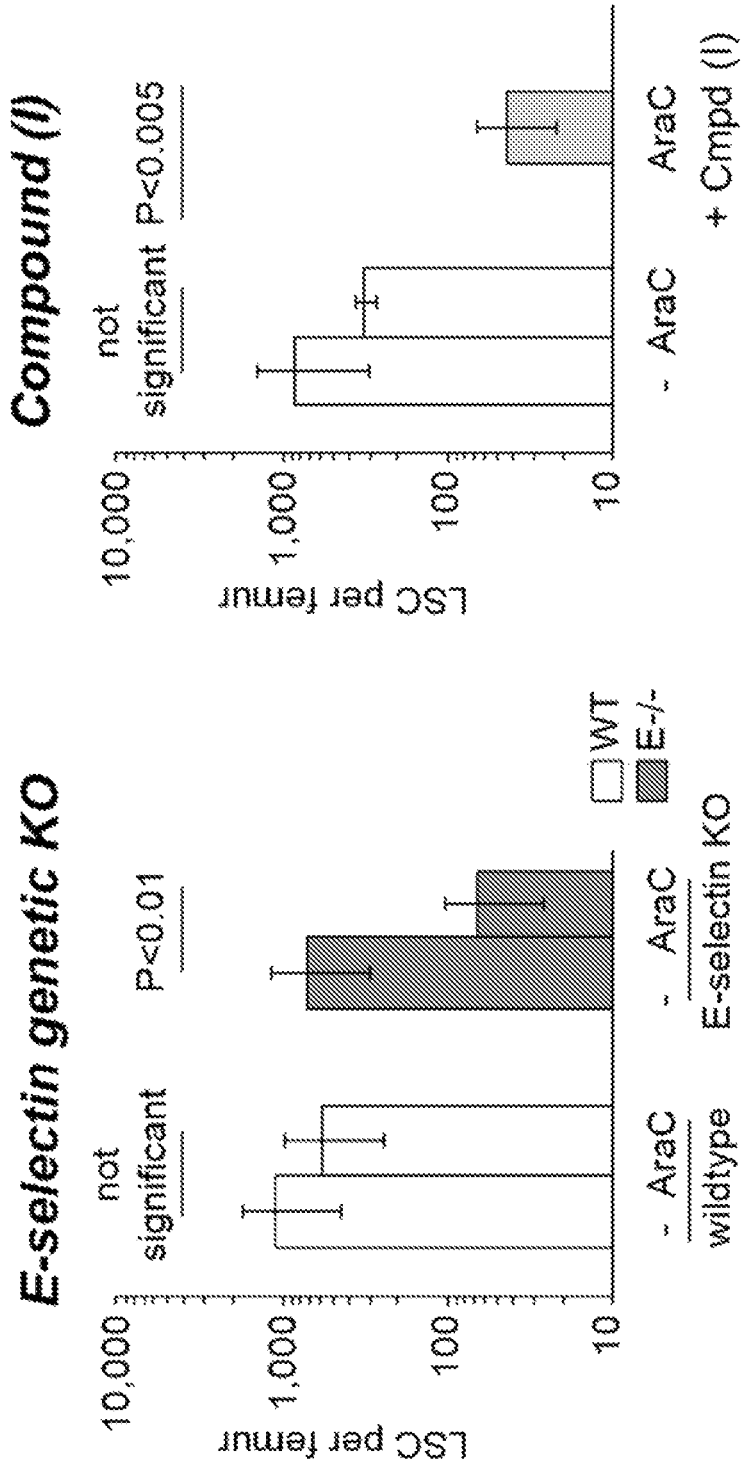
FIGS. 3A-3B illustrate the efficacy of cytarabine in E-selectin knockout mice as compared to wild-type mice (FIG. 3A), and in wild-type mice when combined with a compound of Formula (I) as compared to cytarabine ("AraC") treatment alone (FIG. 3B).

Efficacy of a Compound of Formula (I) Compared to Genetic Ablation of E-Selectin In addition to promoting the adherence of tumor cells to the endothelium, E-selectin-mediated interactions may promote leukemic stem cell ("LSC") survival following chemotherapy. Wild-type or E-selectin knock-out mice were transplanted with MLL-AF9 leukemic cells and following engraftment, treated with high dose cytarabine (2 doses of 900 mg/kg at a 12-hour interval (1800 mg/kg total)). Bone-marrow cells were harvested 24 hours after treatment and the surviving functional LSCs were quantified by limiting dilution transplantation assays in irradiated wild-type syngeneic recipients. The proportion of recipients who developed leukemia was used to calculate the number of surviving LSC by Poisson's distribution. The data demonstrated that although the absence of E-selectin had no effect on total LSC numbers per femur, the absence of E-selectin increased the sensitivity of LSC to cytarabine treatment by 20-fold (FIG. 3A).

These results suggest that E-selectin is a key vascular niche component in the bone marrow mediating LSC chemoresistance.

Wild-type mice were transplanted with MLL-AF9 leukemic cells and following engraftment, treated with high dose cytarabine (2 doses of 900 mg/kg at a 12-hour interval (1800 mg/kg total)) alone or in combination with a compound of Formula (I). Bone-marrow cells were harvested 24 hours after treatment and the surviving functional LSCs were quantified by limiting dilution transplantation assays in irradiated wild-type syngeneic recipients. The proportion of recipients who developed leukemia was used to calculate the number of surviving LSC by Poisson's distribution. The data demonstrated that inhibition of E-selectin by a compound of Formula (I) increased the sensitivity of LSC to cytarabine treatment by approximately 20-fold (FIG. 3B).

These results suggest that inhibition of E-selectin by a compound of Formula (I) increases the efficacy of cytarabine by decreasing LSC chemoresistance.

Example 5

Figure 4:
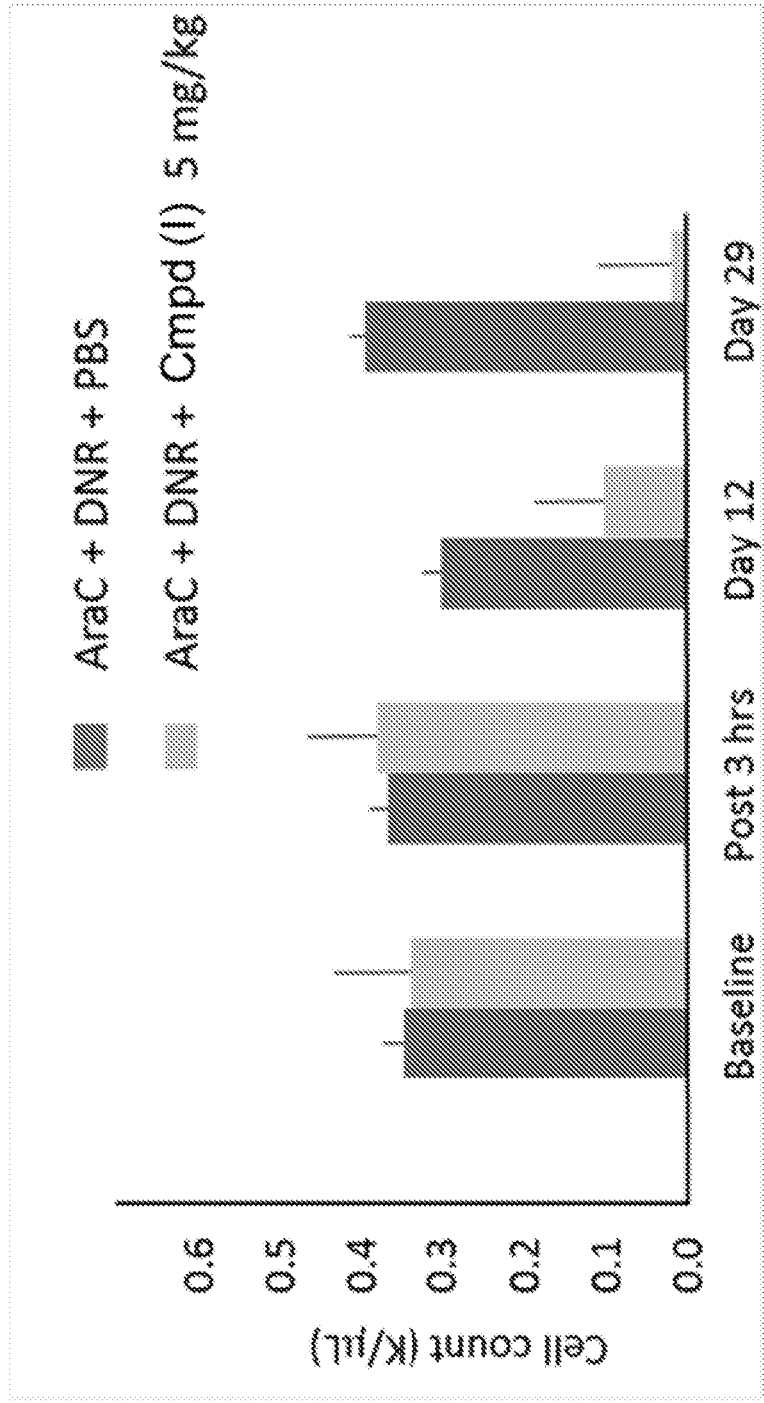
FIG. 4 illustrates circulating leukemic cell burden in mice engrafted with human AML blasts when treated with 5 mg/kg of a compound of Formula (I), cytarabine, and daunorubicin ("DNR") as compared to treatment with cytarabine and DNR.

Impact of a Compound of Formula (I) on Mice Engrafted with Human AML Blasts and Treated with Cytarabine and DNR The impact of a compound of Formula (I) on survival was evaluated in NOD-SCID mice in an orthotopic model of human AML in combination with cytarabine and DNR. A series of dose-response assessments of a compound of Formula (I) ranging from 5 mg/kg to 80 mg/kg BID (i.e., 10 mg/kg to 160 mg/kg per day) for 10 days, demonstrated 5 mg/kg BID (i.e., 10 mg/kg per day) of a compound of Formula (I) was biologically active with a marked enhancement of tumor cell chemosensitivity as determined by circulating leukemic cells (FIG. 4). However, greater doses were required to exert a therapeutic (survival) benefit in combination with cytarabine and DNR suggesting a threshold for effect.

Figure 5:
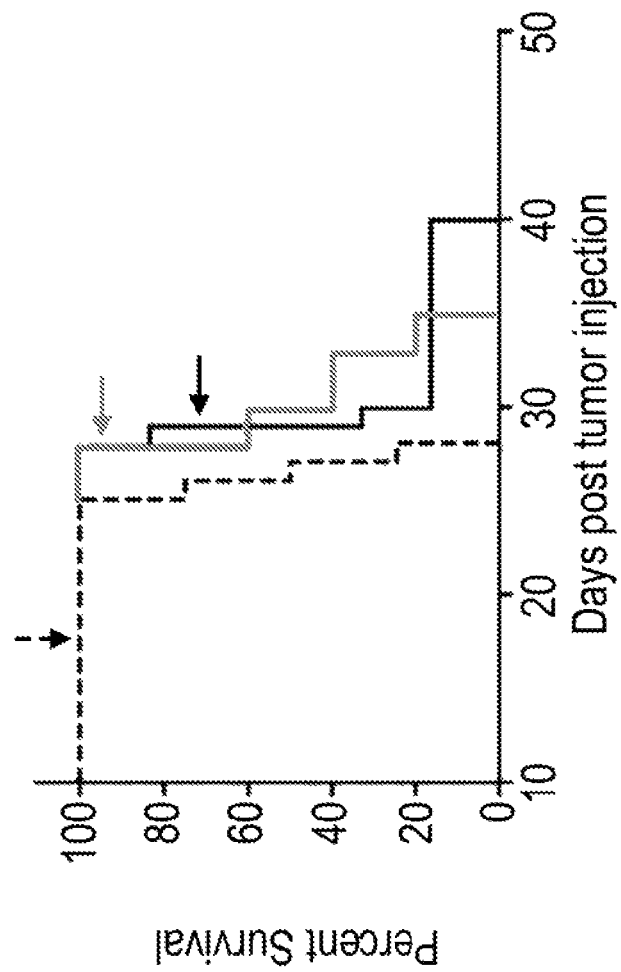
FIG. 5 illustrates survival of mice engrafted with human AML blasts when treated with a compound of Formula (I) (10 mg/kg and 40 mg/kg BID (i.e. 20 mg/kg and 80 mg/kg per day)), cytarabine, and DNR as compared to treatment with cytarabine and DNR.

10 mg/kg per day was identified as the minimally active murine dose that augmented cytarabine and DNR survival benefits. The data summarized in FIG. 5 shows a Kaplan-Meier survival plot in this tumor model following treatment with cytarabine and DNR alone, or in combination with 10 mg/kg and 40 mg/kg of a compound of Formula (I) administered BID. Mice treated with 40 mg/kg of a compound of Formula (I) also had fewer numbers of AML blasts than mice treated with cytarabine and DNR alone. In animals treated with a compound of Formula (I) and chemotherapy, the number of blasts was significantly lower in the combined compartments of the spleen and bone marrow.

These results suggest that a compound of Formula (I) when given in combination with cytarabine and DNR chemotherapy enhances tumor cell chemosensitivity, and survival in an orthotopic model of human AML.

Example 6

Compound of Formula (I) in Combination with Cytarabine and DNR Extends the Survival of Mice Bearing the Human AML Cell Line, U937

A compound of Formula (I) in combination with cytarabine/DNR chemotherapy was evaluated in the systemic U-937 AML NOD/SCID mouse survival model.

The U937 cell line was chosen because the cells express the E-selectin ligand and react with antibody HECA-452. After engraftment, mice were randomized into 4 groups (n=10/group) and treatment was initiated. The groups included a saline control group; a group administered the compound of Formula (I) at 40 mg/kg BID (i.e., 80 mg/kg per day) for 9 days, a group administered cytarabine at 300 mg/kg QD (i.e., 300 mg/kg per day) for 3 days and a single dose of DNR at 3 mg/kg; and a group administered the combined regimen of the compound of Formula (I) and chemotherapy (cytarabine and DNR).

Figure 6:
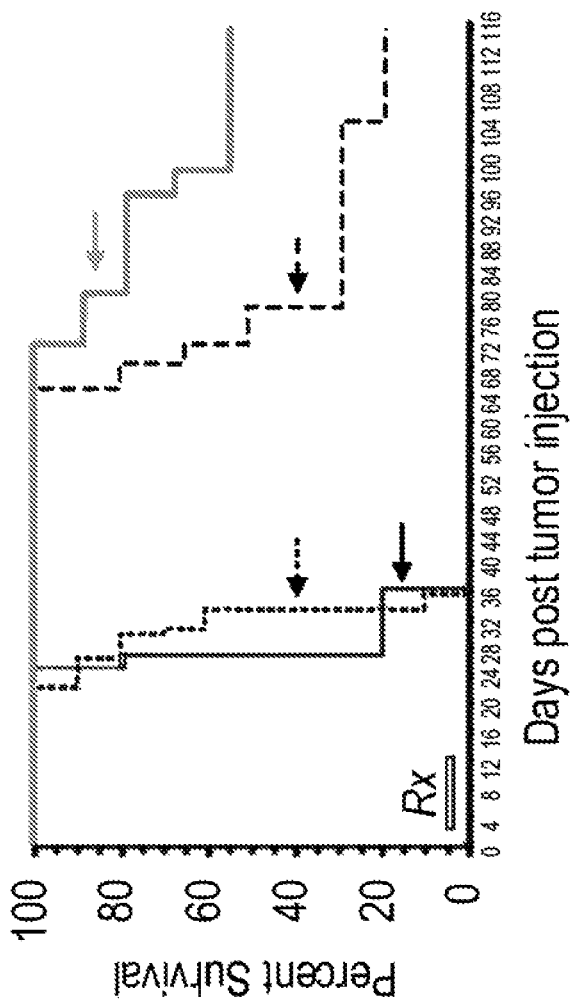
FIG. 6 illustrates survival of mice bearing the human AML cell line, U937, when given no treatment, as compared to mice treated with cytarabine and DNR, and a compound of Formula (I) (40 mg/kg BID (i.e., 80 mg/kg per day) for 9 days), cytarabine and DNR.

The combined cytarabine/DNR/compound of Formula (I) regimen resulted in a median survival time ("MST") of greater than 120 days with five animals surviving to the end of the study. This was a significant outcome compared to the control group and to monotherapy with a compound of Formula (I) (P<0.001, FIG. 6). Administration of a compound of Formula (I) alone does not extend survival beyond saline control. More importantly, the comparison of survival for the combined cytarabine/DNR/compound of Formula (I) regimen to the cytarabine/DNR regimen reached statistical significance (P=0.0341, FIG. 6).

These results suggest that survival is enhanced in a murine model of human AML when a compound of Formula (I) is administered in combination with cytarabine and DNR chemotherapy.

Example 7

Compound of Formula (I) in Combination with Cytarabine and DOX Extends the Survival of Mice Bearing the MLL-AF9-Induced AML Leukemia The impact of a compound of Formula (I) when administered adjunctively with cytarabine/DOX chemotherapy was evaluated in the syngeneic MLL-AF9 induced AML leukemia model.

Bone marrow from mice bearing MLL-AF9-inducted leukemia was harvested and enriched for kit+ cells and frozen in aliquots for subsequent transplant. Recipient mice were then injected with $3 \times 10^4$ leukemic cells 2 days after conditioning (Study day 0). Six days after leukemic injection, mice were randomized into 3 groups (n=8/group): a group administered a compound of Formula (I) at 40 mg/kg BID (i.e. 80 mg/kg per day) for 10 days, a group administered cytarabine/DOX (cytarabine at 100 mg/kg QD for 5 days, DOX at 1 mg/kg QD for 2 days), and a group administered a combined regimen of cytarabine/DOX/compound of Formula (I).

Figure 7:
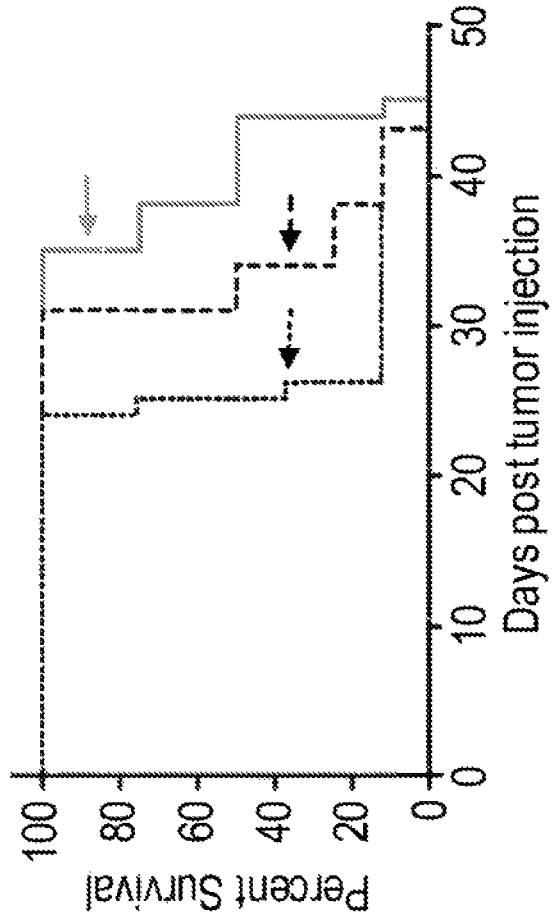
FIG. 7 illustrates survival of mice bearing MLL-AF9-induced AML leukemia when given no treatment, as compared to mice treated with cytarabine and doxorubicin ("DOX"), and mice treated with a compound of Formula (I) (40 mg/kg BID (i.e., 80 mg/kg per day) for 10 days), cytarabine, and DOX.

All treated mice progressed with tumor. Administration of a compound of Formula (I) adjunctively with cytarabine/DOX chemotherapy resulted in a MST of 41 days corresponding to a 64% increased lifespan. This was a significant outcome compared to monotherapy with a compound of Formula (I) (P=0.0009) and chemotherapy alone (30% increased lifespan, P=0.0054, FIG. 7).

These results suggest that survival is enhanced in a murine model of human AML when a compound of Formula (I) is given in combination with cytarabine and DOX chemotherapy.

Example 8

Figure 8:
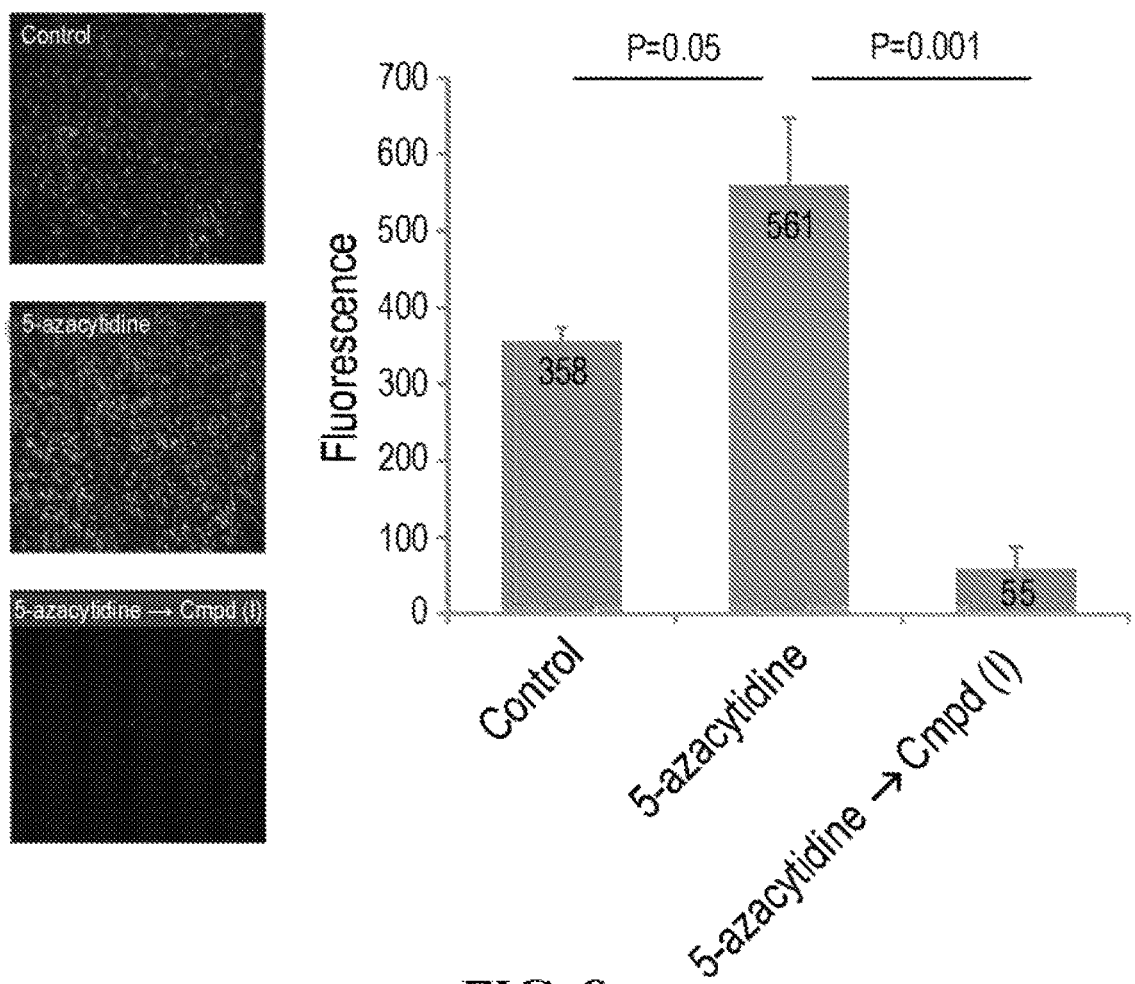
FIG. 8 illustrates adhesion of KG1 cells treated with 5-azacytidine to E-selectin-coated wells compared to KG1 cells treated with a compound of Formula (I) and 5-azacytidine, providing a graph quantifying the fluorescence demonstrated in the control cells, 5-azacytidine treated cells, and cells treated with 5-azacytidine and a compound of Formula (I).

Effects of a Compound of Formula (I) on Response to 5-Azacytidine in Systemic KG1 AML Model Data utilizing flow cytometry demonstrated that treatment of the human AML cell line KG1 with a non-cytotoxic concentration of 5-azacytidine (100 nM) lead to a 38% increase in cell binding of E-selectin-PE conjugate to cells. Further in vitro studies showed that treatment of KG1 cells with 5-azacytidine resulted in a 57% increase in static adhesion to E-selectin coated plates (compared to control treated KG1 cells, P<0.05, FIG. 8). These findings indicate that hypomethylating agents, including 5-azacytidine, may increase the adhesion of leukemic blasts in the bone marrow and therefore hinder the intended anti-leukemic effect. This could explain a source of chemoresistance, and potential for relapse, in patients treated with hypomethylating agents. Importantly, therefore, the addition of a compound of Formula (I) post-binding of KG1 cells led to an approximate 90% uncoupling of adhesion, demonstrating that the effect could be reversed with the E-selectin antagonist.

Figure 9:
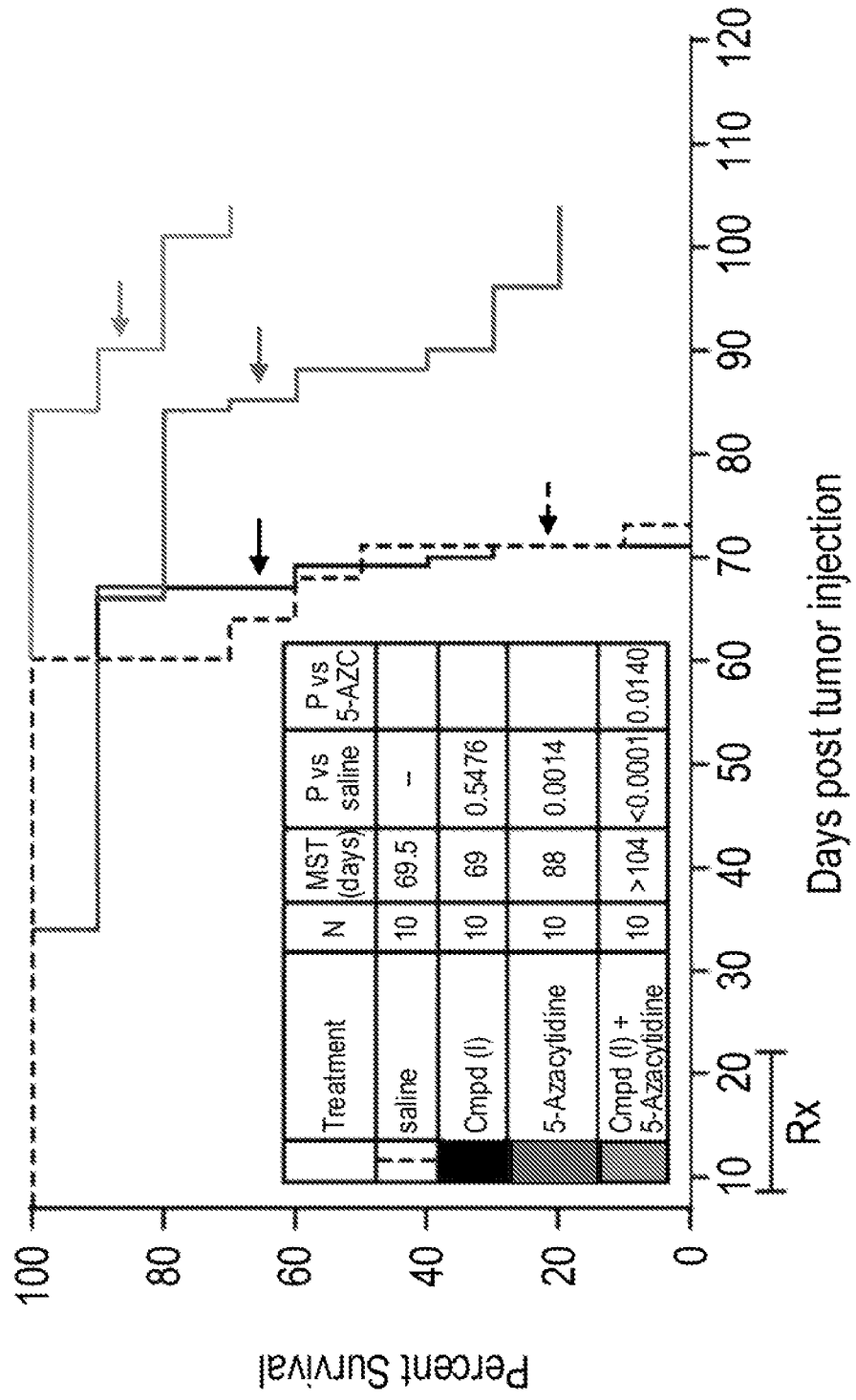
FIG. 9 illustrates survival of KG1 AML model mice when given no treatment, as comparted to mice treated with a compound of Formula (I) (40 mg/kg per day for 14 days), 5-azacytidine, or a compound of Formula (I) and 5-azacytidine.

The potential relevance of these in vitro observations was assessed in NSG female mice with pre-existing disseminated KG1 cells and treated with a compound of Formula (I) (40 mg/kg, IP, QD for 14 days), 5-azacytidine (5 mg/kg, IP, administered on days 7, 10, 13, 16, and 19 (5 doses total)), or the combination of both compounds. Under the conditions of the assay, the median survival time of mice treated with saline alone or a compound of Formula (I) was 69.5 and 69 days, respectively (FIG. 9). Administration of a compound of Formula (I) with 5-azacytidine increased median survival time beyond that obtained with 5-azacytidine treatment alone (>104 days versus 88 days; P=0.014, FIG. 9).

Collectively, these data suggest that a compound of Formula (I) does in fact attenuate the binding of AML cells by inhibiting E-selectin, complementing the antitumor activity of 5-azacytidine, and significantly improving survival above chemotherapy alone.

Example 9

Figure 10A:
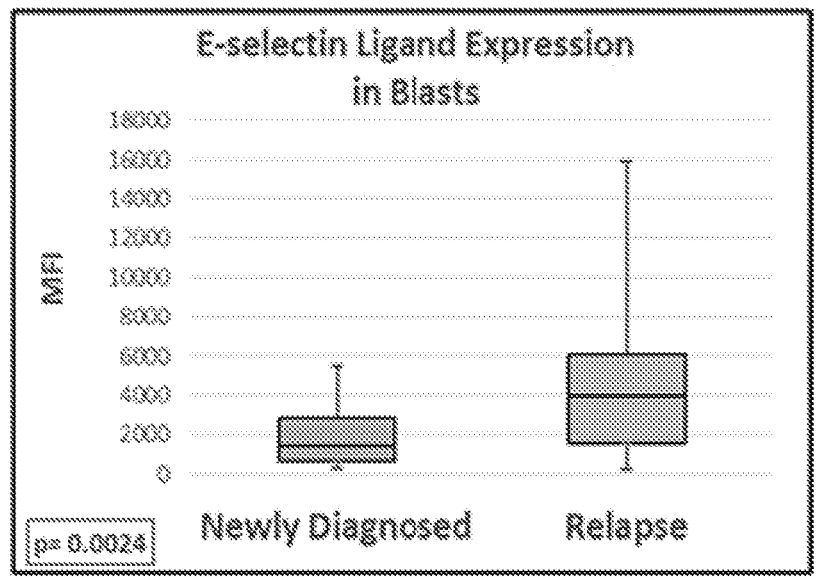
FIGS. 10A-10B illustrate E-selectin ligand binding (FIG. 10A) or sLe$^{a/x}$ binding (FIG. 10B) to AML blasts in newly diagnosed older patients (aged 60 years or older) and relapsed/refractory (R/R) leukemia patients.
Figure 10B:
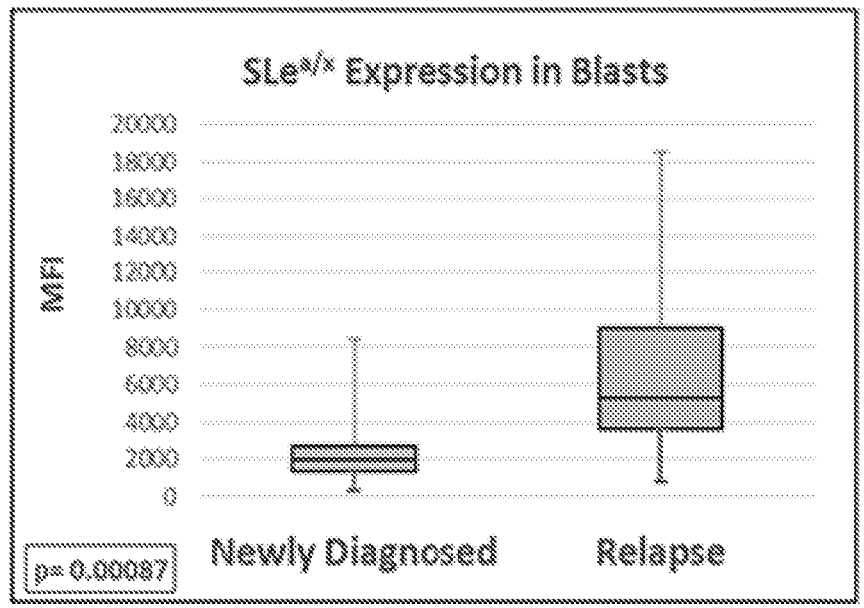

E-Selectin Ligand and sLe$^{a/x}$ Binding by AML Blasts in Newly Diagnosed Older Patients (Aged 60 Years or Older) and Relapsed/Refractory Leukemia Patients Binding of E-selectin-Ig chimeric protein (n=51 patients) or the HECA-452 antibody (n=43 patients) to AML blasts and CD34+CD38−CD123+ LSCs from older patients (aged 60 years or older) with newly diagnosed AML or relapsed/refractory (R/R) AML was assessed by flow cytometry (FIGS. 10A-10B). The HECA-452 antibody recognizes an E-selectin carbohydrate ligand shared by sLe$^a$ and sLe$^x$, which is present in P-selectin glycoprotein ligand-1 and CD44 as the glycoforms known as Cutaneous Lymphocyte-associated Antigen and Hematopoietic Cell E-selectin/L-selectin ligand, respectively. Binding in this analysis was defined as >10% of positive cells in each patient sample. AML blasts from 76% of the patients bound E-selectin-Ig chimeric protein (mean 33.6±27.4% positive cells). Mean binding of E-selectin-Ig chimeric protein by the LSC fraction from the same patients was 41.6±32.5%. The percentages of AML blasts and LSCs positive for HECA-452 (expression of sLe$^{a/x}$) were 56.3±33.9% and 63.4±34.1%, respectively.

A comparison between newly diagnosed older patients and R/R patient blasts demonstrated the mean fluorescence intensities of E-selectin-Ig chimeric protein and HECA-452 binding were both higher in R/R patients than in newly diagnosed older patients (P=0.0024 and 0.00087, respectively, FIGS. 10A-10B).

These results suggest that an increased density of the E-selectin ligand expressed on the surface of AML blasts is associated with relapse.

Example 10

Pharmacokinetics of Weight-Based Doses

Three cohorts of 6-7 human subjects with acute myeloid leukemia (AML) each received a total of 15 infusions of 5, 10, or 20 mg/kg/dose over 8 days with a nominal infusion duration of 20 minutes. The first dose of a compound of Formula (I), was administered 24 hours±1 hour prior to the first dose of MEC (mitoxantrone, etoposide, and cytarabine) induction chemotherapy as a sentinel dose to evaluate the effect of the compound of Formula (I) alone, and then every 12 hours±1 hour on chemotherapy days, starting 2 hours prior to chemotherapy. Hence, the interval between the first and second doses of compound of Formula (I) was approximately 24 hours. MEC chemotherapy was administered on Days 2-6. Samples were obtained pre-dose, on Day 1, Day 3, Day 8, Day 9, and Day 10 (where Day 1 refers to the first day of dosing with a compound of Formula (I)).

| Metric | Dose (mg/kg/ dose) | N | Mean | SD | Median | Min | Max |
|---|---|---|---|---|---|---|---|
| Cmax | 5 | 6 | 38.48 | 14.18 | 36.30 | 22.47 | 62.41 |
| (μg/ml) | 10 | 7 | 79.62 | 17.95 | 76.21 | 56.94 | 110.29 |
|  | 20 | 6 | 166.72 | 43.03 | 152.72 | 129.13 | 249.42 |
| AUC | 5 | 6 | 5.21 | 1.51 | 4.83 | 3.36 | 7.35 |
| (μg/ml · | 10 | 7 | 9.63 | 4.24 | 9.63 | 5.55 | 17.96 |
| days) | 20 | 6 | 20.43 | 9.23 | 19.33 | 10.40 | 36.34 |
| Fx of | 5 | 6 | 0.490 | 0.105 | 0.459 | 0.369 | 0.671 |
| Time > | 10 | 7 | 0.582 | 0.205 | 0.571 | 0.381 | 1.000 |
| $IC_{50}$ | 20 | 6 | 0.776 | 0.227 | 0.803 | 0.442 | 1.000 |
| Fx of | 5 | 6 | 0.222 | 0.090 | 0.210 | 0.096 | 0.357 |
| Time > | 10 | 7 | 0.404 | 0.233 | 0.377 | 0.217 | 0.907 |
| $IC_{90}$ | 20 | 6 | 0.612 | 0.255 | 0.577 | 0.302 | 1.000 |

* Values are determined for the period starting at dose 13 and ending at dose 15. To determine AUC for the entire 15-dose period, multiply these values by 7.5.

These results show that increased weight-based daily doses of up to 40 mg/kg (i.e. 20 mg/kg per dose) are associated with an increase in Cmax, AUC, and the fraction of the dosing period in which Cp was greater than each of $IC_{50}$ and $IC_{90}$.

Example 11

Pharmacokinetics of Fixed Doses

Simulations were performed to evaluate systemic exposure (area-under-the-curve ("AUC") and maximal plasma concentration ("Cmax")) of a compound of Formula (I) and the fraction of the dosing interval in which the Cp of the compound of Formula (I) was higher than the human E-selectin $IC_{50}$ (3184 ng/ml) or $IC_{90}$ (7535 ng/ml) for fixed doses of 400 mg per dose, 800 mg per dose, and 1600 mg per dose. Simulations were based on the post hoc parameters for each subject in Example 10, their creatinine clearance, and a fixed dose matched to the nominal dose. Subjects assigned to the 5, 10, and 20 mg/kg per dose groups (i.e., 10, 20, and 40 mg/kg per day) were assigned to the 400, 800, and 1600 mg per dose groups (i.e., 800, 1600, and 3200 mg/kg per day), respectively.

For all simulations, the dosing regimen was fifteen doses infused over 20 minutes at intervals of 12 hours; samples were simulated at intervals of 20 minutes over 7.5 days. For each simulated subject, Cmax was determined by inspection of the data; AUC for the final day in which two doses were administered (doses 13 and 14) was determined using linear trapezoids. The fraction of each interval in which Cp exceeded each of $IC_{50}$ and $IC_{90}$ was determined for that same time period. All calculations were performed with R.

| Metric | Dose (mg/ dose) | N | Mean | SD | Median | Min | Max |
|---|---|---|---|---|---|---|---|
| Cmax | 400 | 6 | 42.09 | 8.54 | 40.39 | 33.05 | 55.91 |
| (μg/ml) | 800 | 7 | 71.22 | 14.45 | 64.72 | 54.95 | 93.27 |
|  | 1600 | 6 | 161.42 | 42.03 | 167.09 | 103.39 | 224.96 |
| AUC | 400 | 6 | 5.76 | 0.75 | 5.63 | 4.95 | 6.89 |
| (μg/ml · | 800 | 7 | 8.52 | 3.51 | 7.41 | 5.85 | 15.90 |
| days)* | 1600 | 6 | 19.85 | 8.75 | 19.93 | 8.68 | 32.77 |
| Fx of | 400 | 6 | 0.526 | 0.052 | 0.501 | 0.489 | 0.616 |
| Time > | 800 | 7 | 0.559 | 0.204 | 0.501 | 0.395 | 1.000 |

-continued

| Metric | Dose (mg/ dose) | N | Mean | SD | Median | Min | Max |
|---|---|---|---|---|---|---|---|
| $IC_{50}$ | 1600 | 6 | 0.771 | 0.236 | 0.788 | 0.413 | 1.000 |
| Fx of | 400 | 6 | 0.258 | 0.041 | 0.241 | 0.219 | 0.318 |
| Time > | 800 | 7 | 0.371 | 0.211 | 0.285 | 0.231 | 0.837 |
| $IC_{90}$ | 1600 | 6 | 0.610 | 0.266 | 0.570 | 0.272 | 1.000 |

*Values are determined for the period starting at dose 13 and ending at dose 15. To determine AUC for the entire 15-dose period, multiply these values by 7.5.

These results show that increased fixed doses up to 3200 mg per day (i.e. 1600 mg per dose BID) are associated with an increase in Cmax, AUC, and the fraction of the dosing period in which Cp was greater than each of $IC_{50}$ and $IC_{90}$.

Example 12

Plasma Soluble E-Selectin Concentration-Time Curve

Plasma sE-selectin was quantified using a commercially available sandwich format ELISA assay, in which a monoclonal antibody specific for sE-selectin has been pre-coated onto a microplate (Human sE-Selectin Platinum ELISA kit, eBioscience, cat. no. BMS205). Standards, samples and controls were pipetted into the wells of the microplate where they bind to the antibodies coated on the microplate. After a wash step, an HRP-conjugated anti-human sE-selectin antibody was added to the wells to bind the sE-selectin captured by the first antibody. After washing the plate wells to remove unbound HRP-conjugated anti-human sE-selectin antibody, a substrate solution reactive with HRP is added to the wells. Colored product formed in proportion to the amount of human sE-selectin present in the sample or standard. The color-producing reaction was stopped by addition of acid and absorbance of each well was measured at 450 nm. Six human serum samples from healthy donors served as the quality control samples. In addition, two control lyophilized plasma samples (high and low) included with the assay kit were also added to each run.

Figure 11:
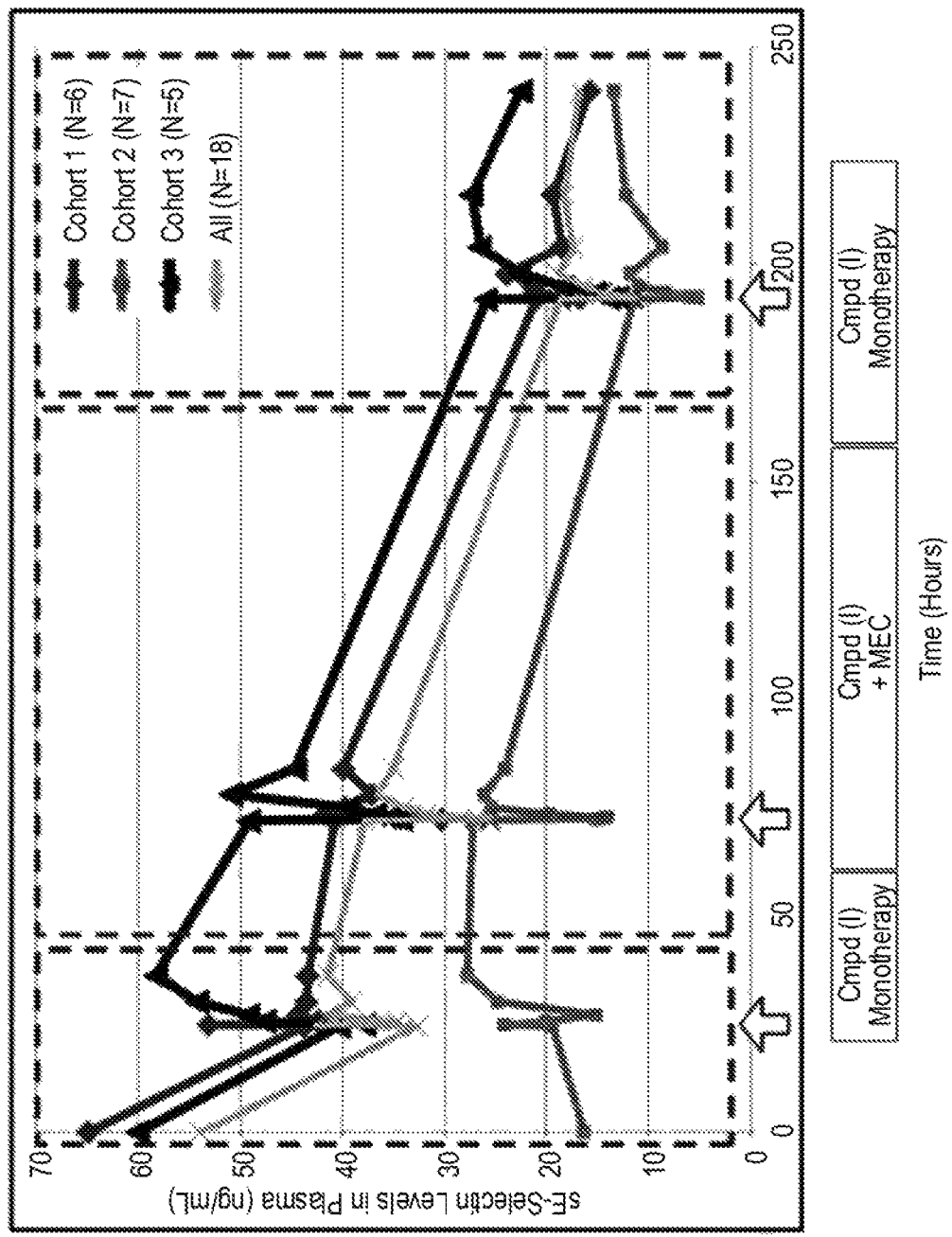
FIG. 11 illustrates plasma soluble E-selectin levels across an 8-day treatment period in human subjects treated with various levels of a compound of Formula (I), and MEC chemotherapy. Subjects were divided into three cohorts for the eight-day study. On day 1, subjects received a single dose of a compound of Formula (I), days 2-6 each comprised MEC treatment combined with two doses of a compound of Formula (I), and days 7-8 each comprised two doses of a compound of Formula (I). Cohort 1 received doses of 5 mg/kg of a compound of Formula (I) (i.e. 5 mg/kg on day 1; 5 mg/kg BID (10 mg/kg per day) on days 2-8), cohort 2 received 10 mg/kg doses of a compound of Formula (I) (i.e. 10 mg/kg on day 1; 10 mg/kg BID (20 mg/kg per day) on days 2-8), and cohort 3 received 20 mg/kg doses of a compound of Formula (I) (i.e. 20 mg/kg on day 1; 20 mg/kg BID (400 mg/kg per day) on days 2-8). The decrease from baseline to Day 8 was highly significant (P<0.0001) with no dose response.

Plasma soluble E-selectin levels decreased over the treatment period in all dose groups. This response was seen both in mean levels and Area-Under-Effect-Curve ("AUEC"). Decrease from baseline to Day 8 (at the end of 6 days of treatment with a compound of Formula (I), given concurrently with MEC chemotherapy) was highly significant (P<0.0001) with no dose response. FIG. 11 illustrates decreasing mean levels of plasma soluble E-selectin over the treatment period in all dose groups, where doses were BID (i.e., the 5, 10, and 20 mg/kg "Per Dose" amounts of a compound of Formula (I) correspond to dosages of 10, 20, and 40 mg/kg per day, respectively).

| Per Dose (mg/ kg) | Subject | AUEC (hrxng/mL) | | | Percent Change from Day 1 | |
|---|---|---|---|---|---|---|
| | | Day 1 | Day 3 | Day 8 | Day 3 | Day 8 |
| 5 | IE0010001 | 563.47 | 494.30 | 440.68 | −12.28 | −21.79 |
|  | US0020001 | 1,605.18 | 1,445.26 | 728.47 | −9.96 | −54.62 |
|  | US0030001 | 339.27 | 275.71 | 156.25 | −18.74 | −53.95 |
|  | US0050002 | 328.40 | 332.11 | 161.11 | 1.13 | −50.94 |
| 10 | US0030003 | 230.35 | 185.98 | 158.91 | −19.26 | −31.01 |
|  | US0040001 | 338.36 | 313.04 | 168.71 | −7.48 | −50.14 |
|  | US0040003 | 707.63 | 981.09 | 218.03 | 38.64 | −69.19 |

-continued

| Per Dose (mg/kg) | Subject | AUEC (hr×ng/mL) | | | Percent Change from Day 1 | |
|---|---|---|---|---|---|---|
| | | Day 1 | Day 3 | Day 8 | Day 3 | Day 8 |
| | US0060001 | 325.19 | 298.31 | 25.51 | −8.26 | −92.15 |
| | US0060003 | 269.90 | 202.99 | 103.74 | −24.79 | −61.57 |
| 20 | US0060004 | 2,206.19 | 1,743.61 | 956.57 | −20.97 | −56.64 |
| | US0060005 | 750.41 | 632.82 | 294.47 | −15.67 | −60.76 |
| | US0060006 | 202.19 | 163.18 | 31.49 | −19.30 | −84.43 |

These results show that levels of sE-selectin decreased across all tested doses of the compound of Formula (I).

Example 13

Clinical Outcomes—Relapsed/Recovery Subjects "Phase 1"

Three cohorts of 6-7 human subjects with relapsed/refractory type acute myeloid leukemia (AML) each received a total of 15 infusions of 5, 10, or 20 mg/kg/dose of the compound of Formula (I), administered as the sodium salt, over 8 days with a nominal infusion duration of 20 minutes. The nominal infusion duration of 20 minutes was constant across cohorts (e.g., a slower infusion rate was used for the administration of the 5 mg/kg/dose arm than for the 10 mg/kg/dose arm). The formulation for the infusion solution was as follows:

| Component | Target Concentration |
|---|---|
| Compound of Formula (I) | 50 mg/mL |
| NaCl | 6.0 mg/mL |
| 10 mM TRIS buffer solution | 1.2 mg/mL |
| Water for injection | Quantity sufficient to volume |

The first dose of a compound of Formula (I) was administered 24 hours±1 hour prior to the first dose of MEC (mitoxantrone, etoposide, and cytarabine) induction chemotherapy as a sentinel dose to evaluate the effect of the compound of Formula (I) alone (i.e., a single dose of 5, 10, or 20 mg/kg the day before the first chemotherapy day). The compound of Formula (I) was then administered every 12 hours±1 hour on chemotherapy days, starting 2 hours prior to chemotherapy (i.e., 10, 20, or 40 mg/kg per day on chemotherapy days). Hence, the interval between the first and second dose of the compound of Formula (I) was approximately 24 hours. MEC chemotherapy was administered on Days 2-6.

The clinical outcome for each subject was assessed at the time of count recovery following completion of induction chemotherapy. Subjects were assigned to one of four response groups: complete remission ("CR"); complete remission with incomplete count recovery ("CRi"); morphologic leukemia-free state ("MLFS"); persistent disease ("PD"). Complete remission was defined as bone marrow blasts <5%; absence of circulating blasts and blasts with Auer rods; absence of extramedullary disease; ANC ≥1.0× $10^9$/L and platelets ≥100,000× $10^9$/L. Complete remission with incomplete recovery was defined as: all CR criteria except for residual neutropenia (<1.0× $10^9$/L) or thrombocytopenia (<100,000× $10^9$/L). Morphologic leukemia-free state was defined as: bone marrow blasts <5%; absence of blasts with Auer rods; absence of extramedullary disease; no hematologic recovery required. Persistent disease was defined as: bone marrow blasts >5%.

| Outcome, Reported as n (%) | 5 mg/kg/ dose | 10 mg/kg/ dose | 20 mg/kg/ dose | Total |
|---|---|---|---|---|
| N Completing Induction Period | 6 | 7 | 6 | 19 |
| Response | | | | |
| CR + CRi | 3 (50) | 5 (71) | 1 (17) | 9 (47) |
| Complete Remission (CR) | 2 (33) | 5 (71) | 1 (17) | 8 (42) |
| CR with incomplete recovery (CRi) | 1 (17) | 0 | 0 | 1 (5) |
| CR + CRi + MLFS + PR | 4 (67) | 5 (71) | 1 (17) | 10 (53) |
| Morphologic Leukemia-Free State (MLFS) | 1 (17) | 0 | 0 | 1 (5) |
| Persistent Disease | 2 (33) | 2 (29) | 5 (83) | 9 (47) |

| AML Subgroup | CR Rate n (%) |
|---|---|
| N Completing Induction Period | 19 |
| Primary Refractory | 4/7 (57%) |
| Relapsed | 5/12 (20%) |
| Relapsed <6 months | 1/5 (20%) |
| Relapsed 6-12 months | 1/4 (25%) |
| Relapsed >12 months | 3/3 (100%) |
| Age <60 years | 7/14 (50%) |
| Age ≥60 years | 2/5 (60%) |
| Cytogenetics | |
| Favorable risk | 0 |
| Intermediate risk | 5/7 (71%) |
| Unfavorable risk | 4/12 (33%) |
| FLT3-ITD mutated | 1/2 (50%) |
| Extramedullary disease | 1/1 (100%) |

These results demonstrate a response rate of almost 50% (CR/CRi) after a single course of induction treatment with MEC and a compound of Formula (I). This rate is higher than expected response rate, given the high-risk cytogenetic and other disease features of the study population, when compared to historical controls of similar populations treated with MEC (see Feldman, et al. Phase III randomized multicenter study of a humanized anti-CD33 monoclonal antibody, lintuzumab, in combination with chemotherapy, versus chemotherapy alone in patients with refractory or first-relapsed acute myeloid leukemia. J. Clin. Oncol. 2005 Jun. 20; 23(18):4110-6; Greenberg, et al. Mitoxantrone, etoposide, and cytarabine with or without valspodar in patients with relapsed or refractory acute myeloid leukemia and high-risk myelodysplastic syndrome: a phase III trial (E2995). J. Clin. Oncol. 2004 Mar. 15; 22(6): 1078-86.)

Example 14

Exposure-Response Analysis for Efficacy

To generate exposure metrics for the analyses in Example 14 and Example 15, a Pop-PK analysis, based on sampling of plasma concentrations (Cp) of the compound of Formula (I) during induction treatment, was conducted to identify an appropriate PK model, key covariates of the model, and to generate post hoc population PK metrics for all patients sampled for PK. The Pop-PK analysis comprised 59 subjects, 46 subjects diagnosed with relapsed/refractory (R/R) AML who were administered a compound of Formula (I) with MEC chemotherapy and 13 older subjects (aged 60 years or older) with newly diagnosed AML who were administered a compound of Formula (I) with 7+3 chemotherapy. Pop-PK modeling identified a three compartment model with renal function as the only significant covariate.

For Example 14, Exposure-Response ("E-R") analysis evaluating efficacy measures against PK metrics was conducted using clinical response efficacy data from the 46 R/R AML subjects. R/R AML subjects were administered MEC chemotherapy and 5, 10, and 20 mg/kg of a compound of Formula (I) BID (i.e. 10, 20, and 40 mg/kg per day).

Figure 12A:
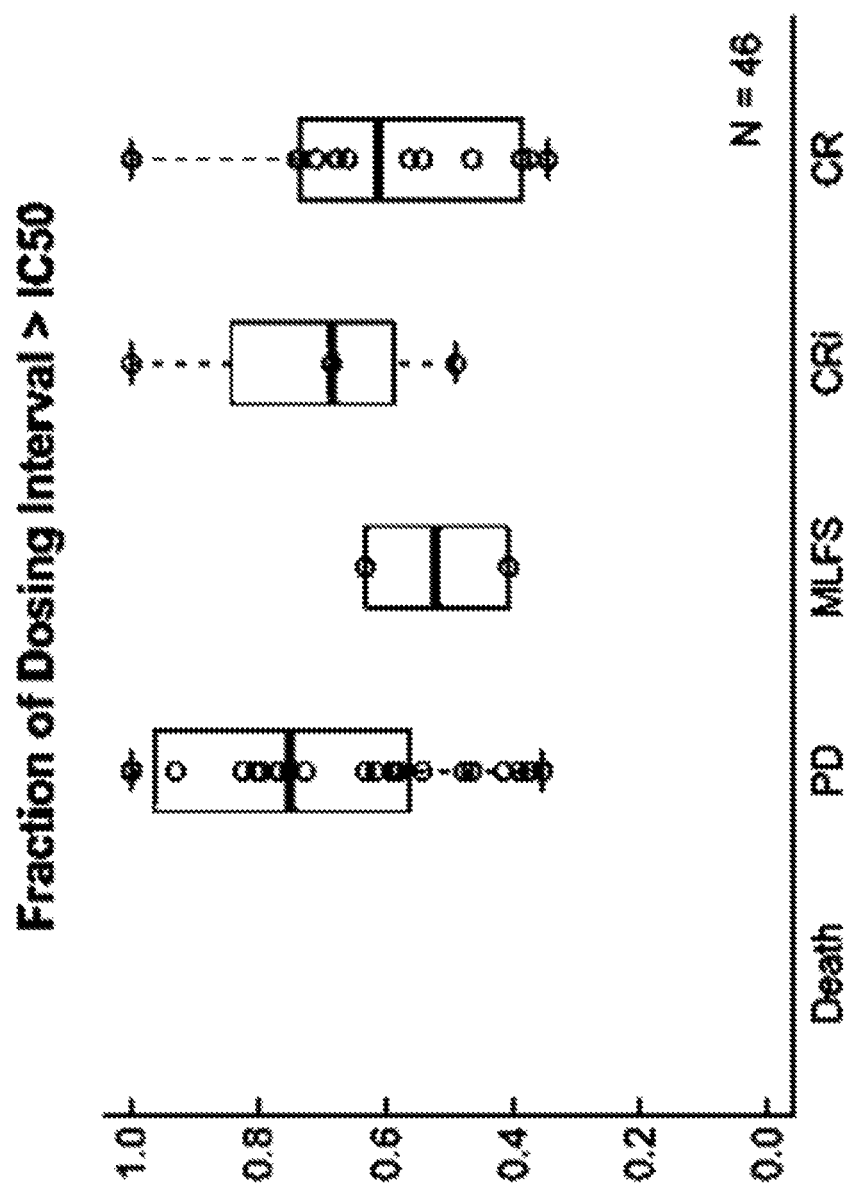
FIGS. 12A-12D illustrate metrics quantifying exposure-response to a compound of Formula (I), during treatment across clinical response categories.
Figure 12B:
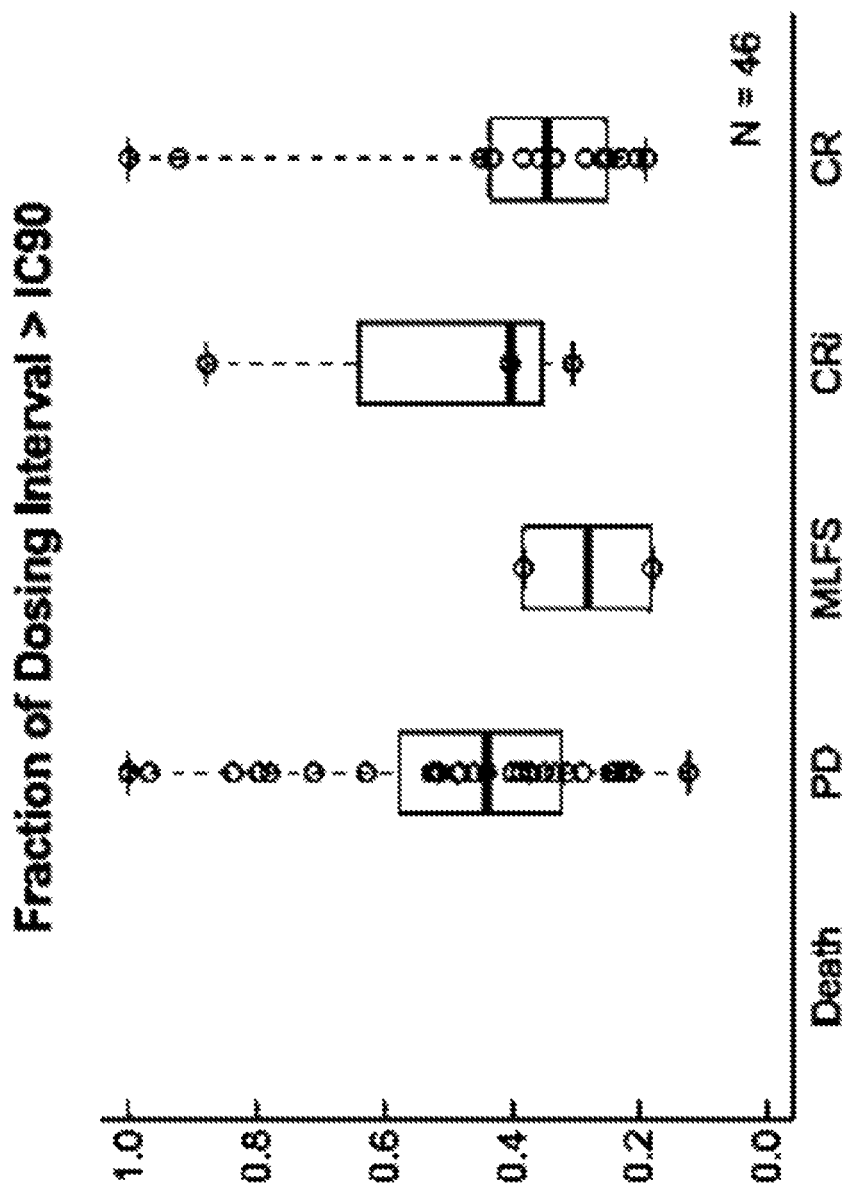
Figure 12C:
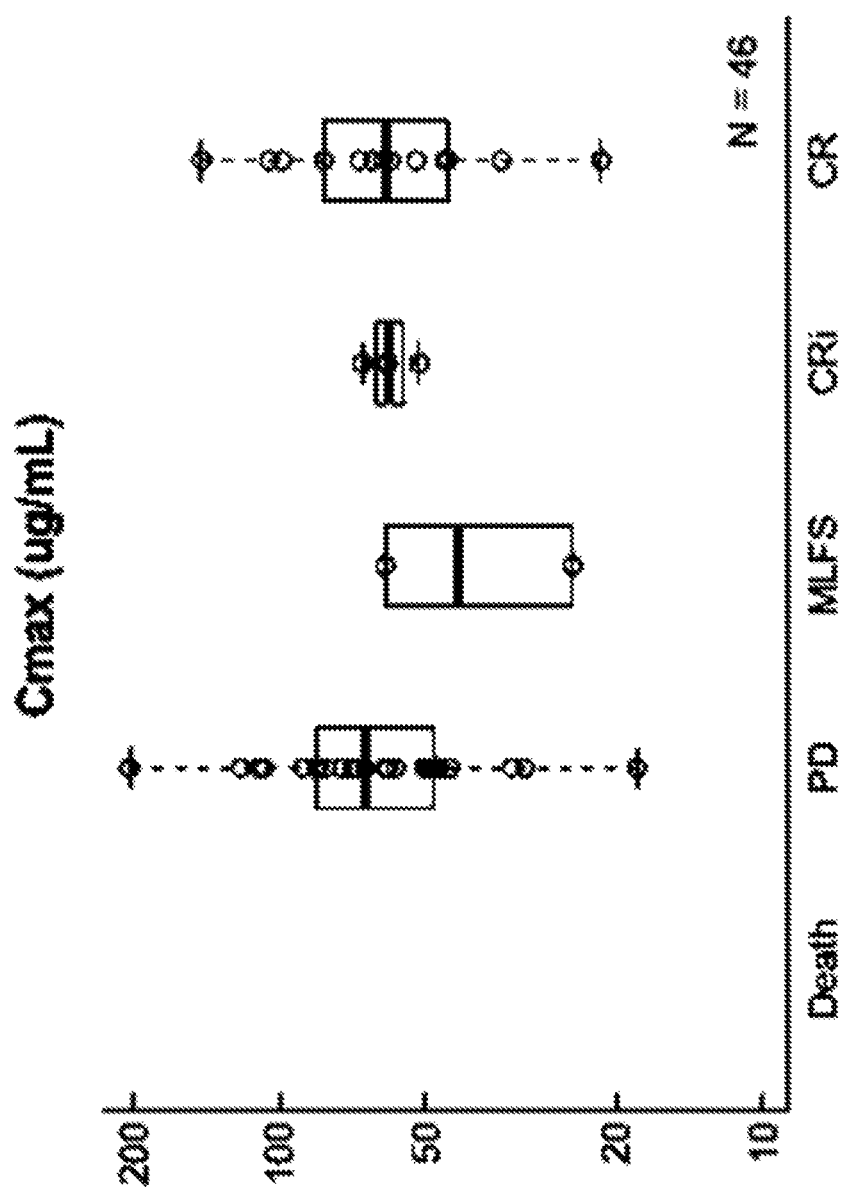
Figure 12D:
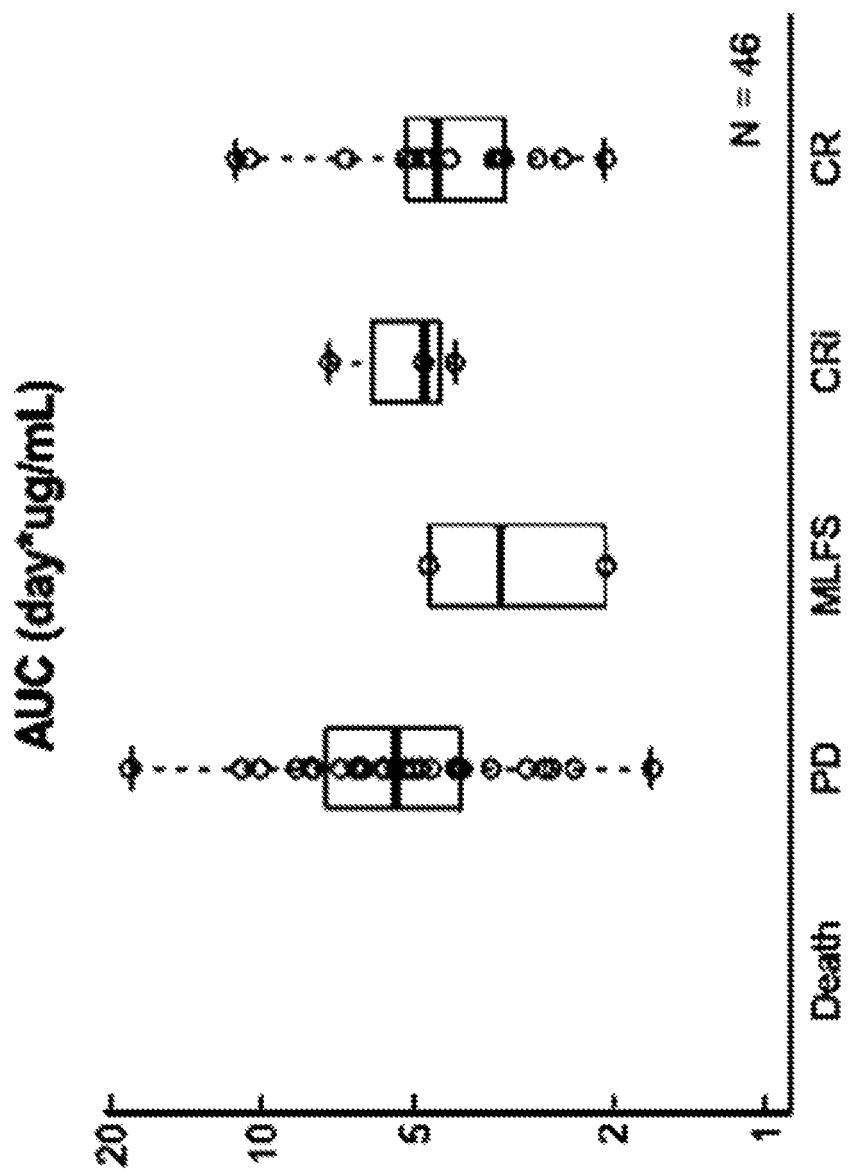

Exposure metrics were generated using the Pop-PK model described above. For each subject the Cp profile for during a single dosing interval at steady state, was examined to determine the fraction of the dosing interval during which Cp was above $IC_{50}$ (3.184 µg/mL) (FIG. 12A) and $IC_{90}$ (7.535 µg/mL) (FIG. 12B), the Cmax (FIG. 12C), and AUC (determined using linear trapezoids) (FIG. 12D) during that interval.

Using clinical measures of efficacy described in Example 13 each subject was assigned to one of five clinical response categories: CR, CRi, MLFS, PD, and death. These were plotted against the measures of exposure and evaluated for trends suggestive of exposure response. FIGS. 12A-12D plot exposure individual metrics against each category of efficacy response. In addition, box and whisker plots to illustrate the minimum, 25th percentile, median, 75th percentile and maximum exposure metric in each category were added to the graphics. Inspection of FIGS. 12A-12D reveals significant overlap in all exposure-response metrics relating to remission for those subjects attaining CR and those with PD.

Example 15

Exposure-Response Analysis for Adverse Events

For Example 15, Exposure-Response ("E-R") analysis evaluating adverse events against PK metrics was conducted. The sample population for Example 15 included 53 subjects with relapsed/refractory (R/R) AML and 25 older subjects (aged 60 years or older) with newly diagnosed AML. R/R AML subjects were administered MEC chemotherapy and 5, 10, and 20 mg/kg of a compound of Formula (I) BID (i.e., 10, 20, and 40 mg/kg per day). The older subjects (aged 60 years or older) with newly diagnosed AML were administered 7+3 chemotherapy and 10 mg/kg of a compound of Formula (I) BID (i.e., 20 mg/kg per day).

Exposure metrics for the adverse events ("AE") analysis were generated using the same Pop-PK model described in Example 14. For each subject, the Cp profile during each 24-hour interval (midnight to midnight) was examined to determine Cmax and AUC (determined using linear trapezoids) during that interval. Cumulative AUC was determined through each study day. For each metric/day combination, percentile rankings and normalized values were determined. For example, the median of Day 6 AUC values was determined, and normalized values were obtained by dividing each value by the median. In addition, these Day 6 AUC values were ranked, and then multiplied by 100% divided by the number of values to obtain a percentile value.

Figure 13A:
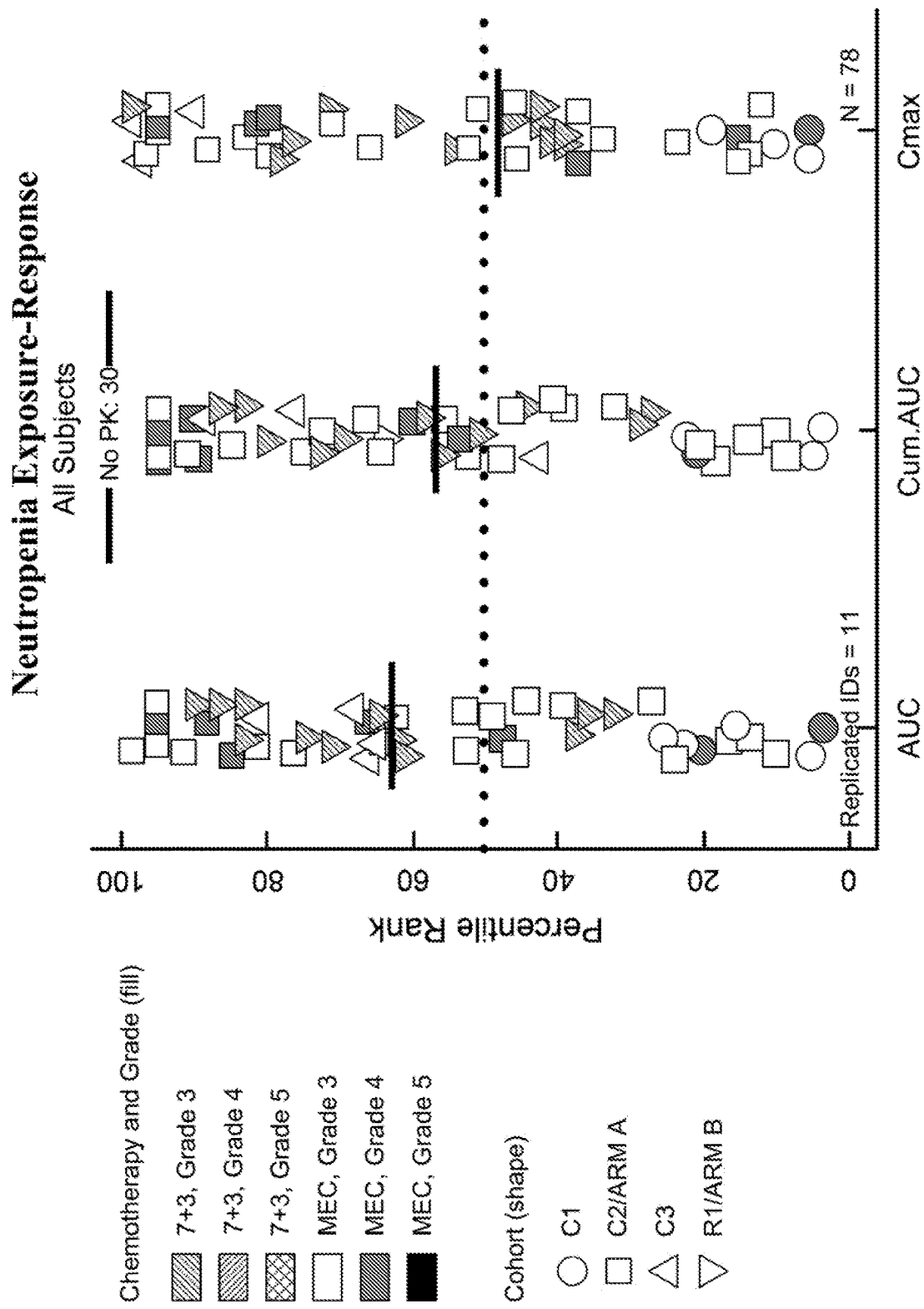
FIGS. 13A-13D illustrate adverse events ("AEs") plotted against exposure to a compound of Formula (I) during treatment. Percentile rankings (left graphs) and normalized values (right graphs) of each subject's calculated AUC, cumulative AUC, and Cmax are reported. AEs identified for E-R analyses were: neutropenia (FIGS. 13A and 13B), thrombocytopenia (FIGS. 13C and 13D), febrile neutropenia (FIGS. 13E and 13F), infection (FIGS. 13G and 13H), mucositis (FIGS. 13I and 13J), and anemia (FIGS. 13K and 13L). If a subject experienced the event twice, they are shown twice in the figures, as indicted by "Replicate IDs." The number of subjects who did not have evaluable PK data is annotated as "No PK," and those subjects' data are not shown in the graphs.
Figure 13B:
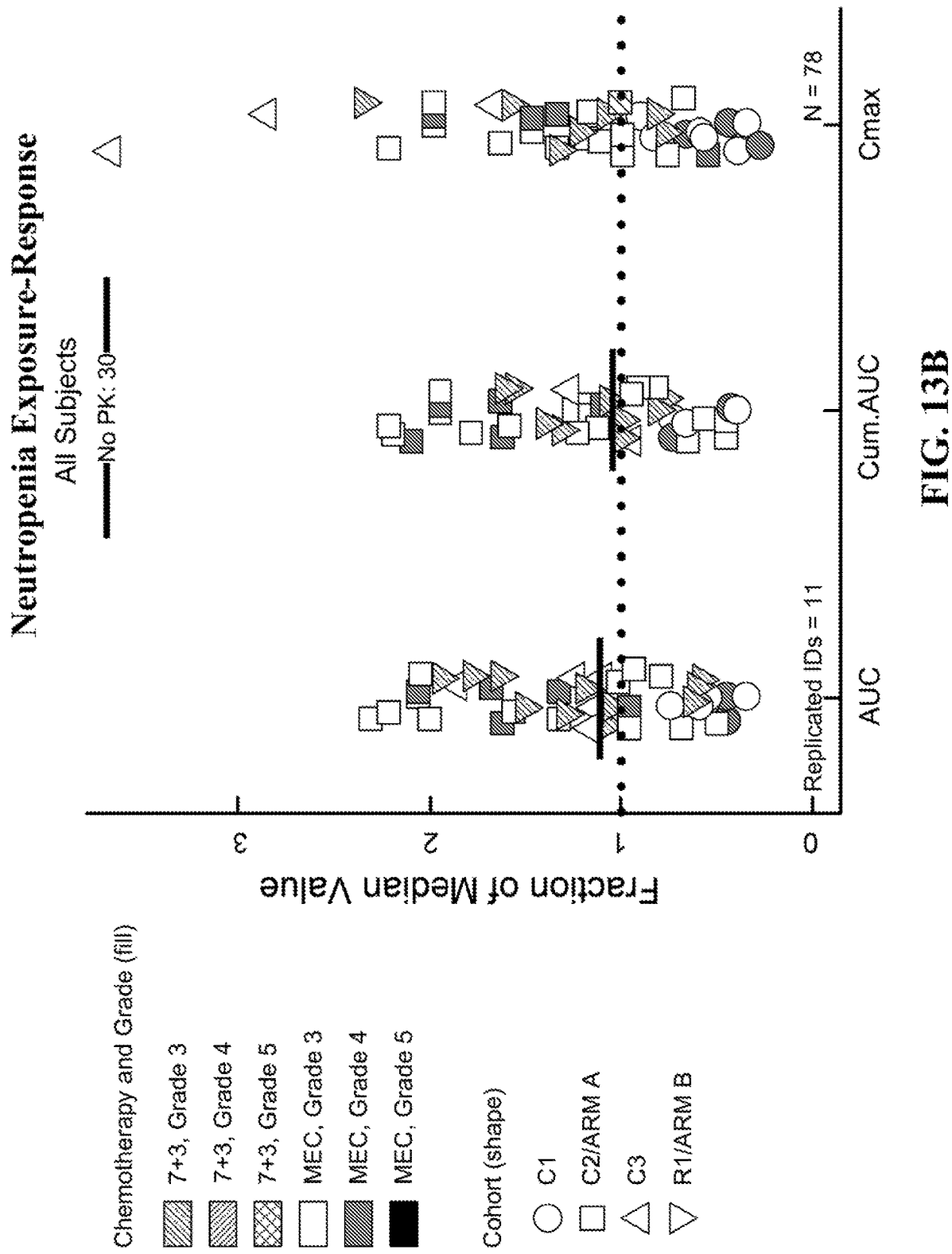
Figure 13C:
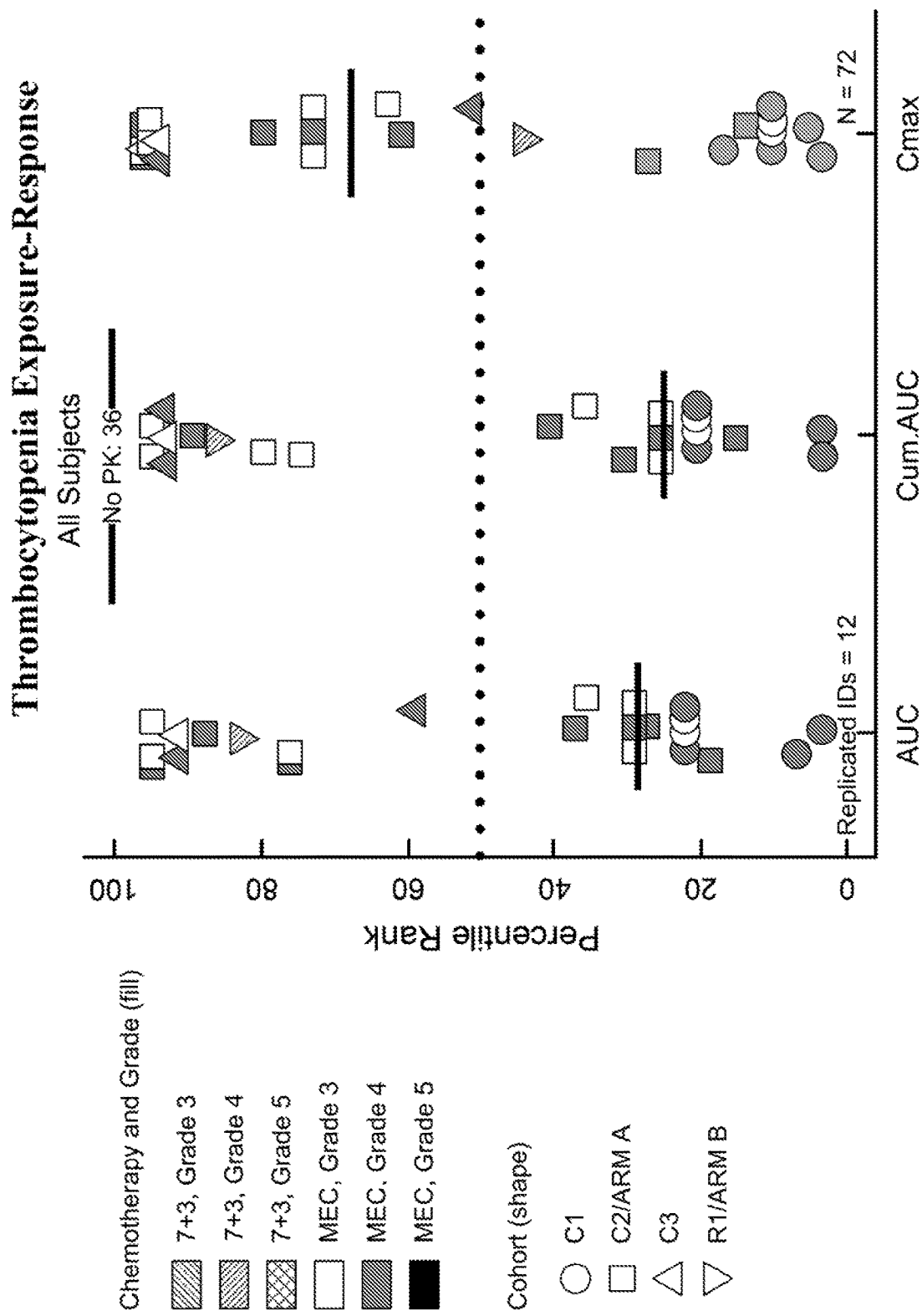
Figure 13D:
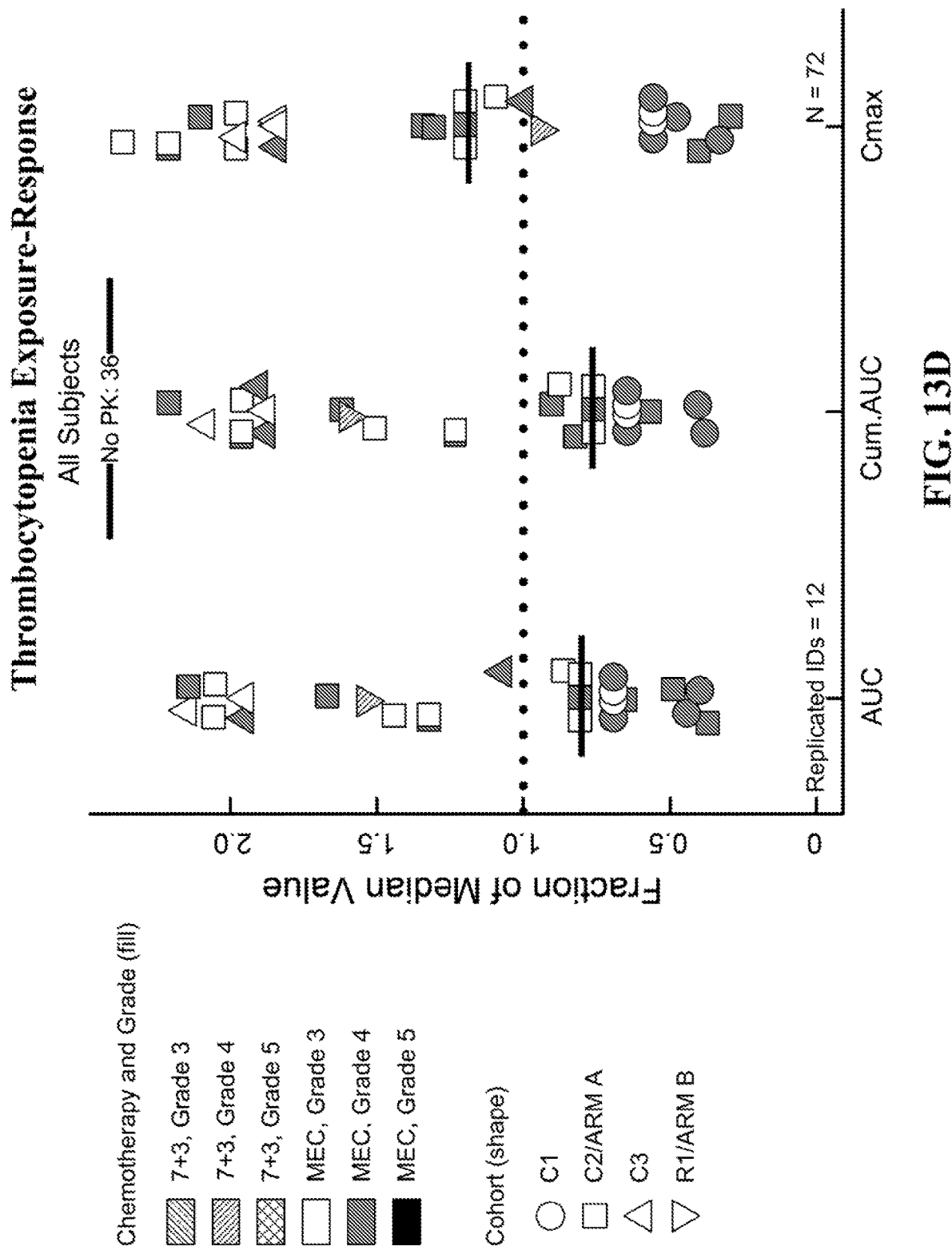
Figure 13E:
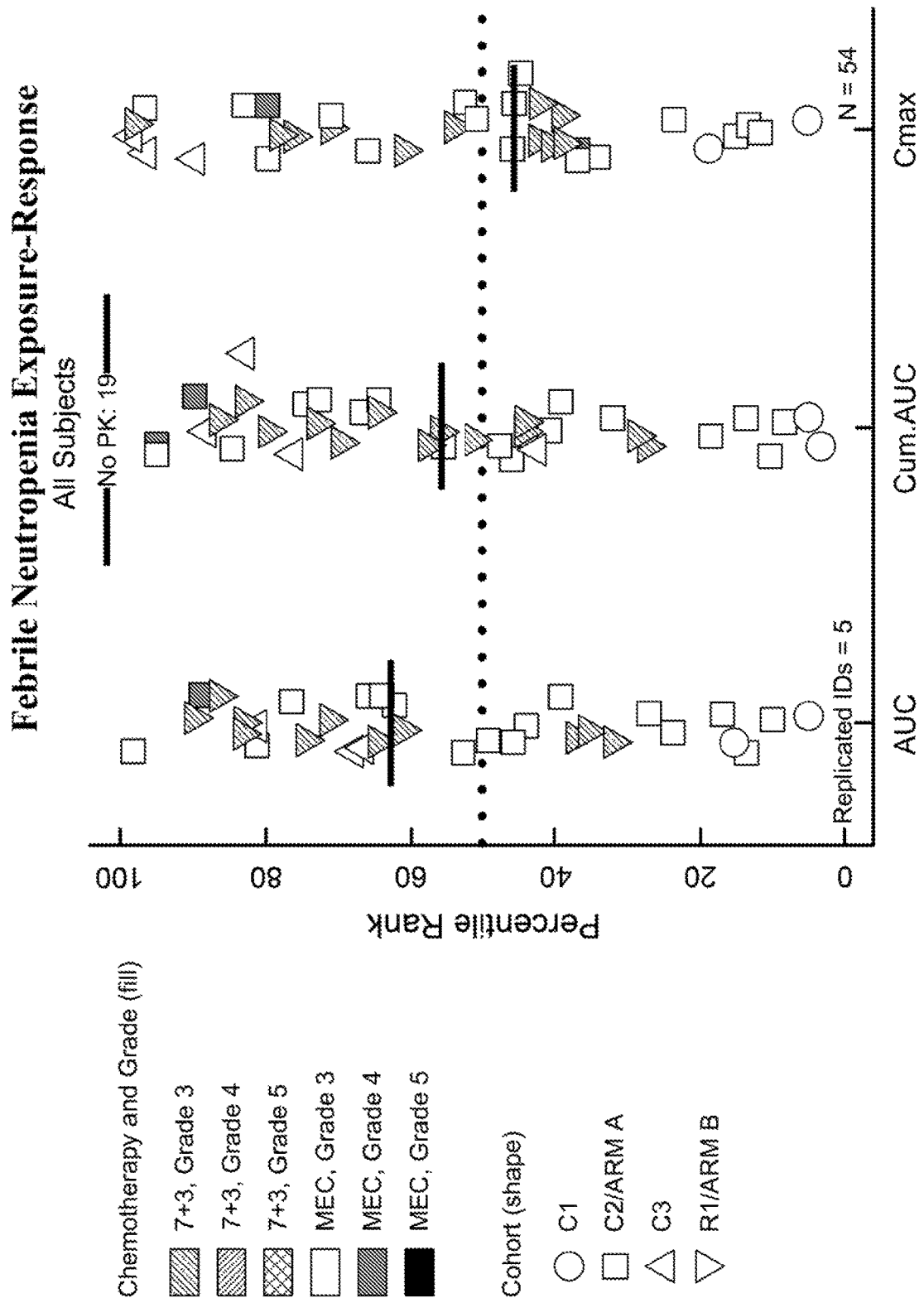
Figure 13F:
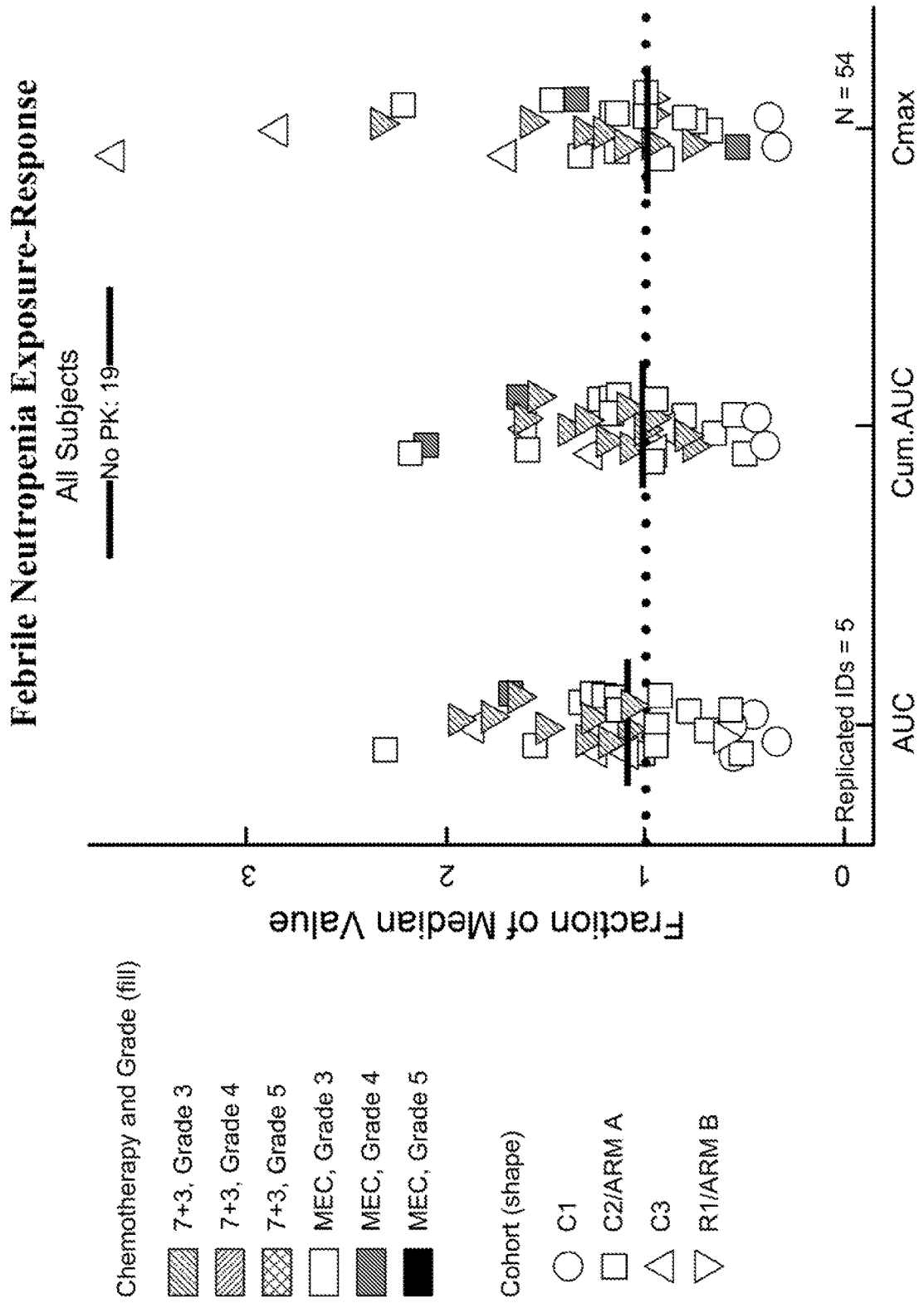
Figure 13G:
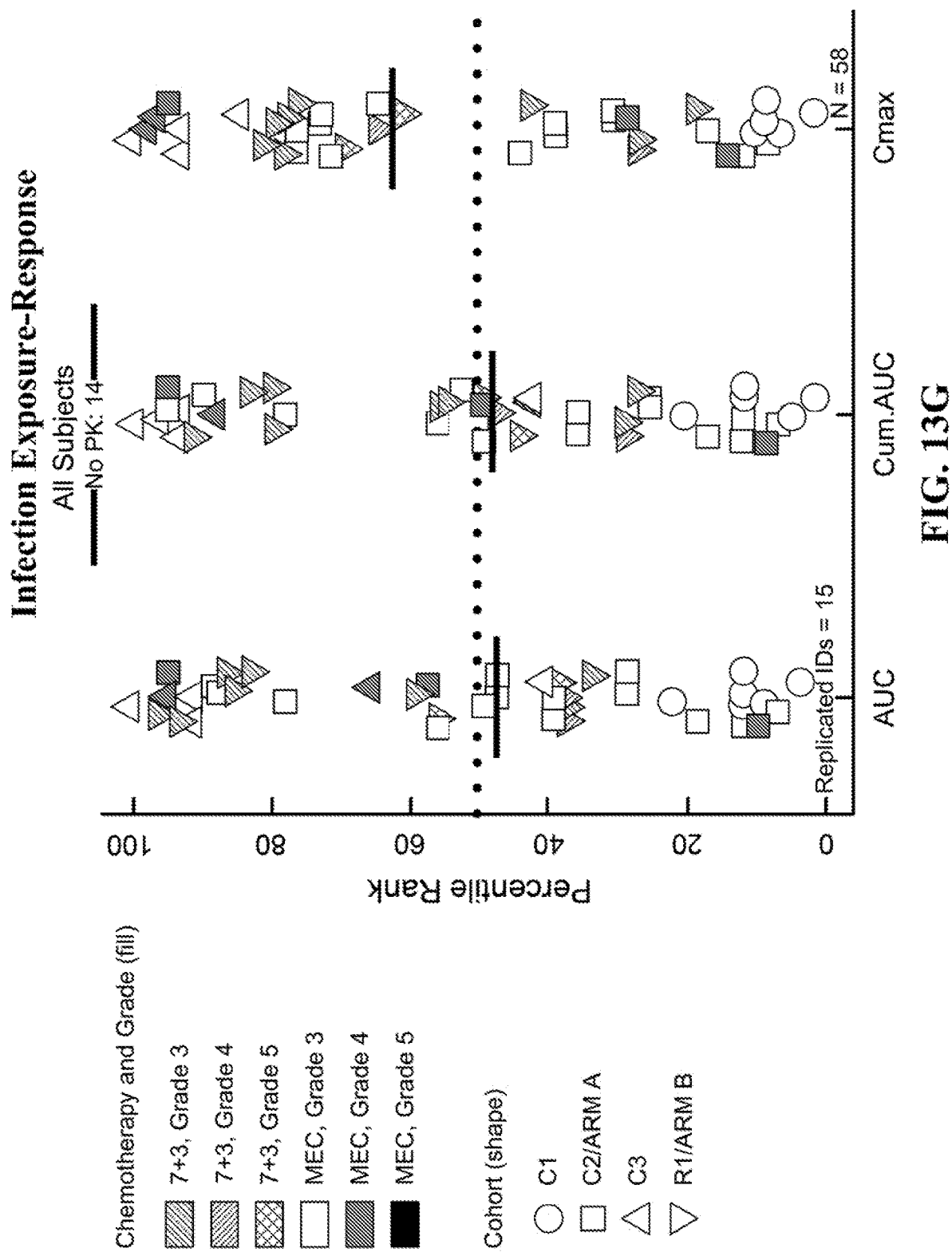
Figure 13H:
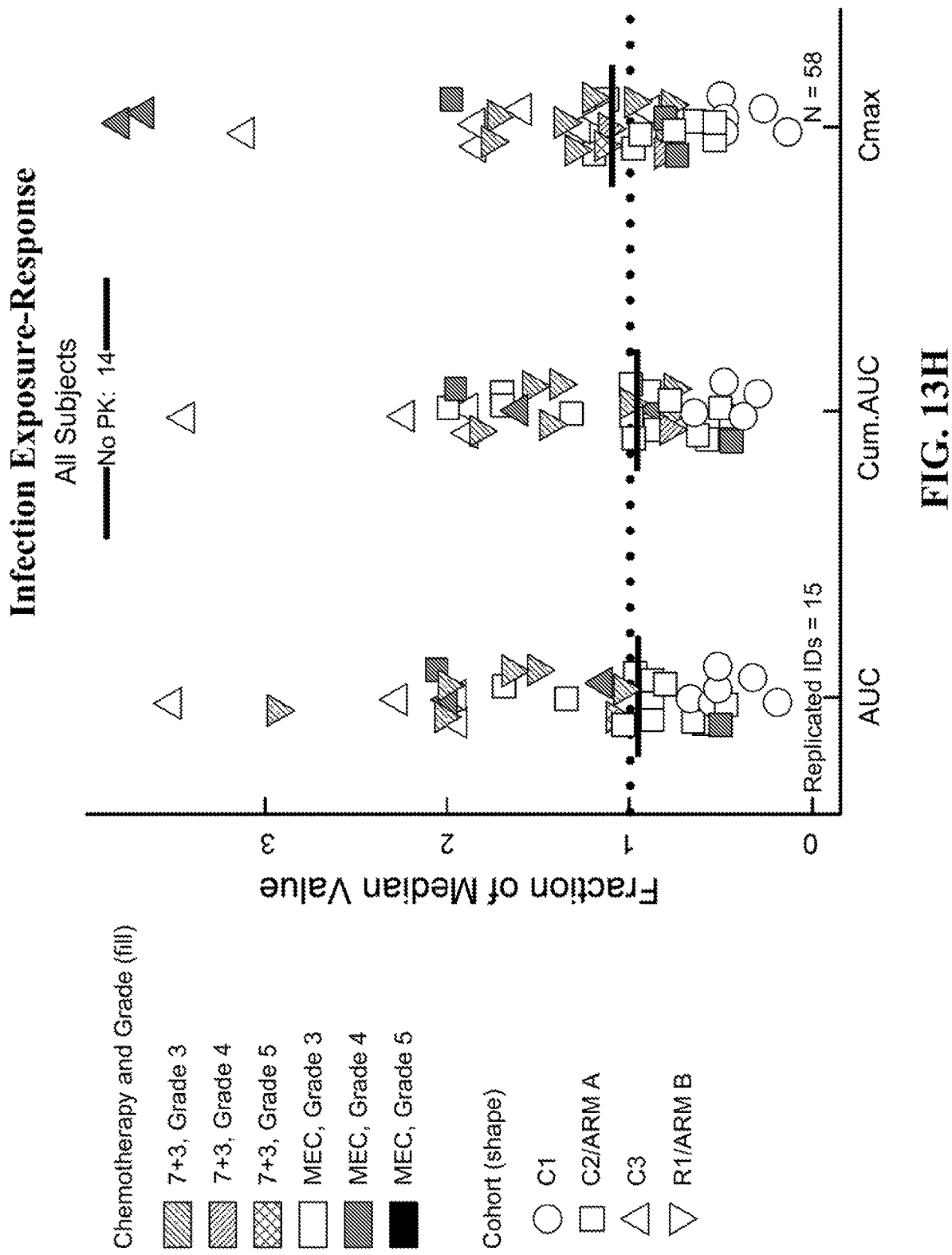
Figure 13I:
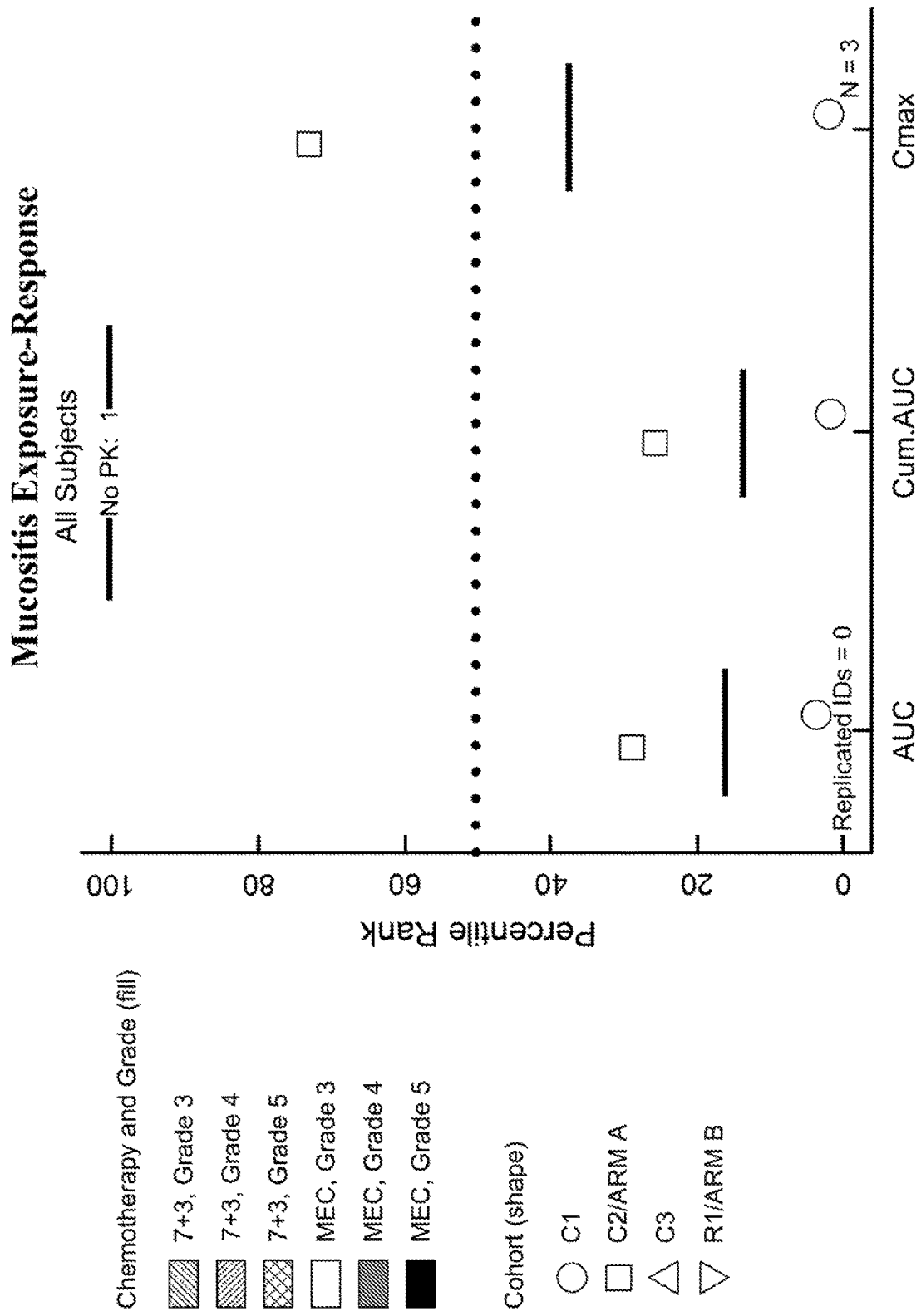
Figure 13J:
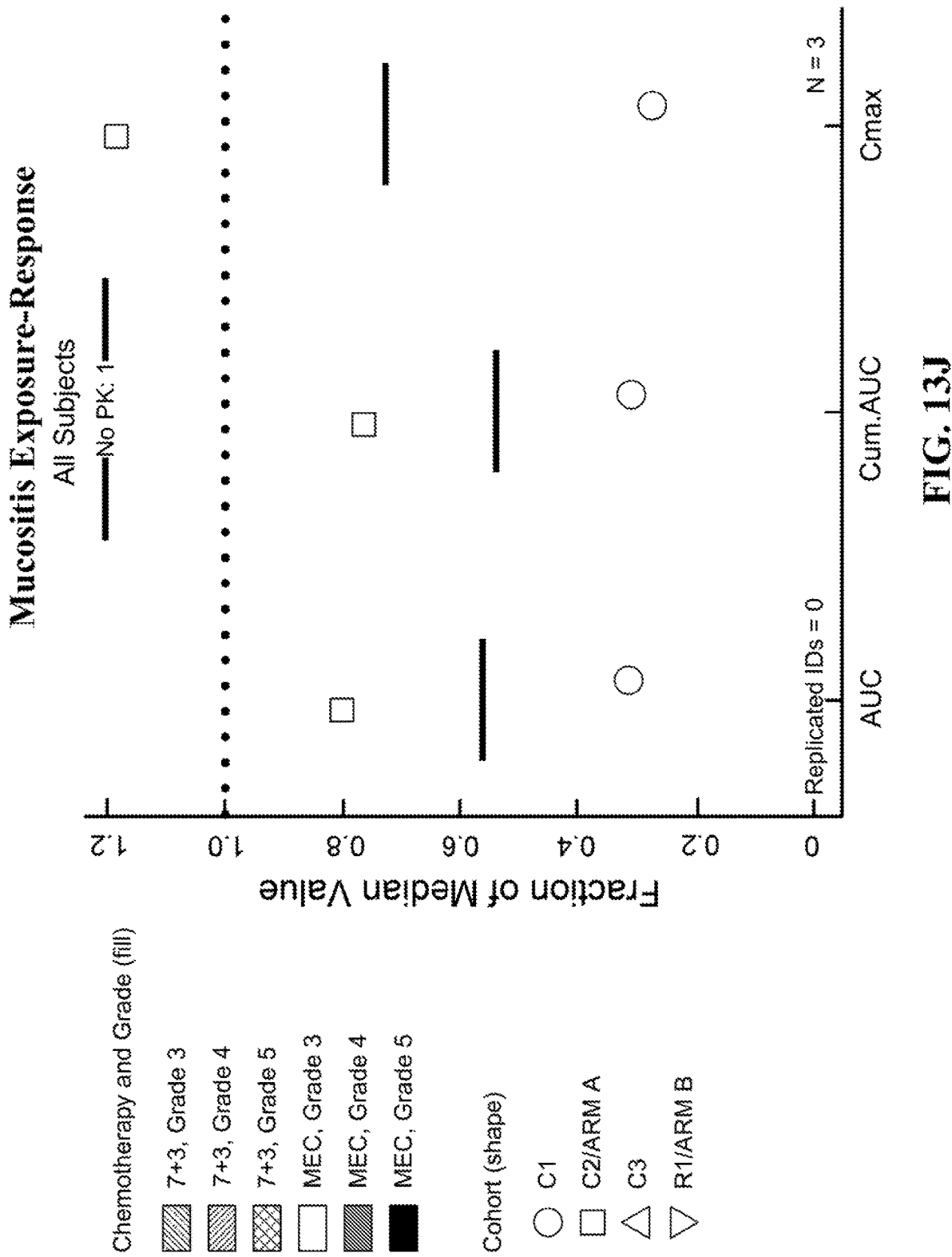
Figure 13K:
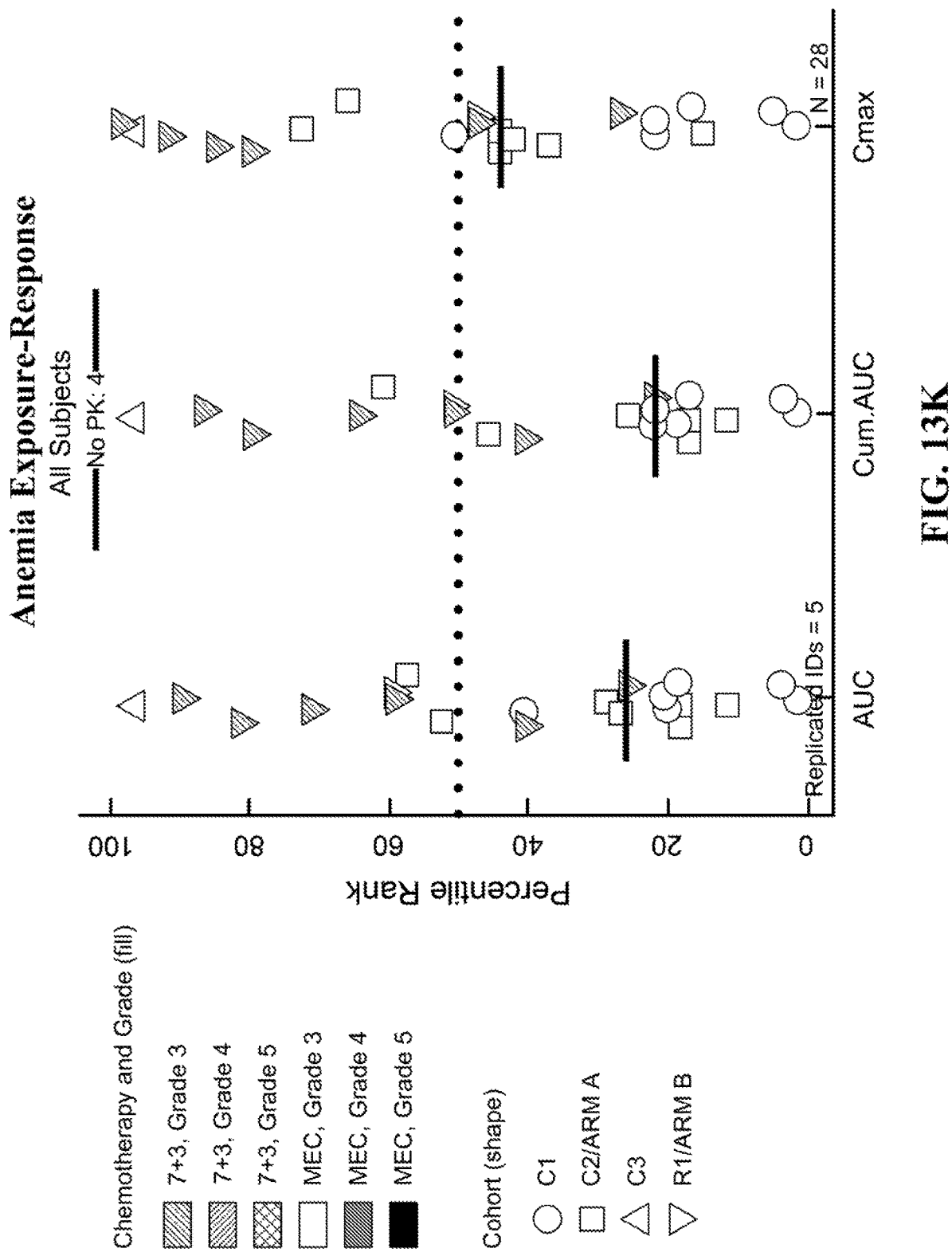
Figure 13L:
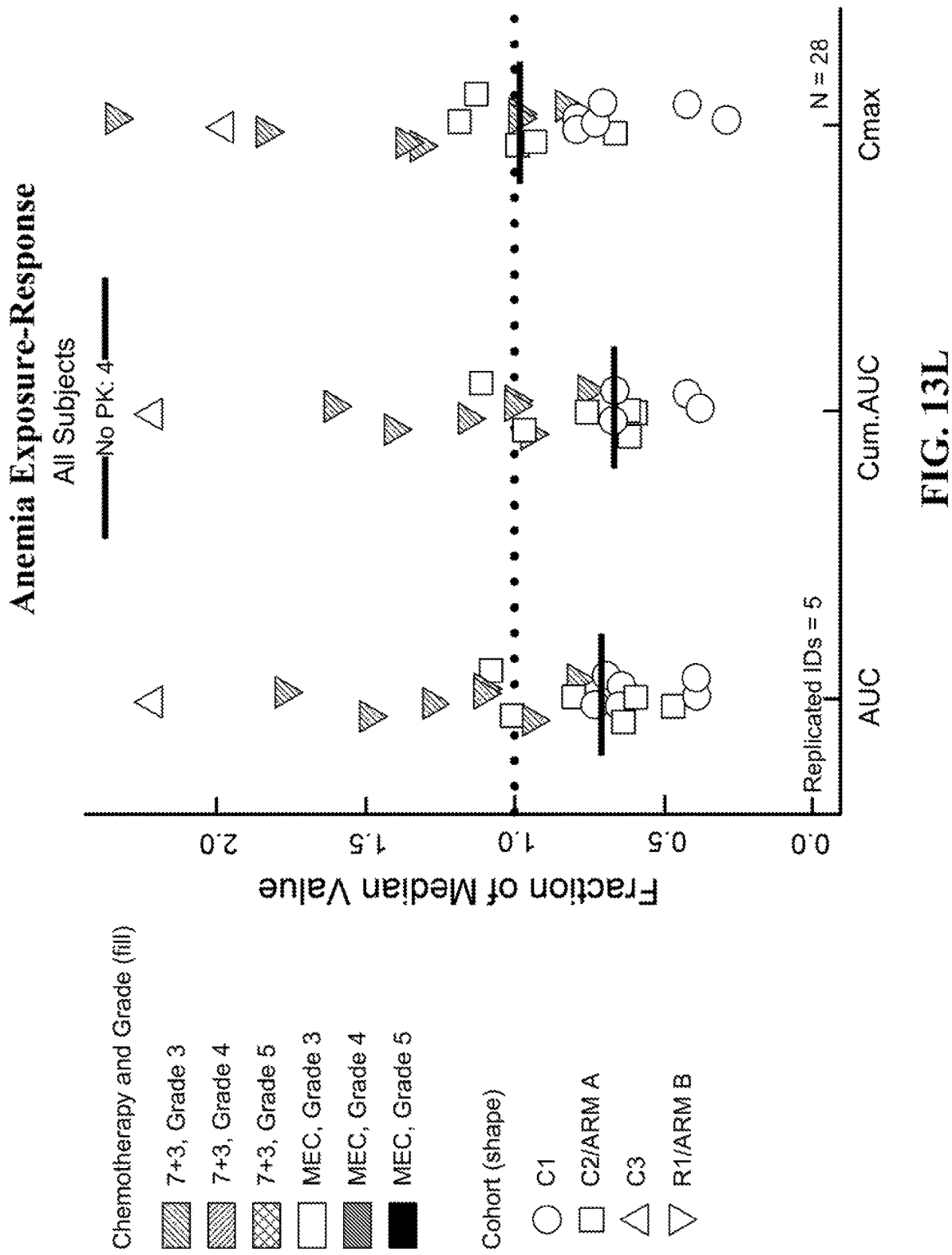

Adverse events ("AEs") were classified according the Common Terminology Criteria for Adverse Events ("CTCAE"). CTCAE AEs identified for E-R analyses were: neutropenia (FIGS. 13A and 13B), thrombocytopenia (FIGS. 13C and 13D), febrile neutropenia (FIGS. 13E and 13F), infection (FIGS. 13G and 13H), mucositis (FIGS. 13I and 13J), and anemia (FIGS. 13K and 13L). These events were categorized by CTCAE grade (3, 4, or 5), and by onset of dosing, either on or after the first day of dosing.

For each event, the study day (referenced to the first day of dosing) was identified. For an event occurring during dosing (typically, the first 8 days of Cycle 1), the corresponding percentile and normalized values (described above) were identified. If the event occurred after dosing (e.g., Day 15), concurrent exposure would be negligible; therefore, the following exposure metrics were applied:

a. Cmax: The highest Cmax attained at any time during treatment b. AUC, Cumulative AUC: Cumulative values Inspection of FIGS. 13A-F reveals no strong tendency toward increased AEs, nor increased severity of AEs with exposure as measured by AUC, cumulative AUC over the treatment cycle, or Cmax. Thus, the range of exposures presents a low safety risk to AML, subjects administered a compound of Formula (I) with cytotoxic chemotherapy.

Example 16

MEC and FAI Induction Chemotherapy Protocols

Figure 14A:
FIGS. 14A-14B illustrate select induction and consolidation treatment protocols. During induction subjects receive chemotherapy, either MEC or FAI, for five consecutive days and a compound of Formula (I) for eight consecutive days. Treatment with a compound of Formula (I) is initiated one day prior to initiating chemotherapy (FIG. 14A). During consolidation patients receive consolidation chemotherapy, HiDAC, IDAC option 1, IDAC option 2, or MEC. Treatment with a compound of Formula (I) is initiated one day prior to initiating consolidation chemotherapy with a single dose of a compound of Formula (1). Then Formula (1) is administered twice daily on chemotherapy days and twice daily for two days following the last dose of chemotherapy (FIG. 14B).
Figure 14A:
Figure 14A:
Figure 14A:

Subjects receive induction chemotherapy, either MEC or FAI, for 5 consecutive days. A compound of Formula (I) is given one day prior to initiating chemotherapy, each day during chemotherapy, and for two days following the last dose of chemotherapy (FIG. 14A). Subjects receiving MEC induction chemotherapy are treated with mitoxantrone 10 mg/m²/d IV over 15 to 20 minutes, etoposide 100 mg/m²/d IV over 60 minutes, and cytarabine 1000 mg/m²/d IV over 60 minutes for five consecutive days. Subjects receiving FAI induction chemotherapy are treated with fludarabine 30 mg/m² IV over 30 minutes for five consecutive days, cytarabine 2 g/m² IV over 4 hours for five consecutive days, and idarubicin 10 mg/m² IV for the first three consecutive days.

Example 17

MEC, HiDAC, and IDAC Consolidation Chemotherapy Protocols

Figure 14B:
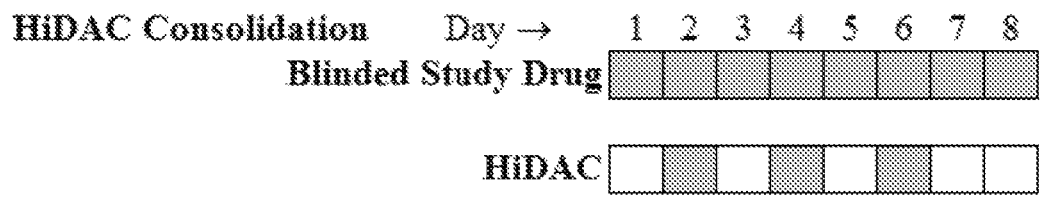
Figure 14B:
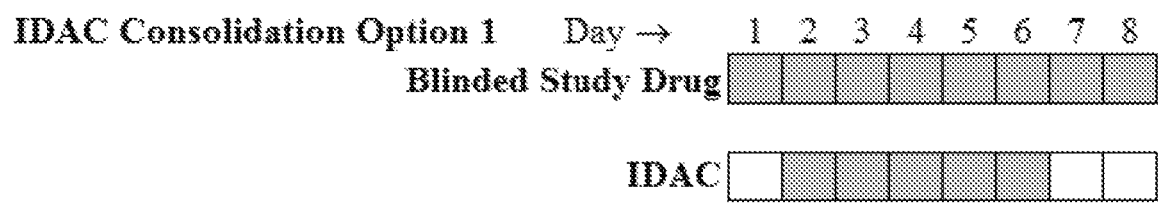
Figure 14B:
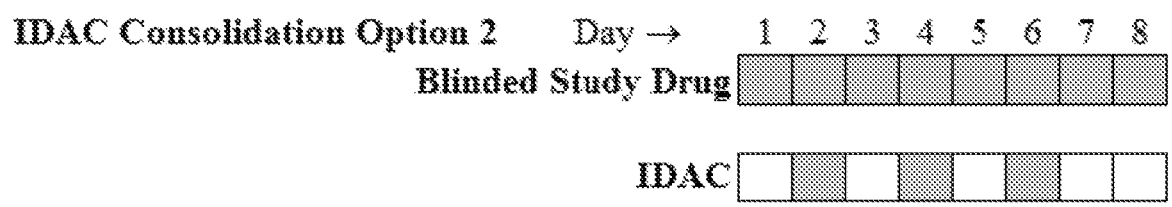
Figure 14B:
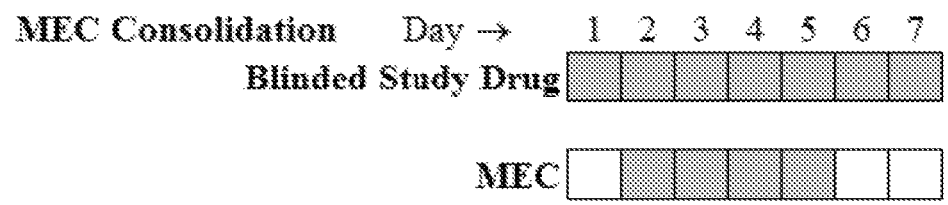

Subjects achieving remission following induction chemotherapy receive additional consolidation chemotherapy. Subjects receive reduced dose MEC, high-dose cytarabine (HiDAC), or intermediate-dose cytarabine (IDAC) consolidation chemotherapy. A compound of Formula (I) is given one day prior to initiating chemotherapy, each day during chemotherapy, and for two days following the last dose of chemotherapy (FIG. 14B). Reduced-dose MEC therapy consists of mitoxantrone 10 mg/m²/d IV over 15 to 20 minutes, etoposide 100 mg/m²/d IV over 60 minutes, and cytarabine 1000 mg/m²/d IV over 60 minutes on Days 2-5 for one cycle. HiDAC may be given as either of two regimens, for example, at the treating physician's discretion and in accordance with the NCCN guidelines, consisting of: cytarabine 3 g/m² IV every 3 hours on Days 2, 4 and 6 for up to 3-4 cycles, or cytarabine 2-3 g/m² IV every 12 hours on Days 2, 4 and 6 for up to 3-4 cycles. IDAC may be given as either of two regimens at the treating physician's discretion and in accordance with the NCCN guidelines consisting of: cytarabine 1.5 g/m²/day IV for 5 days for up to 3 cycles (the dose of cytarabine may be reduced to 1 g/m²/day at the treating physician's discretion), or cytarabine 1.5 g/m² IV over 3 hours every 12 hours on Days 2, 4, and 6 (total 6 doses) for up to 3 cycles (the dose of cytarabine may be reduced to 1 g/m²/day at the treating physician's discretion).

Example 18

Decitabine Chemotherapy Protocols

Subjects receive decitabine 20 mg/m² IV once daily for either 5 consecutive days or 10 consecutive days. Subjects receiving decitabine for 5 days are administered a compound of Formula (I), once per day prior to infusion of decitabine each day of chemotherapy. Subjects receiving decitabine for 10 days are administered a compound of Formula (I) twice per day each day of chemotherapy with one dose given prior to infusion of decitabine.

Example 19

7+3 Dauno Chemotherapy Protocol

A compound of Formula (I) is given one day prior to initiating chemotherapy, each day during chemotherapy, and for two days following the last dose of chemotherapy. Subjects receive a continuous IV infusion of cytarabine 100 mg/m²/d over seven days (168 hours), and daunorubicin 60 mg/m²/d IV for the first three consecutive days. On follow-up cycles, subjects may receive a continuous IV infusion of cytarabine 100 mg/m²/d over five days (120 hours), and daunorubicin 60 mg/m²/d IV for the first two consecutive days.

Example 20

7+3 IDA Chemotherapy Protocol

A compound of Formula (I) is given one day prior to initiating chemotherapy, each day during chemotherapy, and for two days following the last dose of chemotherapy. Subjects receive a continuous IV infusion of cytarabine 100 mg/m²/d over seven days (168 hours), and idarubicin 12 mg/m²/d IV for the first three consecutive days. On follow-up cycles, subjects may receive a continuous IV infusion of cytarabine 100 mg/m²/d over five days (120 hours), and idarubicin 12 mg/m²/d IV for the first two consecutive days.

Example 21

Clinical Outcomes—Relapsed/Refractory Subjects "Phase 2"

In this Phase 2 study related to the Phase 1 study described above (see Example 13), 47 additional subjects were administered the RP2D dose of 10 mg/kg/dose. The data of the 19 subjects in the 10 mg/kg/dose arm of the Phase 1 study was added to the data of these 47 additional subjects, resulting in data for 66 human subjects being considered in the Phase 2 study.

In detail, consistent with the Phase 1 study protocols, a total of 66 human subjects with relapsed/refractory (R/R) acute myeloid leukemia (AML) were selected for this study (i.e., the 19 subjects from the 10 mg/kg/dose arm of the Phase 1 study plus 47 additional subjects).

Whether as part of the Phase 1 study (for 19 of the subjects) or as an additional subject for the Phase 2 study, each subject received a total of 15 infusions of the RP2D dose of 10 mg/kg/dose of the compound of Formula (I), administered as the sodium salt, over 8 days with a nominal infusion duration of 20 minutes (either as part of the Phase 1 study for 19 subjects or as a new Phase 2). The formulation for the infusion solution was as follows:

| Component | Target Concentration |
| --- | --- |
| Compound of Formula (I) | 50 mg/mL |
| NaCl | 6.0 mg/mL |
| 10 mM TRIS buffer solution | 1.2 mg/mL |
| Water for injection | Quantity sufficient to volume |

The first dose of a compound of Formula (I) was administered 24 hours±1 hour prior to the first dose of MEC (mitoxantrone, etoposide, and cytarabine) induction chemotherapy as a sentinel dose to evaluate the effect of the compound of Formula (I) alone (i.e., a single dose of 10 mg/kg the day before the first chemotherapy day). The compound of Formula (I) was then administered every 12 hours±1 hour on chemotherapy days, starting 2 hours prior to chemotherapy (i.e., 20 mg/kg per day on chemotherapy days). Hence, the interval between the first and second dose of the compound of Formula (I) was approximately 24 hours. MEC chemotherapy was administered on Days 2-6.

The clinical outcome for each subject was assessed at the time of count recovery following completion of induction chemotherapy. Subjects were assigned to one of four response groups: complete remission ("CR"); complete remission with incomplete count recovery ("CRi"); morphologic leukemia-free state ("MLFS"); persistent disease ("PD"). Complete remission was defined as bone marrow blasts <5%; absence of circulating blasts and blasts with Auer rods; absence of extramedullary disease; ANC ≥1.0× $10^9$/L and platelets ≥100,000×$10^9$/L. Complete remission with incomplete recovery was defined as: all CR criteria except for residual neutropenia (<1.0×$10^9$/L) or thrombocytopenia (<100,000×$10^9$/L). Morphologic leukemia-free state was defined as: bone marrow blasts <5%; absence of blasts with Auer rods; absence of extramedullary disease; no hematologic recovery required. Persistent disease was defined as: bone marrow blasts >5%.

Outcomes shown below provide data for Phase 1 (Example 13, all cohorts combined), Phase 2, and Total (Phase 1 and Phase 2) subject populations.

| Outcome, reported as n (%) | Phase 1 | Phase 2 | Total | RP2D |
| --- | --- | --- | --- | --- |
| N Completing Induction Period | 19 | 47 | 66 | 54 |
| Response | | | | |
| CR + CRi | 9 (47) | 17 (36) | 26 (39) | 22 (41) |
| Complete Remission (CR) | 8 (42) | 14 (30) | 22 (33) | 19 (35) |
| CR with incomplete recovery (CRi) | 1 (5) | 3 (6) | 4 (6) | 3 (6) |
| CR + CRi + MLFS + PR | 10 (53) | 22 (47) | 32 (48) | 27 (50) |
| Morphologic Leukemia-Free State (MLFS) | 1 (5) | 3 (6) | 4 (6) | 3 (6) |
| Partial Remission (PR) | 0 | 2 (4) | 2 (3) | 2 (4) |
| Persistent Disease | 9 (47) | 25 (53) | 34 (52) | 27 (50) |
| All-Cause Mortality 30 days | 0 | 1 (2) | 1 (2) | 1 (2) |
| All-Cause Mortality 60 days | 2 (11) | 4 (9) | 6 (9) | 5 (9) |
| Proceeded to HSCT | 6 (32) | 11 (23) | 17 (26) | 16 (30) |

| Subgroup | CR/CRi Rate n (%) of sub-group | | | |
|---|---|---|---|---|
| | Phase 1 | Phase 2 | Total | RP2D |
| N Completing Induction Period | 19 | 47 | 66 | 54 |
| Primary Refractory | 4/7 (57) | 4/15 (27) | 8/22 (36) | 5/17 (29) |
| Relapsed | 5/12 (42) | 14/32 (44) | 19/44 (43) | 18/37 (49) |
| Relapsed <6 months | 1/5 (20) | 5/17 (29) | 6/22 (27) | 6/19 (32) |
| Relapsed 6-<12 months | 1/4 (25) | 3/7 (43) | 4/11 (36) | 3/7 (43) |
| Relapsed ≥12-<24 months | 0 | 3/4 (75) | 3/4 (75) | 3/4 (75) |
| Relapsed ≥24 months | 3/3 (100) | 3/4 (75) | 6/7 (86) | 6/7 (86) |
| Age <60 years | 7/14 (50) | 8/21 (38) | 15/35 (43) | 13/28 (46) |
| Age ≥60 years | 2/5 (40) | 10/26 (38) | 12/31 (39) | 10/26 (38) |
| Cytogenetics (SWOG) | | | | |
| Favorable risk | 0 | 1/1 (100) | 1/1 (100) | 1/1 (100) |
| e | 5/7 (71) | 7/17 (41) | 12/24 (50) | 10/20 (50) |
| Unfavorable risk | 4/12 (33) | 9/27 (33) | 13/39 (33) | 11/31 (35) |
| Cytogenetics (ELN) | | | | |
| Favorable risk | 2/2 (100) | 2/5 (40) | 4/7 (57) | 4/7 (57) |
| Intermediate risk | 2/2 (100) | 5/9 (56) | 7/11 (64) | 6/10 (60) |
| Adverse risk | 3/11 (27) | 5/22 (23) | 8/33 (24) | 6/25 (24) |
| Extramedullary disease | 1/1 (100) | 1/1 (100) | 2/2 (100) | 2/2 (100) |
| FLT3-ITD mutated | 0 | 2/3 (66) | 2/3 (66) | 2/3 (66) |
| TP53 mutation or monosomy 17 [del (17p)] | 0/1 (0) | 1/3 (33) | 1/4 (25) | 1/3 (33) |

These results demonstrate a response rate of over 40% (CR/CRi) after a single course of induction treatment with MEC and a compound of Formula (I). This rate is higher than expected response rate, given the high-risk cytogenetic and other disease features of the study population, when compared to historical controls of similar populations treated with MEC (see Feldman 2005; Greenberg 2004).

Adverse event data is provided below, showing the numbers and percentages for Grade 3/4 adverse events for several types of adverse events, and showing the numbers and percentages of both Grade 1/2 and 3/4 oral mucositis events.

| Grade 3/4 Adverse Events Event Type | Total N = 66 | RP2D N = 54 |
|---|---|---|
| Cardiac | 6 (9) | 5 (9) |
| Colitis | 2 (3) | 1 (2) |
| GI | 7 (11) | 4 (7) |
| Hepatic | 3 (5) | 3 (6) |
| Infectious | 50 (76) | 39 (72) |
| Bacteraemia | 8 (12) | 8 (15) |
| Febrile neutropenia | 31 (47) | 27 (50) |
| Sepsis | 12 (18) | 8 (15) |
| Oral Mucositis Events | | |
| Grades 1/2 | 14 (21) | 9 (17) |
| Grades 3/4 | 2 (3) | 1 (2) |

The severe oral mucositis rate was 2-3% in this trial group. The expected rate was >20% (see Feldman 2005).

Figure 15:
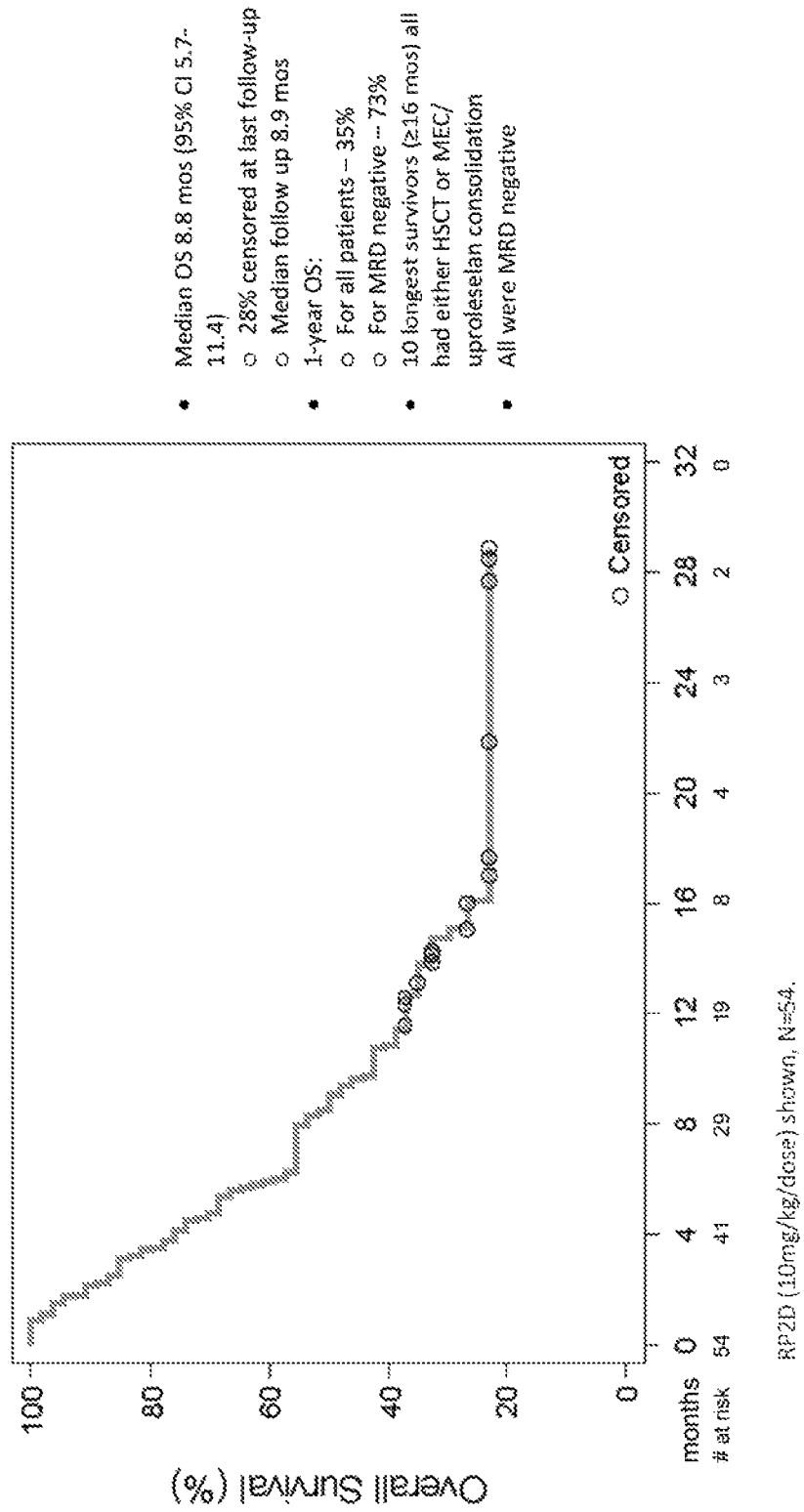
FIG. 15 illustrates the survival outcomes of 54 relapsed/refractory (R/R) AML, subjects administered the RP2D dose of 10 mg/kg/dose of a compound Formula (1) according to the protocol described in Example 21.

Survival data for these subjects is illustrated in FIG. 15. The median overall survival of the subjects was 8.8 months, with a 95% confidence interval of 5.7-11.4 months. The one-year survival rate for all subjects was 35%, and the one-year survival rate for MRD negative subjects was 73%.

Example 22

Clinical Outcomes—Newly Diagnosed Older Subjects

In this study, 25 human subjects who were newly diagnosed at age 60 or older with acute myeloid leukemia (AML) were selected for this study. Subjects were not disqualified for prior treatment or diagnosis for MDS or CMML.

Each subject received a total of 19 infusions of 10 mg/kg/dose of the compound of Formula (I), administered as the sodium salt, over 10 days with a nominal infusion duration of 20 minutes. The formulation for the infusion solution was as follows:

| Component | Target Concentration |
|---|---|
| Compound of Formula (I) | 50 mg/mL |
| NaCl | 6.0 mg/mL |
| 10 mM TRIS buffer solution | 1.2 mg/mL |
| Water for injection | Quantity sufficient to volume |

The first dose of a compound of Formula (I) was administered 24 hours±1 hour prior to the first dose of 7+3 (cytarabine and idarubicin) chemotherapy as a sentinel dose to evaluate the effect of the compound of Formula (I) alone (i.e., a single dose of 10 mg/kg the day before the first chemotherapy day). The compound of Formula (I) was then administered every 12 hours±1 hour on chemotherapy days (i.e., 20 mg/kg per day on chemotherapy days) and for two days following the last dose of chemotherapy. Hence, the interval between the first and second dose of the compound of Formula (I) was approximately 24 hours. 7+3 (cytarabine and idarubicin) chemotherapy was administered on Days 2-8 comprising a continuous IV infusion of cytarabine 100 mg/m²/d over seven days (168 hours, from days 2-8), and idarubicin 12 mg/m²/d IV for the first three consecutive days (36 hours, from days 2-4).

The clinical outcome for each subject was assessed at the time of count recovery following completion of induction chemotherapy. Subjects were assigned to one of four response groups: complete remission ("CR"); complete remission with incomplete count recovery ("CRi"); morphologic leukemia-free state ("MLFS"); persistent disease ("PD"). Complete remission was defined as bone marrow blasts <5%; absence of circulating blasts and blasts with Auer rods; absence of extramedullary disease; ANC ≥1.0×

$10^9$/L and platelets ≥100,000×$10^9$/L. Complete remission with incomplete recovery was defined as: all CR criteria except for residual neutropenia (<1.0×$10^9$/L) or thrombocytopenia (<100,000×$10^9$/L). Morphologic leukemia-free state was defined as: bone marrow blasts <5%; absence of blasts with Auer rods; absence of extramedullary disease; no hematologic recovery required. Persistent disease was defined as: bone marrow blasts >5%.

| Outcome | n (%) |
| --- | --- |
| N Completing Induction Period | 25 |
| N Receiving Re-Induction (5 + 2) | 8 (32) |
| Response | |
| CR + CRi | 18 (72) |
| Complete Remission (CR) | 13 (52) |
| CR with incomplete recovery (CRi) | 5 (20) |
| CR + CRi + MLFS | 20 (80) |
| Morphologic Leukemia-Free State (MLFS) | 2 (8) |
| Death Before Response Assessment | 2 (8) |
| Persistent Disease | 3 (12) |
| Proceeded to HSCT | 11 (44) |
| All-Cause Mortality 30 days | 2 (8) |
| All-Cause Mortality 60 days | 3 (12) |

| AML Subgroup | CR/CRi Rate n (%) of sub-group |
| --- | --- |
| N Completing Induction Period | 25 |
| de novo | 9/12 (75) |
| Secondary AML | 8/13 (62) |
| Cytogenetics (SWOG) | |
| Favorable risk | 1/1 (100) |
| Intermediate risk | 11/16 (69) |
| Unfavorable risk | 5/8 (63) |
| Cytogenetics (ELN) | |
| Favorable risk | 3/3 (100) |
| Intermediate risk | 4/7 (57) |
| Unfavorable risk | 8/12 (67) |
| FLT3-ITD mutated | 1/1 (100) |
| TP53 or monosomy 17 [del (17p)] | 1/2 (50) |

These results demonstrate a response rate of 72% (CR/CRi) after a single course of induction treatment with 7+3 (cytarabine and idarubicin) chemotherapy and a compound of Formula (I). This rate is higher than expected response rate, given the high-risk cytogenetic and other disease features of the study population, when compared to historical controls of similar populations treated with 7+3 (cytarabine and idarubicin) chemotherapy (see Burnett et al. The impact of dose escalation and resistance modulation in older patients with acute myeloid leukaemia and high-risk myelodysplastic syndrome: the results of the LRF AML14 trial. British J. Haematology, 2009. 145:218-332; Lancet, et al. Phase 2 trial of CPX-351, a fixed 5:1 molar ratio of cytarabine/daunorubicin, vs cytarabine/daunorubicin in older adults with untreated AML. Blood. 2014. 123(21): 3239-3246).

Adverse event data is provided below, showing the numbers and percentages for Grade 3/4 adverse events for several types of adverse events, and showing the numbers and percentages of both Grade 1/2 and 3/4 oral mucositis events.

| Grade 3/4 Adverse Events Event Type | Total N = 25 |
| --- | --- |
| Colitis | 3 (12) |
| Respiratory | 7 (28) |
| Infectious | 19 (76) |
| Febrile neutropenia | 17 (68) |
| Sepsis | 4 (16) |
| Pneumonia | 3 (12) |
| Oral Mucositis Events | |
| Grades 1/2 | 5 (20) |
| Grades 3/4 | 0 |

The severe oral mucositis rate was 0% in this trial group. The expected rate was approximately 5-10%.

Figure 16A:
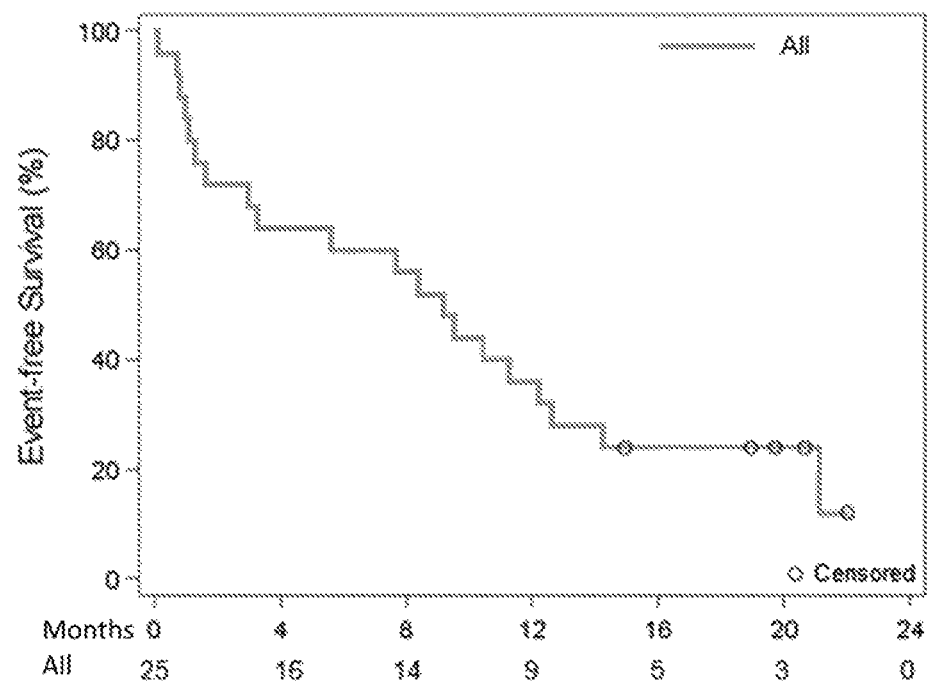
FIGS. 16A-16B illustrate the survival outcomes of 25 newly diagnosed older AML subjects (aged 60 years or older) administered the RP2D dose of 10 mg/kg/dose of a compound Formula (1) according to the protocol described in Example 22.
Figure 16B:
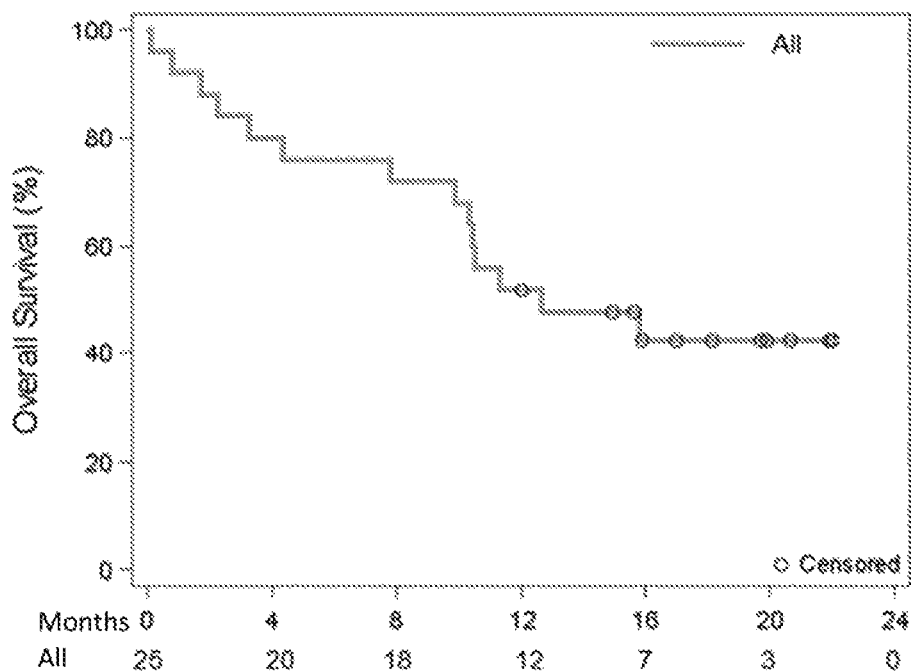

FIG. 16A illustrates the event-free survival data, and FIG. 16B illustrates the overall survival data for these subjects. The median event-free survival is 9.2 months with a 95% confidence interval of 3-12.6 months. The median overall survival is 12.6 months with a 95% confidence interval of lower range of 9.9 months (upper end of 95% confidence interval was not achieved). The one-year overall survival rate for all subjects was 52%, and the one-year survival rate for MRD negative subjects was 60%.

What is claimed is:

1. A method for treating a disease chosen from acute myeloid leukemia (AML), myelodysplastic syndrome (MDS), neutropenia, and mucositis comprising administering to a subject in need thereof a fixed dose of 800 mg to 3200 mg per day of a compound of Formula (I):

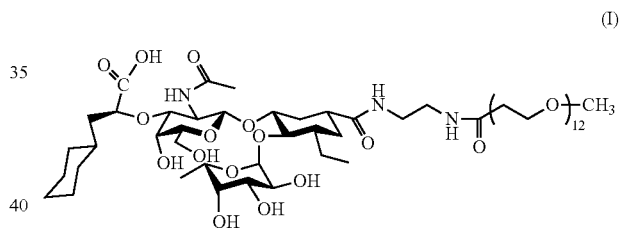

or a pharmaceutically acceptable salt thereof; and
wherein the subject is receiving, has received, or will receive one or more hypomethylating agents.

2. The method of claim 1, wherein 1600 mg per day of the compound of Formula (I) or pharmaceutically acceptable salt thereof is administered.

3. The method of claim 1, wherein the compound of Formula (I) or pharmaceutically acceptable salt thereof is administered twice daily.

4. The method of claim 1, wherein the compound of Formula (I) or pharmaceutically acceptable salt thereof is administered intravenously or subcutaneously.

5. The method of claim 1, wherein the subject is receiving, has received, or will receive chemotherapy and/or radiotherapy.

6. The method of claim 5, wherein the chemotherapy comprises administration of:
mitoxantrone, etoposide, and cytarabine;
fludarabine, cytarabine, and idarubicin; or
velafermin and/or palifermin.

7. The method of claim 5, wherein the subject further is receiving, has received, or will receive thalidomide or a thalidomide derivative.

8. The method of claim 1, wherein the disease is AML.

9. The method of claim 1, wherein the disease is MDS.

10. The method of claim 1, wherein the disease is neutropenia.

11. The method of claim 1, wherein the disease is mucositis.

12. The method of claim 1, wherein the compound of Formula (I) is administered as a pharmaceutically acceptable salt.

13. The method of claim 1, wherein 800 mg per day of the compound of Formula (I) or pharmaceutically acceptable salt thereof is administered.

14. The method of claim 1, wherein 3200 mg per day of the compound of Formula (I) or pharmaceutically acceptable salt thereof is administered.

15. The method of claim 6, wherein the chemotherapy comprises administration of: mitoxantrone, etoposide, and cytarabine.

16. The method of claim 6, wherein the chemotherapy comprises administration of: fludarabine, cytarabine, and idarubicin.

17. The method of claim 6, wherein the chemotherapy comprises administration of: velafermin and/or palifermin.

18. The method of claim 1, wherein the one or more hypomethylating agents comprises decitabine.

19. The method of claim 1, wherein the one or more hypomethylating agents comprises 5-azacitidine.

20. The method of claim 1, wherein the one or more hypomethylating agents comprises guadecitabine.

21. The method of claim 5, wherein the chemotherapy comprises administration of:
daunorubicin and cytarabine;
idasanutlin and cytarabine;
idarubicin and cytarabine;
gemtuzamab and ozogamicin;
fludarabine, cytarabine, and G-CSF;
fludarabine, cytarabine, idarubicin, and G-CSF;
mitoxantrone, fludarabine, cytarabine, and G-CSF;
fludarabine, cytarabine, and amsacrine;
fludarabine, cytarabine, amsacrine, and busulfan;
fludarabine, cytarabine, amsacrine, and melphalan; or
tioguanine, cytarabine, and daunorubicin.

22. The method of claim 21, wherein the chemotherapy comprises administration of idarubicin and cytarabine.

23. The method of claim 1, wherein the subject is receiving, has received, or will receive one or more antimetabolites chosen from 5-fluorouracil, foxuridine, cytarabine, capecitibine, gemcitabine, 6-mercaptopurine, 6-thioguanine, cladribine, fludarabine, nelarabine, or pentostatin.

24. A method for treating a disease chosen from acute myeloid leukemia (AML), myelodysplastic syndrome (MDS), neutropenia, and mucositis comprising administering to a subject in need thereof a fixed dose of 800 mg to 3200 mg per day of a compound of Formula (I):

or a pharmaceutically acceptable salt thereof;
wherein the subject is receiving, has received, or will receive chemotherapy comprising administration of fludarabine, cytarabine, and idarubicin.

25. The method of claim 24, wherein 1600 mg per day of the compound of Formula (I) or pharmaceutically acceptable salt thereof is administered.

26. The method of claim 24, wherein the compound of Formula (I) or pharmaceutically acceptable salt thereof is administered twice daily.

27. The method of claim 24, wherein the compound of Formula (I) or pharmaceutically acceptable salt thereof is administered intravenously or subcutaneously.

28. The method of claim 24, wherein the subject further is receiving, has received, or will receive thalidomide or a thalidomide derivative.

29. The method of claim 24, wherein the disease is AML.

30. The method of claim 24, wherein the disease is MDS.

31. The method of claim 24, wherein the disease is neutropenia.

32. The method of claim 24, wherein the disease is mucositis.

33. The method of claim 24, wherein the compound of Formula (I) is administered as a pharmaceutically acceptable salt.

34. The method of claim 24, wherein 800 mg per day of the compound of Formula (I) or pharmaceutically acceptable salt thereof is administered.

35. The method of claim 24, wherein 3200 mg per day of the compound of Formula (I) or pharmaceutically acceptable salt thereof is administered.

36. The method of claim 24, wherein the subject further is receiving, has received, or will receive one or more hypomethylating agents.

37. The method of claim 36, wherein the one or more hypomethylating agents comprises decitabine.

38. The method of claim 36, wherein the one or more hypomethylating agents comprises 5-azacitidine.

39. The method of claim 36, wherein the one or more hypomethylating agents comprises guadecitabine.

40. The method of claim 24, wherein the subject is receiving, has received, or will receive one or more antimetabolites chosen from 5-fluorouracil, foxuridine, capecitibine, gemcitabine, 6-mercaptopurine, 6-thioguanine, cladribine, fludarabine, nelarabine, or pentostatin.

41. A method for treating a disease chosen from acute myeloid leukemia (AML), myelodysplastic syndrome (MDS), neutropenia, and mucositis comprising administering to a subject in need thereof a fixed dose of 800 mg to 3200 mg per day of a compound of Formula (I):

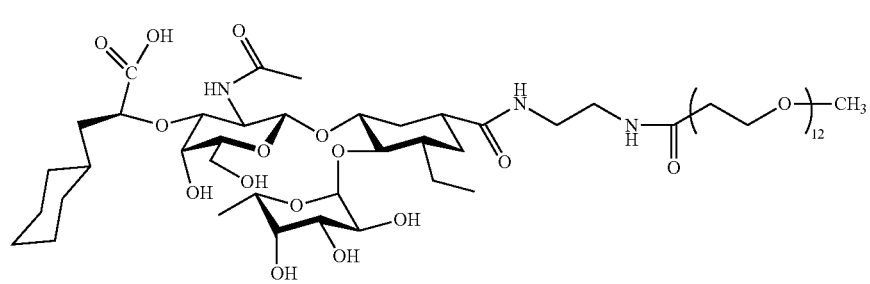

(I)

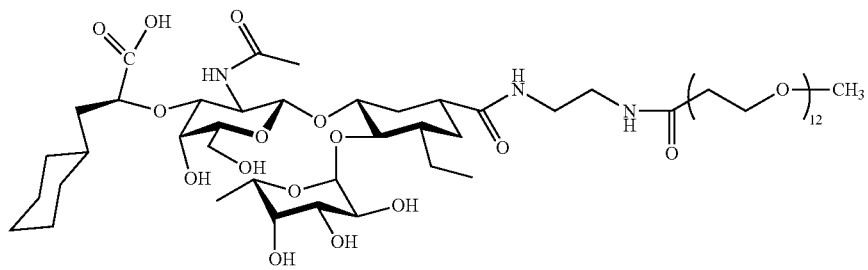

(I)

or a pharmaceutically acceptable salt thereof;
wherein the subject is receiving, has received, or will receive chemotherapy comprising administration of velafermin and/or palifermin.

42. The method of claim 41, wherein 1600 mg per day of the compound of Formula (I) or pharmaceutically acceptable salt thereof is administered.

43. The method of claim 41, wherein the compound of Formula (I) or pharmaceutically acceptable salt thereof is administered twice daily.

44. The method of claim 41, wherein the compound of Formula (I) or pharmaceutically acceptable salt thereof is administered intravenously or subcutaneously.

45. The method of claim 41, wherein the subject further is receiving, has received, or will receive thalidomide or a thalidomide derivative.

46. The method of claim 41, wherein the disease is AML.

47. The method of claim 41, wherein the disease is MDS.

48. The method of claim 41, wherein the disease is neutropenia.

49. The method of claim 41, wherein the disease is mucositis.

50. The method of claim 41, wherein the compound of Formula (I) is administered as a pharmaceutically acceptable salt.

51. The method of claim 41, wherein 800 mg per day of the compound of Formula (I) or pharmaceutically acceptable salt thereof is administered.

52. The method of claim 41, wherein 3200 mg per day of the compound of Formula (I) or pharmaceutically acceptable salt thereof is administered.

53. The method of claim 41, wherein the subject further is receiving, has received, or will receive one or more hypomethylating agents.

54. The method of claim 53, wherein the one or more hypomethylating agents comprises decitabine.

55. The method of claim 53, wherein the one or more hypomethylating agents comprises 5-azacitidine.

56. The method of claim 53, wherein the one or more hypomethylating agents comprises guadecitabine.

57. The method of claim 41, wherein the subject is receiving, has received, or will receive one or more antimetabolites chosen from 5-fluorouracil, foxuridine, cytarabine, capecitibine, gemcitabine, 6-mercaptopurine, 6-thioguanine, cladribine, fludarabine, nelarabine, or pentostatin.

* * * * *